US012156664B2

(12) United States Patent
Lee et al.

(10) Patent No.: US 12,156,664 B2
(45) Date of Patent: Dec. 3, 2024

(54) RESECTION GUIDES, SWEEPING REAMERS, AND METHODS FOR USE IN TOTAL ANKLE REPLACEMENT

(71) Applicant: Paragon 28, Inc., Englewood, CO (US)

(72) Inventors: Daniel J. Lee, Denver, CO (US);
Joseph Dogué, Aurora, CO (US);
Albert Dacosta, Lone Tree, CO (US);
Francis D. Barmes, Parker, CO (US);
Jeffrey Christensen, Everett, WA (US)

(73) Assignee: Paragon 28, Inc., Englewood, CO (US)

( * ) Notice: Subject to any disclaimer, the term of this patent is extended or adjusted under 35 U.S.C. 154(b) by 321 days.

(21) Appl. No.: 17/654,527

(22) Filed: Mar. 11, 2022

(65) Prior Publication Data

US 2022/0192686 A1 Jun. 23, 2022

Related U.S. Application Data

(63) Continuation of application No. 17/345,398, filed on Jun. 11, 2021, now Pat. No. 11,272,944, which is a
(Continued)

(51) Int. Cl.
*A61B 17/17* (2006.01)
*A61B 17/15* (2006.01)
(Continued)

(52) U.S. Cl.
CPC .......... *A61B 17/1775* (2016.11); *A61B 17/15* (2013.01); *A61B 17/66* (2013.01); *A61B 2017/00477* (2013.01)

(58) Field of Classification Search
CPC ............................ A61B 17/1775; A61B 17/15
See application file for complete search history.

(56) References Cited

U.S. PATENT DOCUMENTS 3,710,473 A 1/1973 McElwain
3,750,652 A 8/1973 Sherwin
(Continued)

FOREIGN PATENT DOCUMENTS

CN 102405024 4/2012
CN 102770067 11/2012
(Continued)

OTHER PUBLICATIONS

Extended European Search Report issued in European Patent Application No. 19896955.2, 9 pages, dated Oct. 21, 2022.
(Continued)

*Primary Examiner* — Christian A Sevilla
(74) *Attorney, Agent, or Firm* — Heslin Rothenberg Farley & Mesiti PC

(57) ABSTRACT

Resection guides include a body a plurality of alignment pin through-holes and a plurality of guide through-holes so that the pattern of guide through-holes is operable for receiving a drill for use in resecting the at least a portion of the anatomical structure of the patient. Sweeping reamers include a body having a plurality of alignment pin through-holes and an elongated opening, and a reamer extendable through the elongated opening of the body. Decoupled resection guides include a first body having a plurality of alignment pin through-holes and a second body having a plurality of fixation pin through-holes and at least one guide aperture operable for guiding a cutting tool for use in resecting a portion of the second anatomical structure of the patient. Methods employing the same are disclosed and operable in, for example, total ankle replacement.

5 Claims, 56 Drawing Sheets

Related U.S. Application Data continuation of application No. PCT/US2019/064948, filed on Dec. 6, 2019.

(60) Provisional application No. 62/898,615, filed on Sep. 11, 2019, provisional application No. 62/779,436, filed on Dec. 13, 2018.

(51) Int. Cl.
*A61B 17/66* (2006.01)
*A61B 17/86* (2006.01)
*A61B 17/00* (2006.01)

(56) References Cited

U.S. PATENT DOCUMENTS

| | | | |
|---|---|---|---|
| 4,757,810 A * | 7/1988 | Reese | A61B 17/15 606/82 |
| 4,899,761 A | 2/1990 | Brown | |
| 4,938,762 A * | 7/1990 | Wehrli | A61B 17/154 606/88 |
| 5,078,719 A * | 1/1992 | Schreiber | A61B 17/15 606/87 |
| 5,234,433 A * | 8/1993 | Bert | A61B 17/8847 606/88 |
| 5,429,121 A | 7/1995 | Gadelius | |
| 5,449,360 A * | 9/1995 | Schreiber | A61B 17/152 606/87 |
| 5,540,696 A * | 7/1996 | Booth, Jr. | A61B 17/025 606/88 |
| 5,628,750 A | 5/1997 | Whitlock | |
| 5,702,464 A | 12/1997 | Lackey | |
| 6,030,391 A * | 2/2000 | Brainard | A61B 17/15 606/82 |
| 6,033,440 A | 3/2000 | Schall | |
| 6,241,729 B1 | 6/2001 | Estes | |
| 6,261,296 B1 | 7/2001 | Aebi | |
| 6,551,316 B1 | 4/2003 | Rinner | |
| 6,673,116 B2 | 1/2004 | Reiley | |
| 6,739,068 B1 | 5/2004 | Rinner | |
| 6,875,236 B2 | 4/2005 | Reiley | |
| 7,025,790 B2 | 4/2006 | Parks | |
| 7,153,281 B2 | 12/2006 | Holmes | |
| 7,468,075 B2 | 12/2008 | Lang | |
| 7,534,263 B2 | 5/2009 | Burdulis, Jr. | |
| 7,547,327 B2 | 6/2009 | Collazo | |
| 7,618,451 B2 | 11/2009 | Berez | |
| 7,744,601 B2 | 6/2010 | Rosa et al. | |
| 7,981,158 B2 | 7/2011 | Fitz | |
| 8,002,841 B2 | 8/2011 | Hasselman | |
| 8,062,302 B2 | 11/2011 | Lang | |
| 8,083,745 B2 | 12/2011 | Lang | |
| 8,092,465 B2 | 1/2012 | Metzger | |
| 8,105,330 B2 | 1/2012 | Fitz | |
| 8,114,091 B2 | 2/2012 | Ratron | |
| 8,147,557 B2 | 4/2012 | Lee | |
| 8,357,166 B2 | 1/2013 | Aram | |
| 8,366,771 B2 | 2/2013 | Burdulis, Jr. | |
| 8,439,951 B2 | 5/2013 | Trautwein | |
| 8,460,304 B2 | 6/2013 | Fitz | |
| 8,585,708 B2 | 11/2013 | Fitz | |
| 8,617,172 B2 | 12/2013 | Fitz | |
| 8,657,827 B2 | 2/2014 | Fitz | |
| 8,951,259 B2 | 2/2015 | Fitz et al. | |
| 8,951,260 B2 | 2/2015 | Lang | |
| 8,965,088 B2 | 2/2015 | Tsougarakis et al. | |
| 8,979,866 B2 | 3/2015 | Patel | |
| 9,023,050 B2 | 5/2015 | Lang | |
| 9,066,728 B2 | 6/2015 | Burdulis, Jr. | |
| 9,072,531 B2 | 7/2015 | Fitz et al. | |
| 9,107,680 B2 | 8/2015 | Fitz et al. | |
| 9,125,672 B2 | 9/2015 | Fitz et al. | |
| 9,125,673 B2 | 9/2015 | Fitz et al. | |
| 9,186,161 B2 | 11/2015 | Lang | |
| 9,220,517 B2 | 12/2015 | Lang | |
| 9,220,518 B2 | 12/2015 | Neal et al. | |
| 9,326,780 B2 | 5/2016 | Wong et al. | |
| 9,351,773 B2 | 5/2016 | DiDomenico | |
| 9,358,018 B2 | 6/2016 | Fitz | |
| 9,402,640 B2 | 8/2016 | Reynolds et al. | |
| 9,480,571 B2 | 11/2016 | Luna et al. | |
| 9,907,561 B2 | 3/2018 | Luna et al. | |
| 9,918,724 B2 | 3/2018 | Luna et al. | |
| 9,974,588 B2 | 5/2018 | Stemniski et al. | |
| 9,993,254 B2 | 6/2018 | Loring et al. | |
| 10,058,335 B2 | 8/2018 | Lee et al. | |
| 10,182,832 B1 | 1/2019 | Saltzman et al. | |
| 10,321,922 B2 | 6/2019 | McGinley et al. | |
| 11,116,521 B2 | 9/2021 | McGinley et al. | |
| 11,337,711 B2 | 5/2022 | Goble et al. | |
| 11,399,949 B2 | 8/2022 | Dogue | |
| 2001/0029377 A1 | 10/2001 | Aebi | |
| 2002/0055744 A1* | 5/2002 | Reiley | A61B 17/1775 623/21.18 |
| 2003/0105467 A1 | 6/2003 | Ralph et al. | |
| 2003/0204265 A1 | 10/2003 | Short | |
| 2003/0225416 A1 | 12/2003 | Bonvallet | |
| 2004/0039394 A1* | 2/2004 | Conti | A61B 17/15 606/87 |
| 2005/0004676 A1 | 1/2005 | Schon | |
| 2005/0021039 A1 | 1/2005 | Cusick | |
| 2005/0049603 A1 | 3/2005 | Calton et al. | |
| 2005/0070897 A1 | 3/2005 | Petersen | |
| 2005/0267600 A1 | 12/2005 | Haberman | |
| 2005/0288792 A1 | 12/2005 | Landes | |
| 2006/0142870 A1 | 6/2006 | Robinson et al. | |
| 2006/0229730 A1 | 10/2006 | Railey | |
| 2006/0247646 A1 | 11/2006 | Bihary | |
| 2007/0043375 A1 | 2/2007 | Anissian | |
| 2007/0073296 A1 | 3/2007 | Panchbhavi | |
| 2007/0073405 A1 | 3/2007 | Verhulst | |
| 2007/0100347 A1 | 5/2007 | Stad | |
| 2007/0123904 A1 | 5/2007 | Stad | |
| 2007/0173858 A1 | 7/2007 | Engh et al. | |
| 2007/0270783 A1 | 11/2007 | Zumsteg et al. | |
| 2008/0015599 A1 | 1/2008 | D'Alessio | |
| 2008/0082169 A1 | 4/2008 | Gittings et al. | |
| 2008/0103603 A1 | 5/2008 | Hintermann | |
| 2008/0114369 A1 | 5/2008 | Bastian | |
| 2008/0269757 A1 | 10/2008 | McMinn | |
| 2009/0209964 A1 | 8/2009 | Yeung | |
| 2009/0234360 A1 | 9/2009 | Alexander | |
| 2009/0312807 A1 | 12/2009 | Boudreault et al. | |
| 2010/0121334 A1 | 5/2010 | Couture | |
| 2010/0161077 A1 | 6/2010 | Boone | |
| 2010/0217338 A1 | 8/2010 | Carroll | |
| 2010/0331848 A1 | 12/2010 | Smith | |
| 2011/0208093 A1 | 8/2011 | Gross | |
| 2011/0218542 A1 | 9/2011 | Lian | |
| 2011/0218543 A1 | 9/2011 | van der Walt | |
| 2012/0053592 A1 | 3/2012 | Burgi | |
| 2012/0101504 A1 | 4/2012 | Habegger | |
| 2012/0130376 A1 | 5/2012 | Loring | |
| 2012/0130434 A1* | 5/2012 | Stemniski | A61B 17/1775 606/86 R |
| 2012/0158152 A1 | 6/2012 | Claypool | |
| 2012/0232558 A1 | 9/2012 | Berberich | |
| 2012/0239045 A1 | 9/2012 | Li | |
| 2012/0259335 A1 | 10/2012 | Scifert | |
| 2012/0271314 A1 | 10/2012 | Stemniski | |
| 2012/0277745 A1 | 11/2012 | Lizee | |
| 2013/0046313 A1 | 2/2013 | Lian | |
| 2013/0060253 A1 | 3/2013 | Couture | |
| 2013/0085499 A1 | 4/2013 | Lian | |
| 2013/0088549 A1 | 4/2013 | Loring | |
| 2013/0116797 A1 | 5/2013 | Coulange et al. | |
| 2014/0018931 A1 | 1/2014 | Gillard | |
| 2014/0025127 A1 | 1/2014 | Richter | |
| 2014/0128979 A1 | 5/2014 | Womble et al. | |
| 2014/0163563 A1 | 6/2014 | Reynolds et al. | |
| 2014/0188236 A1 | 7/2014 | McGinley et al. | |
| 2014/0236157 A1 | 8/2014 | Tochigi et al. | |
| 2014/0336658 A1 | 11/2014 | Luna et al. | |
| 2014/0371865 A1 | 12/2014 | Firestone | |

(56) References Cited

U.S. PATENT DOCUMENTS

| | | |
|---|---|---|
| 2015/0157339 A1 | 6/2015 | McGinley |
| 2015/0182273 A1 | 7/2015 | Stemniski et al. |
| 2015/0265265 A1 | 9/2015 | Hynes et al. |
| 2015/0282952 A1 | 10/2015 | Hes et al. |
| 2015/0305753 A1 | 10/2015 | McGinley et al. |
| 2015/0313727 A1 | 11/2015 | Waite, II |
| 2015/0359642 A1 | 12/2015 | Claypool et al. |
| 2016/0074053 A1 | 3/2016 | Hutchinson |
| 2016/0135815 A1 | 5/2016 | Loring et al. |
| 2016/0278754 A1 | 9/2016 | Todorov et al. |
| 2016/0367269 A9 | 12/2016 | McGinley et al. |
| 2017/0079670 A1 | 3/2017 | Haines |
| 2017/0112586 A1 | 4/2017 | Dhupar |
| 2017/0238946 A1 | 8/2017 | van der Walt et al. |
| 2017/0290597 A1 | 10/2017 | Goble et al. |
| 2017/0340450 A1 | 11/2017 | Toro Arbelaez |
| 2017/0354425 A1 | 12/2017 | Zaima |
| 2018/0125663 A1 | 5/2018 | Huxel et al. |
| 2018/0146970 A1 | 5/2018 | Luna et al. |
| 2018/0168826 A1 | 6/2018 | van der Walt et al. |
| 2018/0177511 A1 | 6/2018 | Luna et al. |
| 2018/0177513 A1 | 6/2018 | Stemniski et al. |
| 2018/0221074 A1 | 8/2018 | Dacosta et al. |
| 2018/0243023 A1 | 8/2018 | Stemniski et al. |
| 2018/0263639 A1 | 9/2018 | McGinley |
| 2018/0280038 A1 | 10/2018 | Goble |
| 2018/0280069 A1 | 10/2018 | Barmes et al. |
| 2018/0289380 A1 | 10/2018 | Mauldin et al. |
| 2018/0303490 A1 | 10/2018 | Loring et al. |
| 2018/0317940 A1 | 11/2018 | Stemniski et al. |
| 2019/0133612 A1 | 5/2019 | McGinley et al. |
| 2020/0046412 A1 | 2/2020 | Nachtrab et al. |
| 2020/0085452 A1 | 3/2020 | Siegler |
| 2020/0113712 A1 | 4/2020 | Luna et al. |

FOREIGN PATENT DOCUMENTS

| | | |
|---|---|---|
| CN | 107361883 | 11/2017 |
| CN | 108969162 | 12/2018 |
| EP | 1260183 | 11/2002 |
| FR | 2700462 | 7/1994 |
| JP | 2004130109 | 4/2004 |
| JP | 5379966 | 12/2013 |
| KR | 20180108949 | 10/2018 |
| WO | 2005048851 | 6/2005 |
| WO | 2010122034 | 10/2010 |
| WO | 2017164862 | 9/2017 |
| WO | 2019063807 | 4/2019 |
| WO | 2019091537 | 5/2019 |
| WO | 2019213122 | 11/2019 |
| WO | 2020123295 | 6/2020 |
| WO | 2020123899 | 6/2020 |
| WO | 2020123899 A1 | 6/2020 |
| WO | 2020124047 | 6/2020 |
| WO | 2020124052 | 6/2020 |
| WO | 2020124056 A1 | 6/2020 |

OTHER PUBLICATIONS

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

International Search Report and Written Opinion of the International Searching Authority for PCT/US2019/066409, Feb. 10, 2020, 20 pages. Feb. 10, 2020.

Non-Final Office Action issued in U.S. Appl. No. 17/345,135, Dec. 9, 2021, 16 pages. Dec. 9, 2021.

Non-Final Office Action issued in U.S. Appl. No. 17/345,137, Nov. 15, 2021, 14 pages. Nov. 15, 2021.

Non-Final Office Action issued in U.S. Appl. No. 17/345,402, Feb. 1, 2022, 17 pages. Feb. 1, 2022.

* cited by examiner

RESECTION GUIDES, SWEEPING REAMERS, AND METHODS FOR USE IN TOTAL ANKLE REPLACEMENT

CROSS REFERENCE TO RELATED APPLICATIONS

This application is a continuation of U.S. patent application Ser. No. 17/345,398 filed Jun. 11, 2021 which is a continuation of International Patent Application No. PCT/US2019/064948, filed on Dec. 6, 2019, entitled "Resection Guides, Sweeping Reamers, And Methods For Use In Total Ankle Replacement", which international patent application claims priority benefit under 35 U.S.C. § 119(e) to U.S. Provisional Patent Application No. 62/898,615, filed Sep. 11, 2019, entitled "Resection Guides, Sweeping Reamers, And Methods For Use In Total Ankle Replacement", and which international patent application claims priority benefit under 35 U.S.C. § 119(e) to U.S. Provisional Patent Application No. 62/779,436, filed Dec. 13, 2018, entitled "Joint Replacement Systems And Methods Of Use And Assembly", which applications are hereby incorporated herein by reference in their entireties.

TECHNICAL FIELD

The present disclosure relates generally to general, podiatric, and orthopaedic surgery related to joint deformities. More specifically, but not exclusively, the present disclosure relates to resection guides and methods for use in total ankle replacement.

BACKGROUND

Total ankle replacement (TAR), or ankle arthroplasty, is a surgical procedure to replace deformed and/or damaged articular surfaces of the human ankle joint with a prosthetic joint while preserving the functional range of motion (ROM) of the ankle joint.

Typical TAR prosthesis include a tibial component, a talus component, and a bearing or insert component positioned between the tibial and talus prosthesis components.

Achieving a stable replacement ankle joint that provides for full articulation/motion (e.g., achieving a range of motion of a typical "healthy" ankle joint) generally requires proper sizing and positioning/orientating/aligning of the tibial component with respect to the distal end of a tibia, of the talus component with respect to the proximal end of a talus, and of the insert or spacer therebetween.

SUMMARY

Shortcomings of the prior art are overcome and additional advantages are provided through the provision of a resection guide for use in resecting at least a portion of an anatomical structure of a patient. The resection guide may include, for example, a body having a first side and an opposite second side. The body includes a plurality of alignment pin through-holes extending from the first side to the second side of the body with openings on the first side of the body and openings on the second side of the body. The body includes a plurality of guide through-holes extending from the first side to the second side to define a first pattern of guide through-holes with openings on the first side of the body and openings on the second side of the body. When the plurality of alignment pin through-holes of the body is supported on a plurality of alignment pins attached to the anatomical structure of the patient, the openings of the guide through-holes on the second side of the body face the anatomical structure and the openings of the guide through-holes on the first side face away from the anatomical structure so that the first pattern of guide through-holes is operable for receiving a drill for use in resecting the at least a portion of the anatomical structure of the patient.

In another embodiment, the resection guide may further include a second resection guide having a body having a first side and an opposite second side. The body includes a plurality of alignment pin through-holes extending from the first side to the second side of the body with openings on the first side of the body and openings on the second side of the body. The alignment pin through-holes of the second resection guide match the pattern of alignment pin through-holes of the first resection guide described above. The body has a plurality of guide through-holes extending from the first side to the second side to define a second pattern of guide through-holes with openings on the first side of the body and openings on the second side of the body. The second pattern of guide through-holes being different from the first pattern of guide through-holes of the first resection guide. When the plurality of alignment pin through-holes of the body is supported on a plurality of pins attached to the anatomical structure of the patient, the openings of the guide through-holes on the second side of the body face the anatomical structure and the openings of the guide through-holes on the first side face away from the anatomical structure so that the second pattern of guide through-holes is operable for receiving a drill for use in resecting a second portion of the anatomical structure of the patient. In some embodiments, the second pattern of guide through-holes of the second resection guide relative to the plurality of alignment holes is offset from and overlapping with the first pattern of guide through-holes of the first resection guide relative to the plurality of alignment holes.

In another embodiment, a sweeping reamer having a body and a reamer. The body includes a first side and a second side, and a plurality of alignment pin through-holes extending from the first side to the second side of the body with openings on the first side of the body and openings on the second side of the body. The body includes an elongated opening extending from the first side to the second side to define an elongated opening on the first side of the body and an elongated opening on the second side of the body. The reamer is extendable through the elongated opening of the body. In some embodiments, the body includes a T-shaped slot aligned with the elongated opening, and a reamer guide attachable to the reamer, which reamer guide is slidably receivable in said T-shaped slot.

In another embodiment, a surgical method includes, for example, supporting a first resection guide on a plurality of alignment pins attached to an anatomical structure of a patient with the resection guide having a first pattern of guide through-holes, guiding a drill through the plurality of guide through-holes in the first resection guide and into at least a portion of the anatomical structure of the patient to form a pattern of spaced apart holes in the anatomical structure. In another embodiment, the method may further include removing the resection guide from the plurality of alignment pins attached to the anatomical structure of the patient, supporting a second resection guide on the plurality of alignment pins attached to the anatomical structure of the patient with the second resection guide having a second pattern of guide through-holes offset from the first pattern, and guiding a drill through the plurality of guide through-holes in the second resection guide and into at least a portion of the anatomical structure of the patient.

In another embodiment, a decoupled resection guide includes, for example, a first body portion having a first side and an opposite second side. The first body portion includes a plurality of alignment pin through-holes extending from the first side to the second side of the first body. A second body portion includes a first side and an opposite second side. The second body portion includes a plurality of fixation pin through-holes extending from the first side to the second side of the second body portion. The second body portion includes at least one guide aperture. A plurality of connecting pins are operable for movably connecting the first body portion relative to the second body portion. The plurality of alignment pin through-holes of the first body portion is supportable on a plurality of alignment pins attached to a first anatomical structure of the patient. The first body portion and the second body portion are operable to separate joint surfaces between the first anatomical structure of the patient and a second anatomical of the patient. The fixation pin through-holes of the second body portion are operable for inserting a plurality of pins therethrough and into the second anatomical structure of the patient. The at least one guide aperture is operable for guiding a cutting tool for use in resecting a portion of the second anatomical structure of the patient. In some embodiments, the second body portion includes a paddle extending from the second side of the second body portion. In other embodiments, two paddles are movably supported on the connecting pins.

In another embodiment, a surgical method includes, for example, supporting a decoupled resection guide on a plurality of alignment pins attached to an anatomical structure of a patient, inserting at least one spacer between portions of the decoupled resection guide to operably spread apart anatomical structures of the patient, and guiding a cutting tool through an aperture in the decoupled resection guide to form a cut in the anatomical structure.

Additional features are realized through the techniques of the present disclosure. Other embodiments and aspects of the present disclosure are described in detail herein and are considered a part of the claimed disclosure.

These and other objects, features and advantages of this disclosure will become apparent from the following detailed description of the various aspects of the disclosure taken in conjunction with the accompanying drawings.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

DETAILED DESCRIPTION

Figure 1:
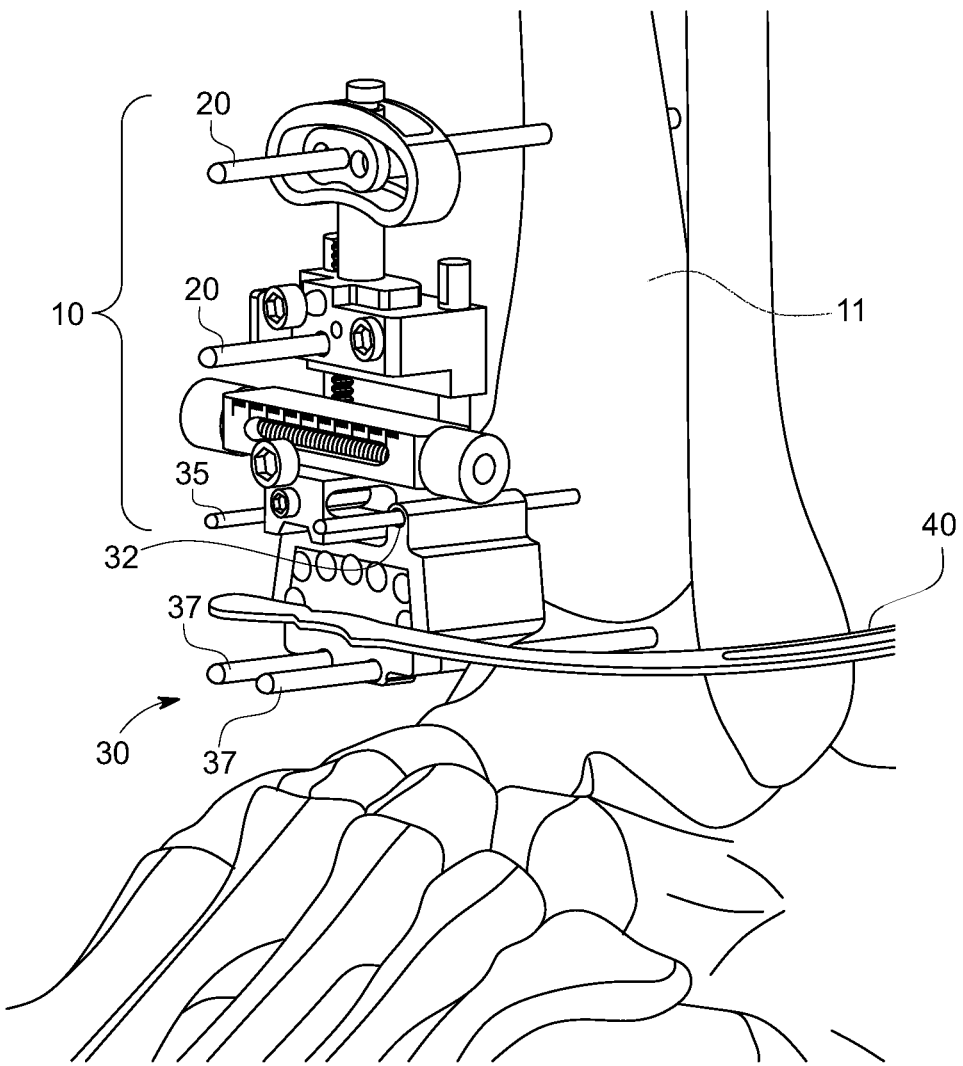
FIG. 1 is a perspective view of a portion of an alignment system, sizing template, and wing member, according to an embodiment of the present disclosure.

Generally stated, disclosed herein are resection guides, sweeping reamers, and decoupled resection guides, and methods for resurfacing joint surfaces such as for total ankle replacement. The instruments, guides, systems and related methods may facilitate preparation of a tibia and/or talus of a patient for implantation of a total ankle replacement prosthesis therein. The instruments, guides, systems and related methods may also facilitate selection of a particular size of a tibial component, a talus component and/or a tibial insert or spacer of the total replacement ankle prosthesis that suits the patient.

In this detailed description and the following claims, the words proximal, distal, anterior or plantar, posterior or dorsal, medial, lateral, superior and inferior are defined by their standard usage for indicating a particular part or portion of a bone, joint (or any other anatomical structure) or implant according to the relative disposition of the natural bone, joint (or any other anatomical structure) or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot and/or ankle, the term "dorsal" refers to the top of the foot and the term "plantar" refers the bottom of the foot.

Similarly, positions or directions may be used herein with reference to anatomical structures or surfaces. For example, as the current instruments, guides, systems and related methods (and components thereof) are described herein with reference to use with the bones of the ankle, the bones of the foot, ankle and lower leg may be used to describe the surfaces, positions, directions or orientations of the instruments, guides, systems and related methods (and components thereof). Further, the instruments, guides, systems and related methods, and the aspects, components, features and the like thereof, disclosed herein may be described with respect to one side of the body (e.g., the left or right ankle) for brevity purposes. However, as the human body is relatively symmetrical or mirrored about a line of symmetry (midline), it is hereby expressly contemplated that the instruments, guides, systems and related methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the instruments, guides, systems and related methods, and the aspects, components, features and the like thereof, described herein with respect to the right ankle of a patient may be mirrored so that they likewise function with the left ankle of the patient. Further, the instruments, guides, systems and related methods, and the aspects, components, features and the like thereof, disclosed herein are described with respect to the ankle for brevity purposes, but it should be understood that the instruments, guides, systems and related methods (and components thereof) may be used with other joints of a human body (or other mammalian body) having similar structures.

Figure 2:
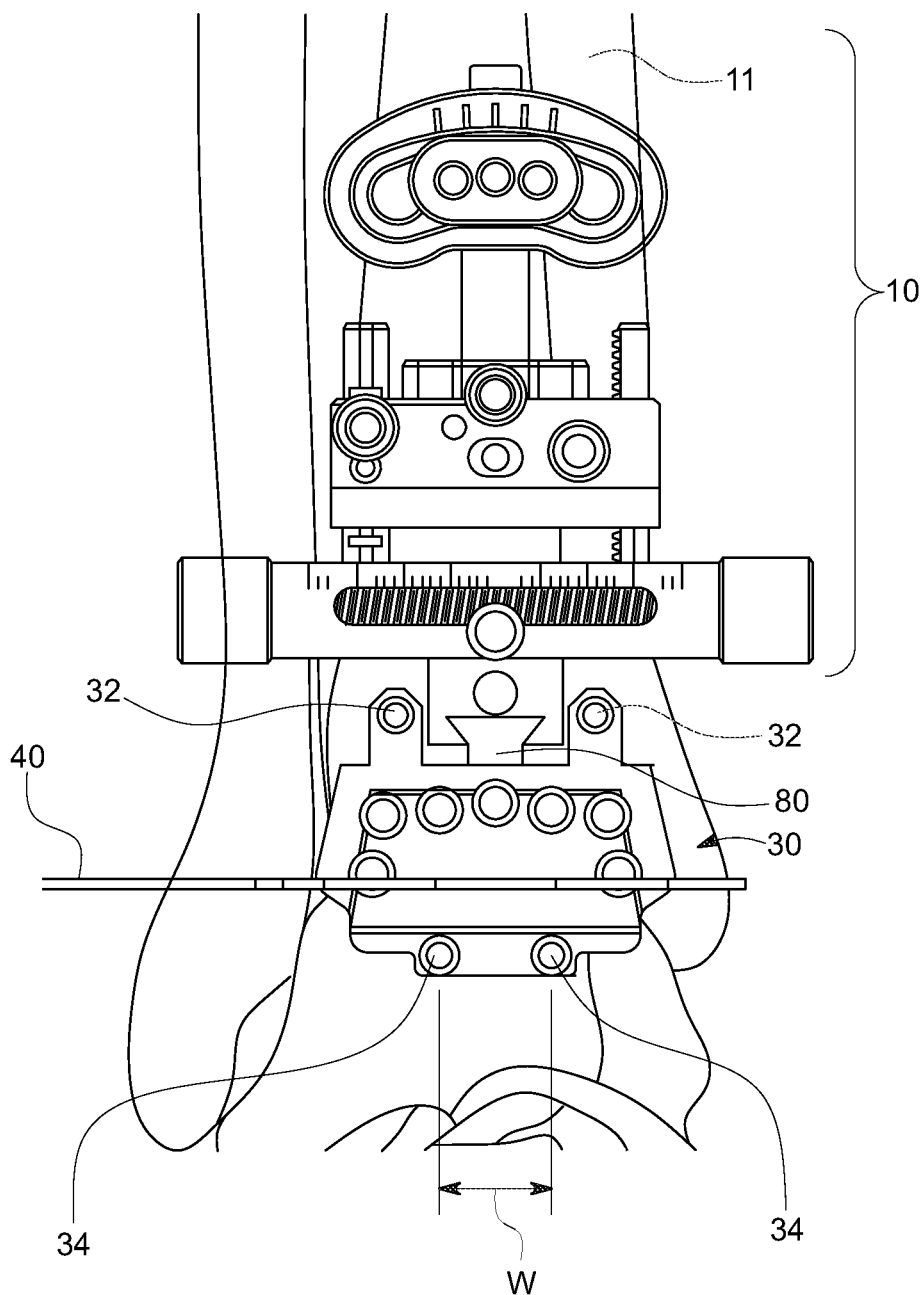
FIG. 2 is an elevational view of the portion of the alignment system, sizing template, and wing member, according to an embodiment of the present disclosure.
Figure 55:
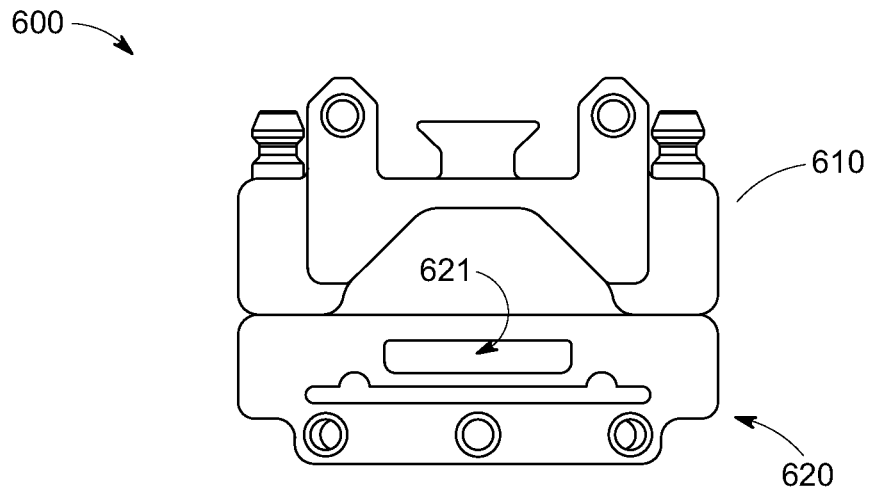
FIG. 55 is a front view of a decoupled resection guide having a viewing window, according to an embodiment of the present disclosure.
Figure 56:
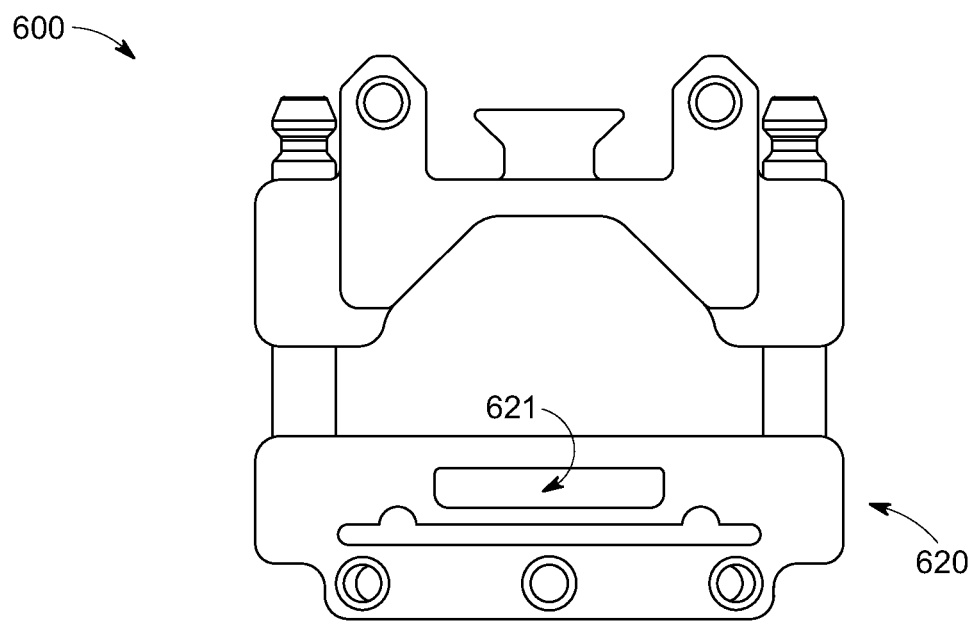
FIG. 56 is a front view of a decoupled resection guide having a viewing window of FIG. 55 in a distracted configuration, according to an embodiment of the present disclosure.

Referring to the drawings, like reference numerals are used to indicate like or analogous components throughout the several views, FIGS. 1 and 2 illustrate a portion of an alignment system 10 operably attached to a patient for use in connection with the resection guides, sweeping reamers, and decoupled resection guides of the present disclosure. FIGS. 3-10 and 11-18 illustrate resection guides 100 and 200 that are operable sequentially for use in resecting a distal portion of the tibia and a superior portion of the talus, FIGS. 25-32 illustrate a sweeping reamer 300 for use in cleaning up a resected distal portion of the tibia, and FIGS. 35-42 illustrate a resection guide 400 that is operable for use in resecting a distal portion of the tibia and a superior portion of the talus. Resection guides 200 and 400 include guides for the tibial resection and the talus resection that are fixed in place relative to each other, e.g., coupled. FIGS. 43-54 illustrate a decoupled talar resection guide 500, FIGS. 55 and 56 illustrate a decoupled talar resection guide 600 with a viewing window, and FIGS. 57-66 illustrate a decoupled talar resection guide 700.

With reference again to FIGS. 1 and 2, the portion of the alignment system 10 may be affixed or coupled to anatomical configuration/structures of a patient, e.g., a tibia 11 of an ankle joint, via a pin, k-wire or other like fixation members 20 (FIG. 1). A sizing template 30 may be operably attached to the alignment system 10 and positioned at a distal tibia when the alignment system 10 is utilized to prepare a tibia and/or talus for an ankle arthroplasty. The alignment system 10 may include a planar wing member 40 that is removably coupled within a slot (not shown) of the sizing template 30. For example, the wing member 40 may include a tang, tab or projection portion that is configured to removably, but securely, fit within the slot of the sizing template 30. In this way, the wing member 40 can be used as another reference guide to align the sizing template 30 (and the alignment system 10 as a whole) to the anatomical configuration/structures of the patient (e.g., to the alignment axis (e.g., an anatomical or mechanical axis) of anatomical structures of interest).

For example, the sizing template is intended to be a sizing and an alignment tool for the surgeon prior to resecting bone. The sizing template may be formed from a plastic or polymeric material that includes radiopaque members or portions (e.g., externally-visible indications and/or radiopaque indications) that allow a surgeon to determine/evaluate the orientation of the sizing template (and/or one or more resections formed via the sizing template) with respect to the anatomical configuration/structures of the patient under x-ray and/or fluoroscopy. A plurality of different sized sizing templates may be provided to also allow a surgeon to determine/evaluate the size of the sizing template (and/or one or more resections formed via the sizing template) with respect to the anatomical configuration/structures of the patient. The width W (FIG. 2) of the inferior portion of the sizing template may represents a respective talus size.

A coupler 80 (FIG. 2) may be attached to the sizing template 30 for connecting the sizing template 30 to the alignment system 10. For example, the coupler 80 may be a flaring tenon that slides into a mortise in the alignment system 10, e.g., forming a dovetail joint. The sizing template 30 may include a plurality of alignment pin through-holes 32 (FIG. 2), which extend through the sizing template 30, for receiving pins, k-wires or other like fixation members 35 (one of which is shown in FIG. 1), and which are attached to the tibia of the patient. The sizing template 30 may also include a plurality of alignment pin through-holes 34 (FIG. 2), which extend through sizing template 30, for receiving pins, k-wires or other like fixation members 37 (FIG. 1), and which are attached in the patient's tibia. Suitable alignment systems and sizing templates are described in international patent application PCT/US2019/029978, filed May 1, 2019, and entitled "Laser-Based Implant Alignment And Resection Guide Systems And Related Methods," the entire contents being incorporated in herein by reference. As described in greater detail below, after installation of the alignment pins, the sizing template 30 is removed, and the resection guides, sweeping reamer, and decoupled resection guides of the present disclosure are slid onto the pins attached to the patient's tibia and/or talus.

FIGS. 3-10 and 11-18 illustrates resection guides 100 and 200, respectively, which are operable sequentially for use in resecting a distal portion of the tibia and a superior portion of the talus, according to an embodiment of the present disclosure. Exemplary resection guides 100 and 200 are operable for use with a plurality of alignment pins fixedly attached to a patient for resecting at least a portion of an anatomical structure of interest. As described in greater detail below, for example, the resection guides 100 and 200 may include offset and overlapping patterns of guide through-holes for use with a drill in forming a tibia arc resection of a patient's distal tibia for use in a total ankle repair. In these illustrated embodiments, resection guide 200 may also be a coupled tibial and talar resection guide for use in also resecting a patient's talus for use in a total ankle repair. In other embodiments, for example, the resection guide 100 may be configured to also guide a cutting tool for use in forming a talar resection of the patient's talus for use in, for example, a total ankle repair. The resection guides 100 and 200 may be configured in a plurality of different matching size arcs to allow a surgeon to selectively choose the correct sized pair of resection guides based on the anatomical configuration of a patient specific tibia and talus such as, for example, selected corresponding to the selected sizing template 30 (FIG. 1) for initially aligning the alignment pins.

Figure 3:
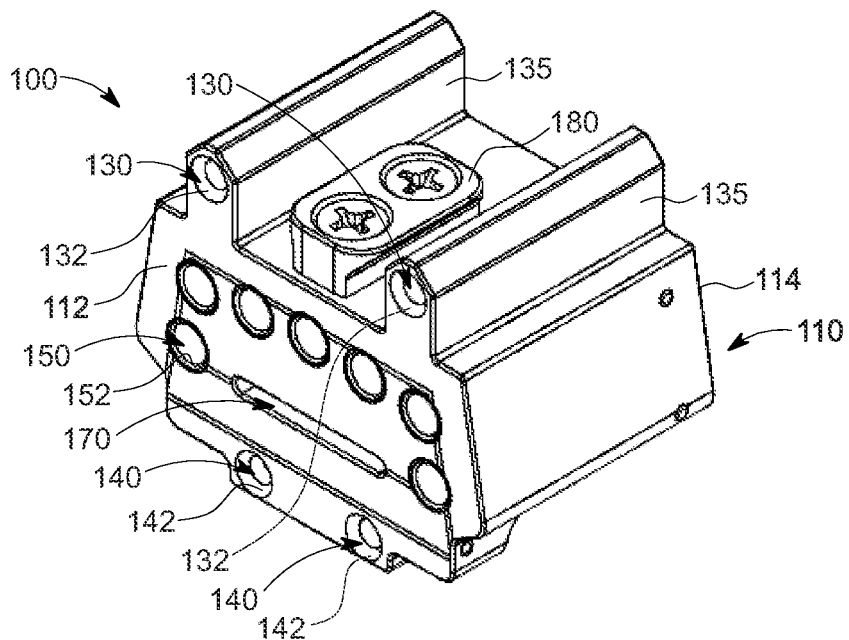
FIG. 3 is a top perspective view of a resection guide, according to an embodiment of the present disclosure.
Figure 4:
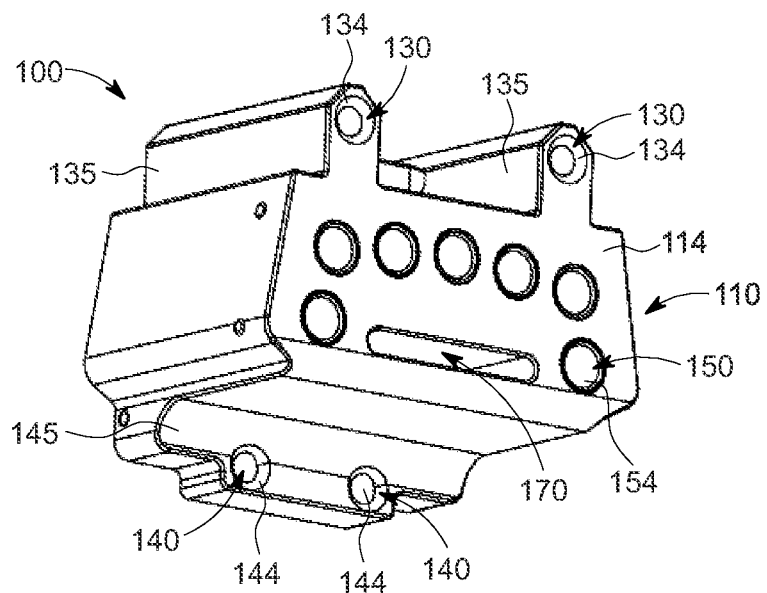
FIG. 4 is a bottom perspective view of the resection guide of FIG. 3, according to an embodiment of the present disclosure.
Figure 5:
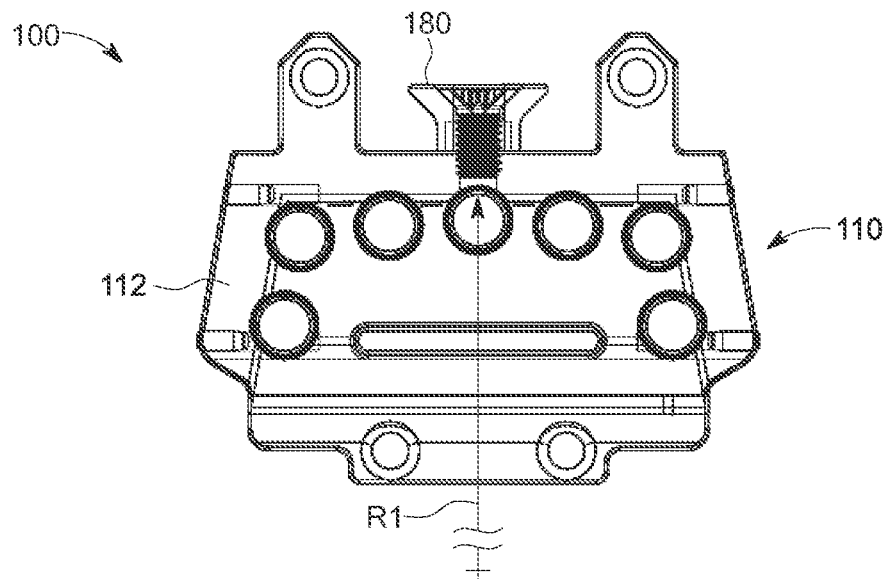
FIG. 5 is a front view of the resection guide of FIG. 3, according to an embodiment of the present disclosure.
Figure 6:
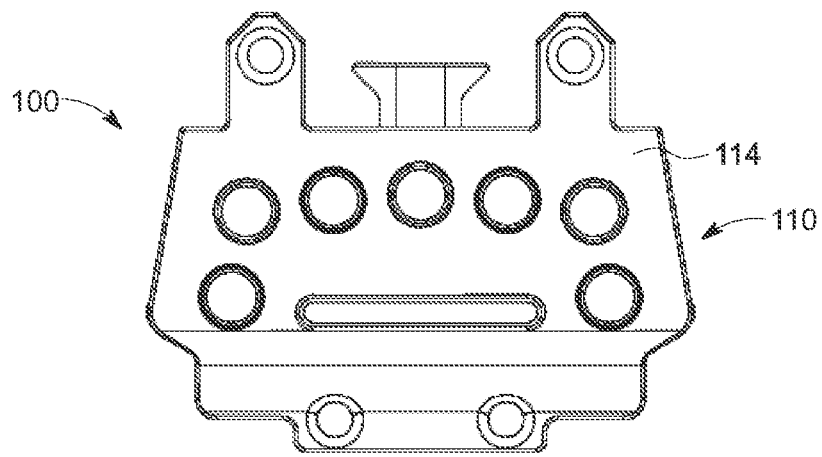
FIG. 6 is a rear view of the resection guide of FIG. 3, according to an embodiment of the present disclosure.
Figure 7:
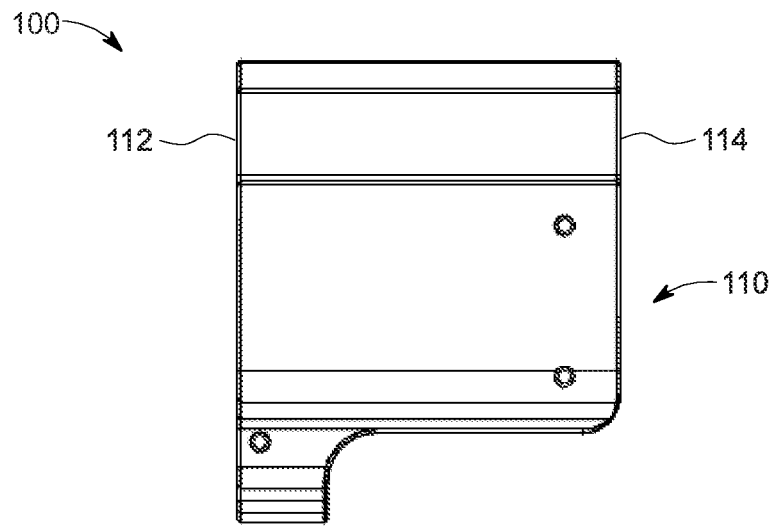
FIG. 7 is a right side view of the resection guide of FIG. 3, according to an embodiment of the present disclosure.
Figure 8:
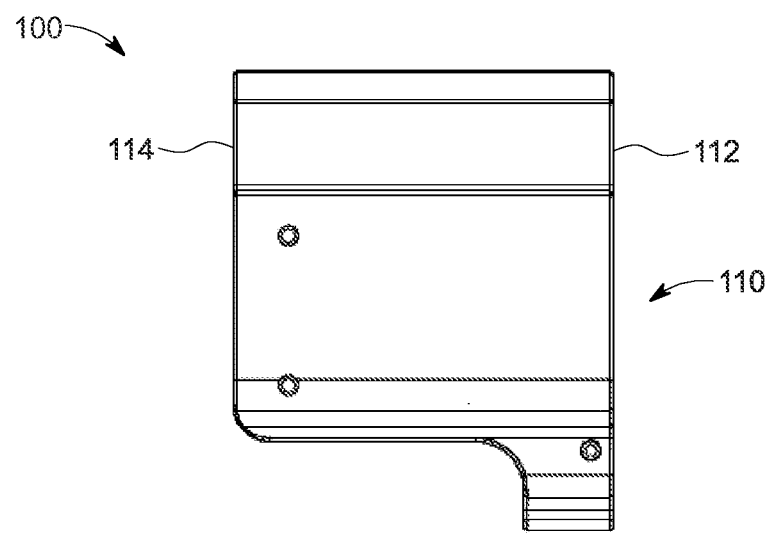
FIG. 8 is a left side view of the resection guide of FIG. 3, according to an embodiment of the present disclosure.
Figure 9:
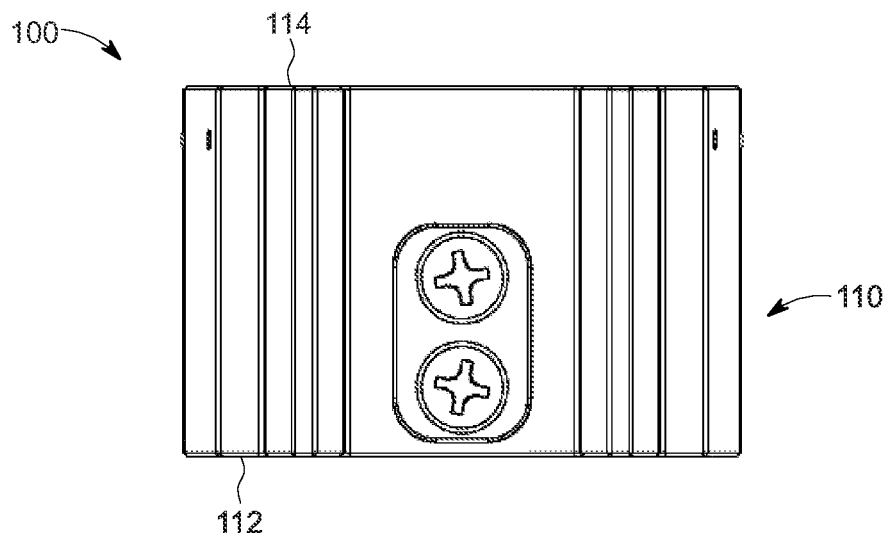
FIG. 9 is a top view of the resection guide of FIG. 3, according to an embodiment of the present disclosure.
Figure 10:
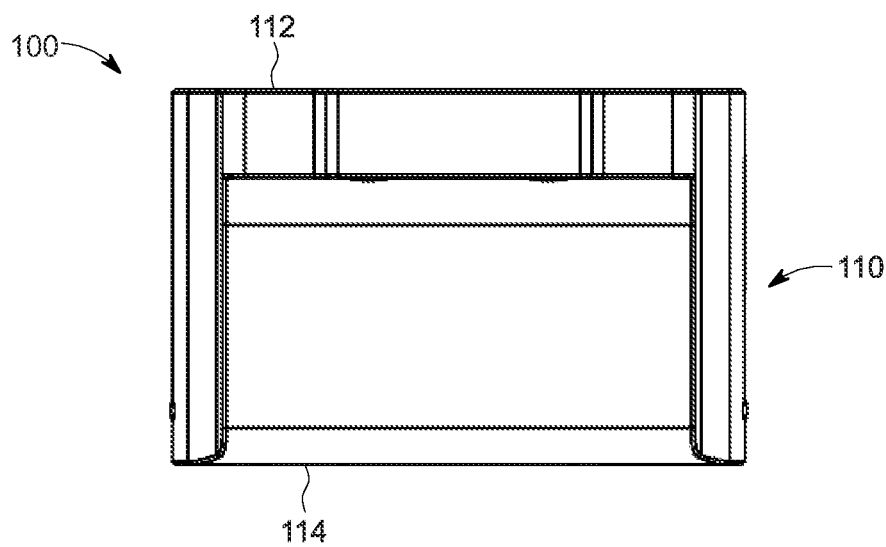
FIG. 10 is a bottom view of the resection guide of FIG. 3, according to an embodiment of the present disclosure.

As shown in FIGS. 3-10, the resection guide 100 may include a body 110 having a first side 112 and an opposite second side 114. With reference to FIGS. 3 and 4, the body 110 includes a plurality of alignment pin through-holes 130 and 140. For example, the plurality of tibia alignment pin through-holes 130 extend from the first side to the second side of the body with openings 132 opening onto the first side of the body and openings 134 opening onto the second side of the body. The plurality of talar alignment pin through-holes 140 extend from the first side to the second side of the body with openings 142 opening onto the first side of the body and openings 144 opening onto the second side of the body.

The body 110 also includes a plurality of guide through-holes 150 extending from the first side to the second side to define a first pattern of guide through-holes 150 with openings 152 opening onto the first side of the body and openings 154 opening onto the second side of the body. The plurality of alignment pin through-holes 130 and 140 and the plurality of guide through-holes 150 may be parallel to each other. The plurality of alignment pin through-holes 130 and 140 may include four alignment pin through-holes. For example, two alignment pin through-holes 130 may be disposed in superior-extending tabs 135 extending from body 110, and two alignment pin through-holes 140 disposed along an inferior-extending tab 145 of the body 110.

The plurality of guide through-holes 150 may be disposed between the plurality of alignment pin through-holes 130 and the plurality of alignment pin through-holes 140. The plurality of guide through-holes 150 may define a linear arrangement of guide through-holes such as a linear arrangement of guide through-holes in an inverted arcuate pattern or inverted U-shaped pattern. The plurality of guide through-holes 150 may be a series of seven generally evenly spaced apart holes. The body may be formed from a metallic material or other suitable biocompatible material. In some embodiments, the body may be a monolithic structure or a one-piece structure. In other embodiments, the body may be formed from a biocompatible polymeric material and include metal bushings that define the guide through-holes. The body 110 may further include a slot 170 for removably receiving a portion of wing member 40 (FIGS. 1 and 2) of the alignment system 10 (FIG. 1). The slot may be a through slot that extends from the first side to the second side.

A coupler 180 (FIGS. 3 and 5) may be attached to the body for connecting the body to the alignment system 10 (FIG. 1). For example, the coupler 180 may be a flaring tenon that slides into a mortise in the alignment system 10 (FIG. 1), e.g., forming a dovetail joint.

In some embodiments, the alignment pin through-holes may be 2.4 millimeter diameter drill holes, and the guide through-holes may be 3.5 mm drill holes. It will be appreciated that other suitable sized holes may be employed. The resection guide may be sized to have an arc resection having a radius R1 (FIG. 5) of about 50 mm, about 100 mm, about 150 mm, or other suitable radius. The corner drill radius may be about 1.75 mm to reduce risk of bone fracture.

Figure 11:
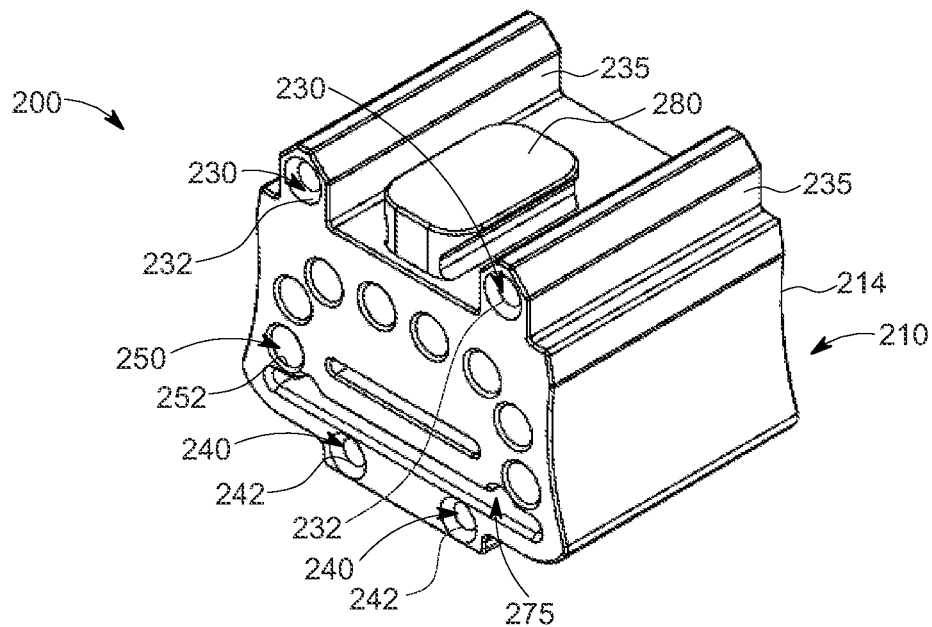
FIG. 11 is a top perspective view of a second resection guide, according to an embodiment of the present disclosure.
Figure 12:
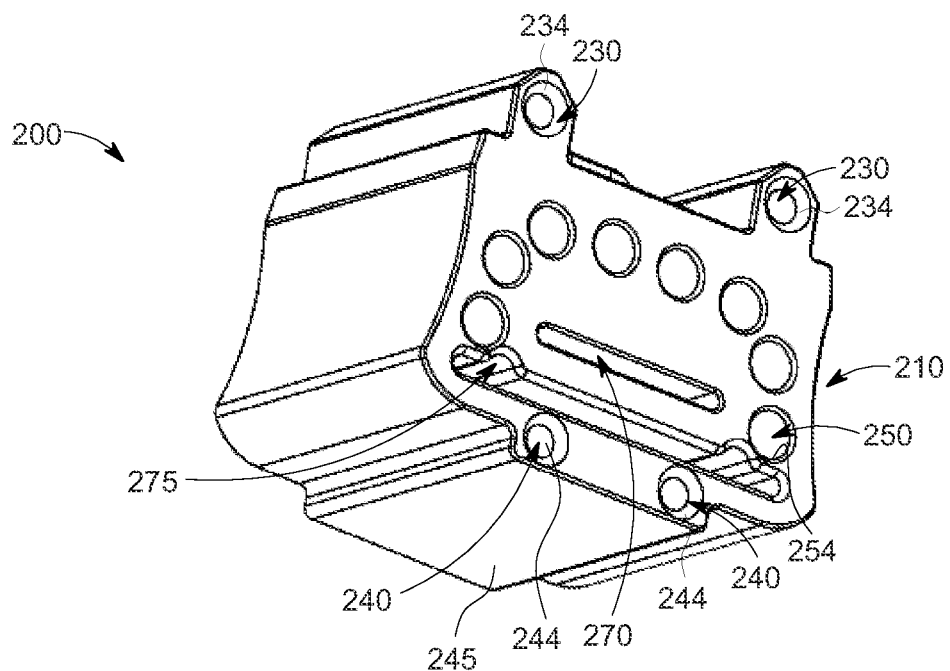
FIG. 12 is a bottom perspective view of the resection guide of FIG. 11, according to an embodiment of the present disclosure.
Figure 13:
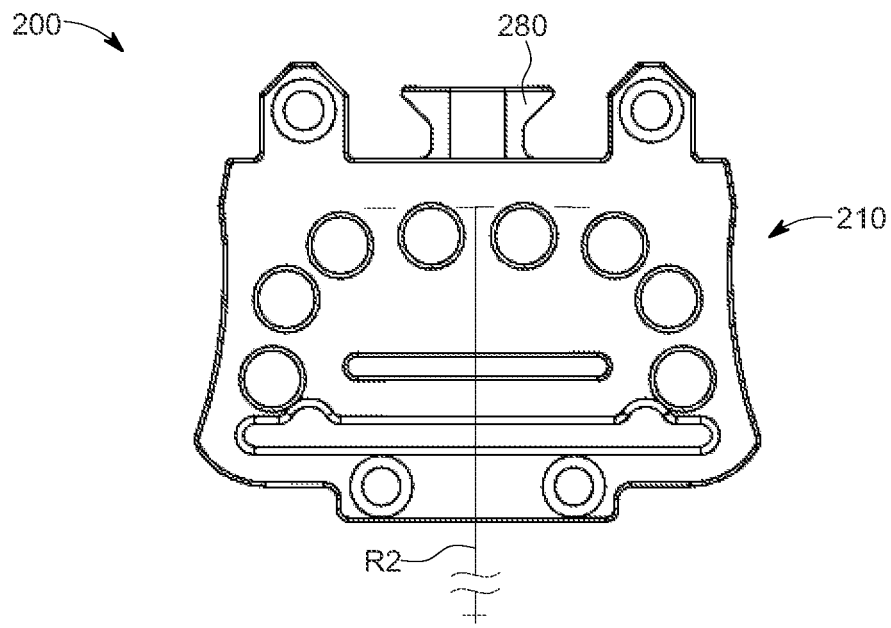
FIG. 13 is a front view of the resection guide of FIG. 11, according to an embodiment of the present disclosure.
Figure 14:
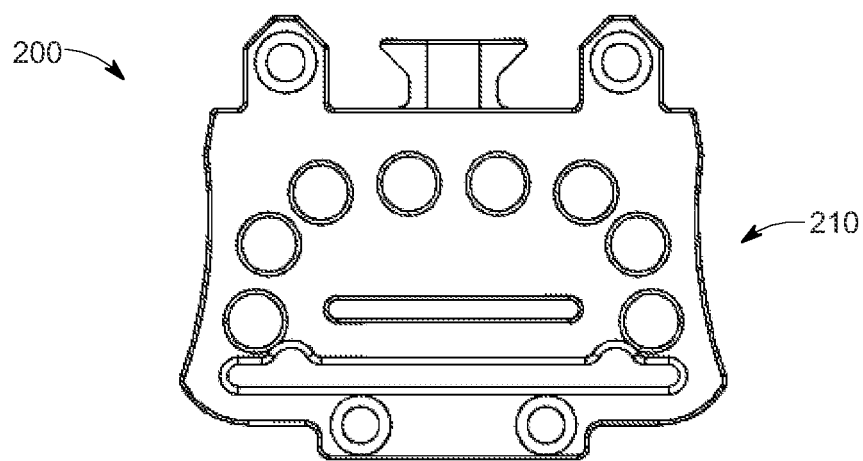
FIG. 14 is a rear view of the resection guide of FIG. 11, according to an embodiment of the present disclosure.
Figure 15:
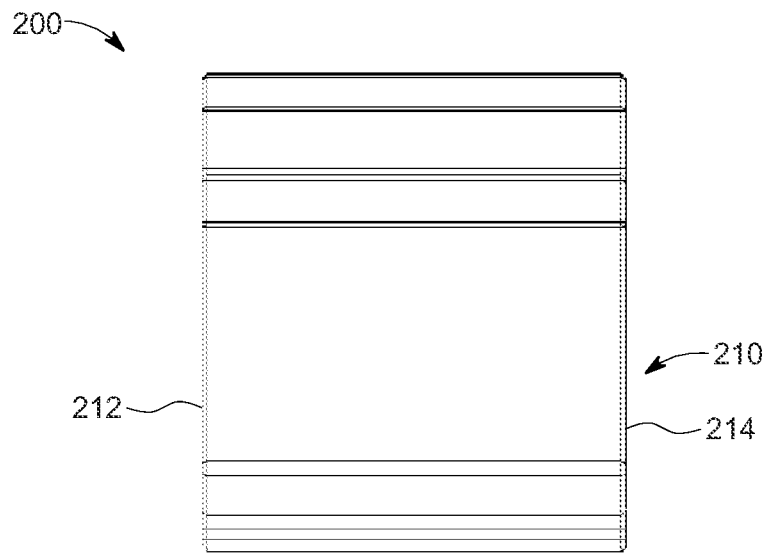
FIG. 15 is a right side view of the resection guide of FIG. 11, according to an embodiment of the present disclosure.
Figure 16:
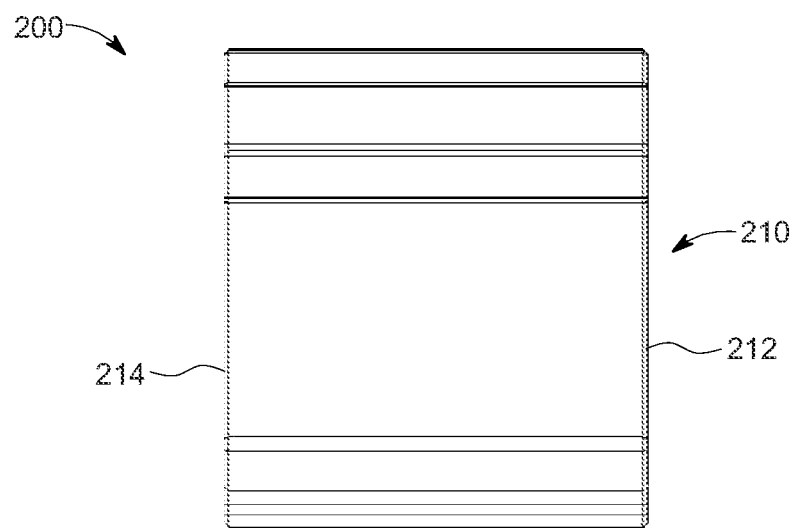
FIG. 16 is a left side view of the resection guide of FIG. 11, according to an embodiment of the present disclosure.
Figure 17:
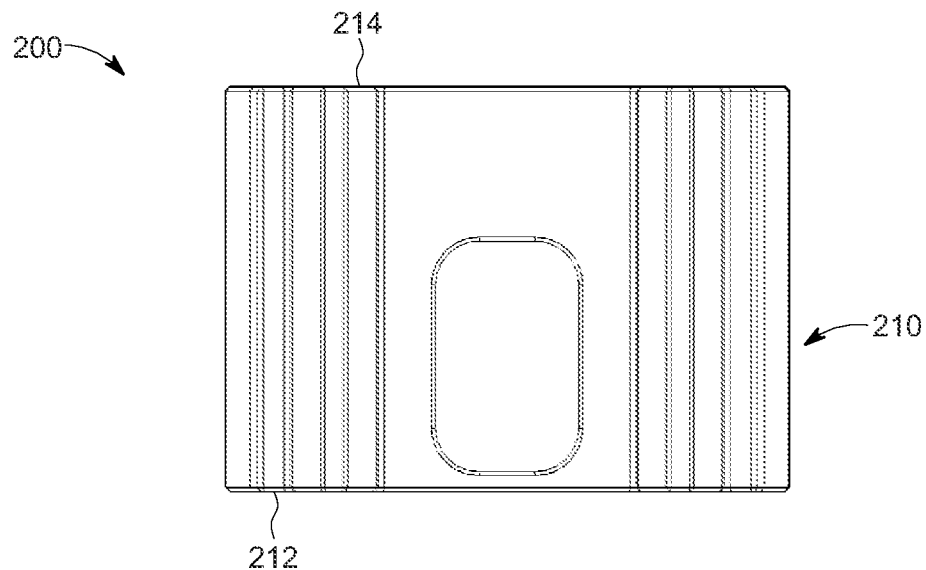
FIG. 17 is a top view of the resection guide of FIG. 11, according to an embodiment of the present disclosure.
Figure 18:
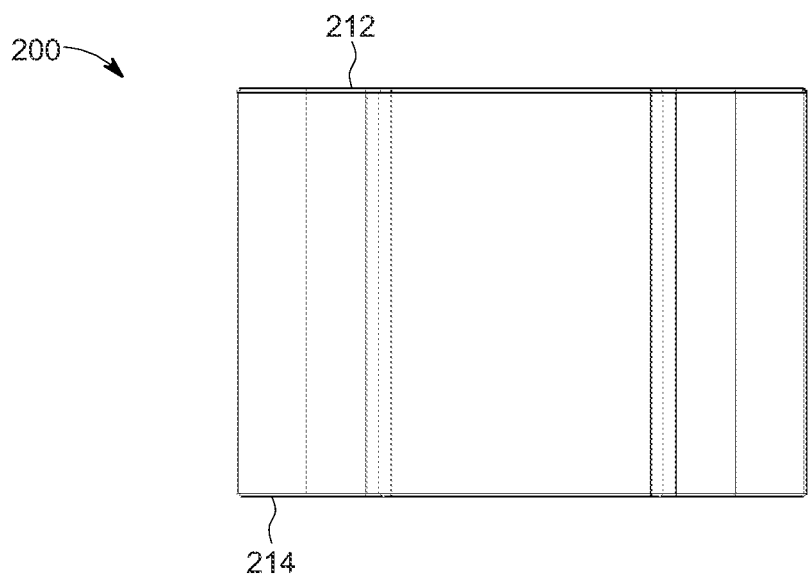
FIG. 18 is a bottom view of the resection guide of FIG. 11, according to an embodiment of the present disclosure.

With reference to FIGS. 11-18, the second resection guide 200 may include a body 210 having a first side 212 and an opposite second side 214. With reference to FIGS. 11 and 12, the body 210 includes a plurality of alignment pin through-holes 230 and 240. For example, the plurality of tibia alignment pin through-holes 230 extend from the first side to the second side of the body with openings 232 opening onto the first side of the body and openings 234 opening onto the second side of the body. The plurality of talar alignment pin through-holes 240 extend from the first side to the second side of the body with openings 242 opening onto the first side of the body and openings 244 opening onto the second side of the body.

The body 210 also includes a plurality of guide through-holes 250 extending from the first side to the second side to define a second pattern of guide through-holes 250 with openings 252 opening onto the first side of the body and openings 254 opening onto the second side of the body. The plurality of alignment pin through-holes 230 and 240 and the plurality of guide through-holes 250 may be parallel to each other. The plurality of alignment pin through-holes 230 and 240 may include four alignment pin through-holes. For example, two alignment pin through-holes 230 may be disposed in superior-extending tabs 235 extending from body 210, and two alignment pin through-holes 240 disposed along an inferior-extending tab 245 of the body 210.

The plurality of guide through-holes 250 may be disposed between the plurality of alignment pin through-holes 230 and the plurality of alignment pin through-holes 240. The plurality of guide through-holes 250 may define a linear arrangement of guide through-holes such as a linear arrangement of guide through-holes in an inverted arcuate or inverted U-shaped pattern. The plurality of guide through-holes 250 may be a series of eight generally evenly spaced apart holes. The body may be formed from a metallic material or other suitable biocompatible material. In some embodiments, the body may be a monolithic structure or a one-piece structure. In other embodiments, the body may be formed from a biocompatible polymeric material and include metal bushings that define the guide through-holes. The body 210 may further include a slot 270 for removably receiving a portion of wing member 40 (FIGS. 1 and 2) of the alignment system 10 (FIG. 1). The slot may be a through slot that extends from the first side to the second side.

Resection guide 200 may also be operable for guiding a cutting tool for use in forming a resection of the patient's talus for total ankle repair. For example, an elongated guide slot 275 may be disposed below the slot 270.

A coupler 280 (FIGS. 11 and 13) may be attached to the body for connecting the body to the alignment system 10 (FIG. 1). For example, the coupler 280 may be a flaring tenon that slides into a mortise in the alignment system 10 (FIG. 1), e.g., forming a dovetail joint.

In some embodiments, the alignment pin through-holes may be 2.4 millimeter diameter drill holes, and the guide through-holes may be 3.5 mm drill holes. It will be appreciated that other suitable sized holes may be employed. The resection guide may be sized to have an arc resection having a radius R2 (FIG. 13) of about 50 mm, about 100 mm, about 150 mm, or other suitable radius. The corner drill radius may be about 1.75 mm to reduce risk of bone fracture. Desirably, the diameters of the alignment pin through-holes for the first resection guide 100 and the second resection guide 200 are the same, and the diameters of the guide through-holes for the first resection guide 100 and the second resection guide 200 are the same. The number of guide through-holes may vary in number with the size of the resection guide as the width of the resection guide increases. In some embodiments, the first resection guide may include N−1 guide through-holes and the second resection guide may include N guide through holes.

With reference again to FIG. 1, initially a surgeon may use the sizing template 30 to locate the position of anatomical cuts in 5 degrees of freedom (i.e., 1—Medial and lateral position; 2—Proximal and distal position; 3—Varus and Valgus position; 4—Slope of cut (with aid from alignment wing); and 5—internal and external rotation (with aid of drill placed in bushing)) as well as determine the size of a resection. For example, the sizing template may include radiopaque bushings that are visible while viewing through an X-ray or fluoroscopy. The outer tangency of the guide holes in the sizing bushing represent the size of the resection and the corresponding arced tibia implant. The width W (FIG. 2) of the sizing template at the region of the most distal pin may also represent the respective talar size. After selecting and positioning the desired sizing template, installing the pins 35 and pins 37, the sizing template 30 is removed.

Figure 19:
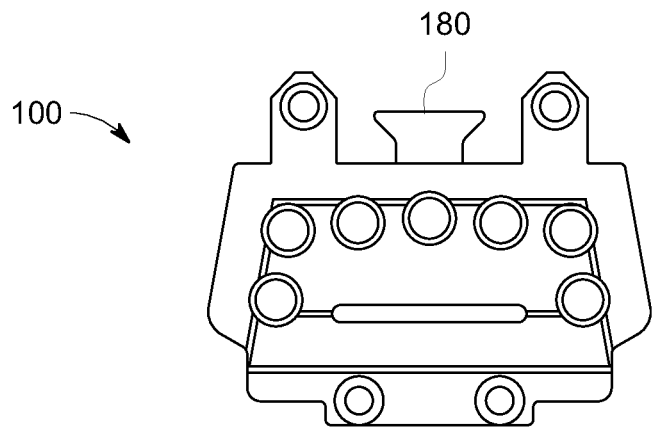
FIG. 19-21 are front views of the resection guide of FIG. 3, the resection guide of FIG. 11, and superimposed front views of the resection guide of FIG. 3 and the resection guide of FIG. 11, according to an embodiment of the present disclosure.
Figure 22:
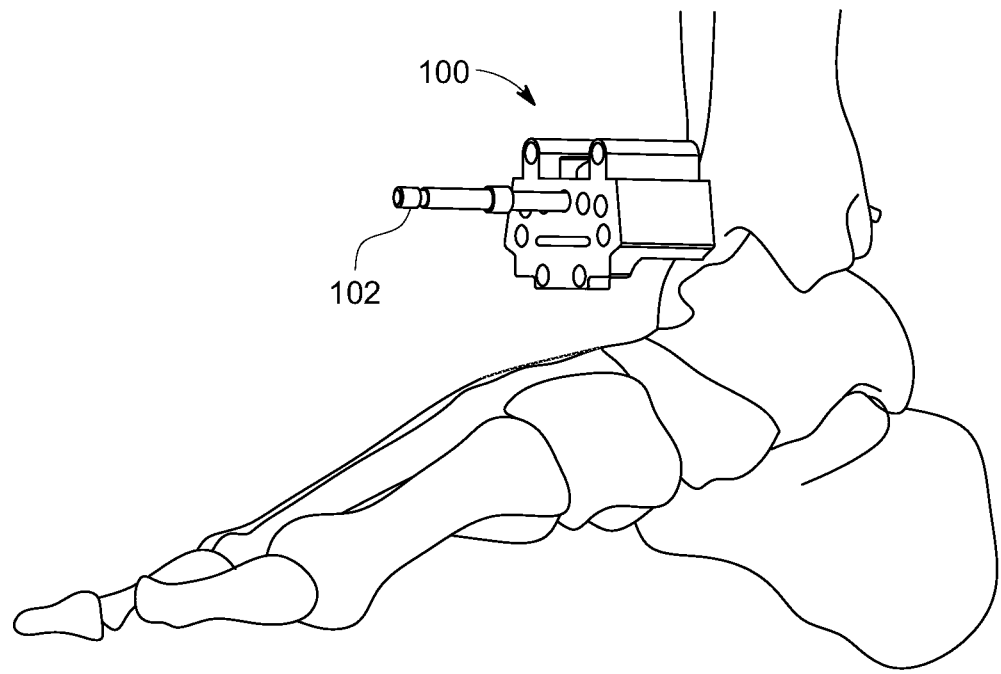
FIG. 22 is a perspective view of the resection guide of FIG. 3 and a drill for forming a portion of a tibial resection, according to an embodiment of the present disclosure.

As shown in FIGS. 19 and 22, the resection guide 100 may be employed and aligned and positioned on a plurality of pins or guide wires 35 (FIG. 1) attached to a distal portion of a tibia of a patient and aligned and positioned on a plurality of pins or guide wires 37 (FIG. 1) attached to a talus of the patient. If the alignment system 10 is also attached to the tibia of the patient, the resection guide 100 may also be operably attached to the alignment system via the coupler 180 (FIG. 19). Using a drill 102 (FIG. 22), a surgeon may initially form a series of holes in the tibia to initiate a resection of the distal portion of the tibia. Thereafter, the resection guide 100 is removed.

Figure 20:
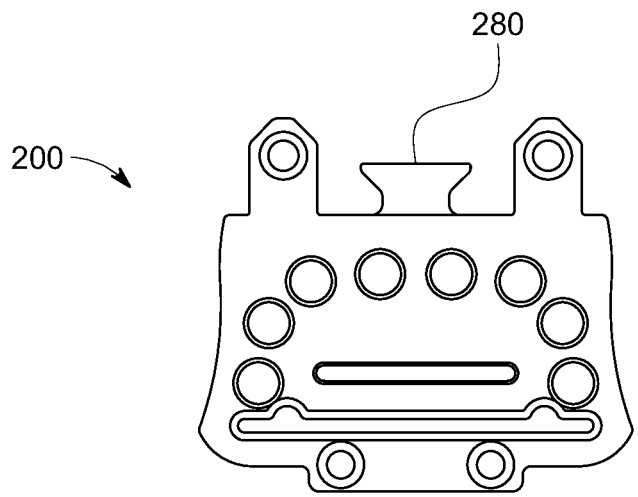
Figure 21:
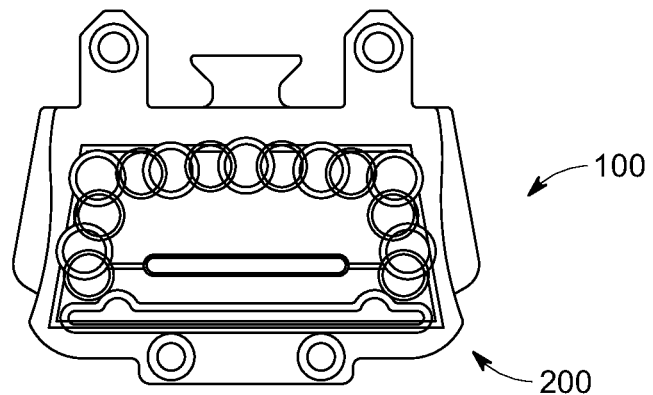
Figure 23:
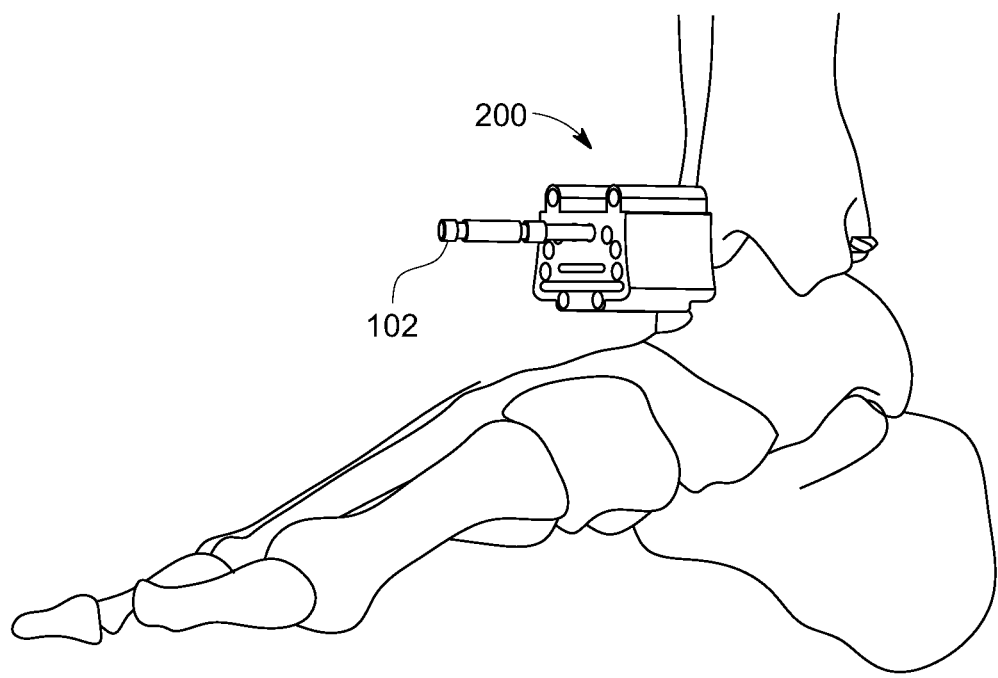
FIG. 23 is a perspective view of the resection guide of FIG. 11 and a drill for forming a portion of a tibia resection, according to an embodiment of the present disclosure.

With reference to FIGS. 20 and 23, the resection guide 200 may then be employed and aligned and positioned on the plurality of pins or guide wires 35 (FIG. 1) attached to a proximal portion of the tibia of the patient and aligned and positioned on a plurality of pins or guide wires 37 (FIG. 1) attached to a talus of the patient. If the alignment system 10 is also attached to the tibia of the patient, the resection guide 200 may also be operably attached to the alignment system via the coupler 280 (FIG. 20). Using the drill 102 (FIG. 23), a surgeon may next form a series of holes to continue the resection of the distal portion of the tibia. As shown in FIG. 21, the use of the resection guide 100 followed by use of the resection guide 200 results in a series of overlapping drilled holes in the tibia of the patient having an inverted arcuate or inverted U-shaped cutout or tibia arc resection along the distal portion of the tibia of the patient.

Figure 24:
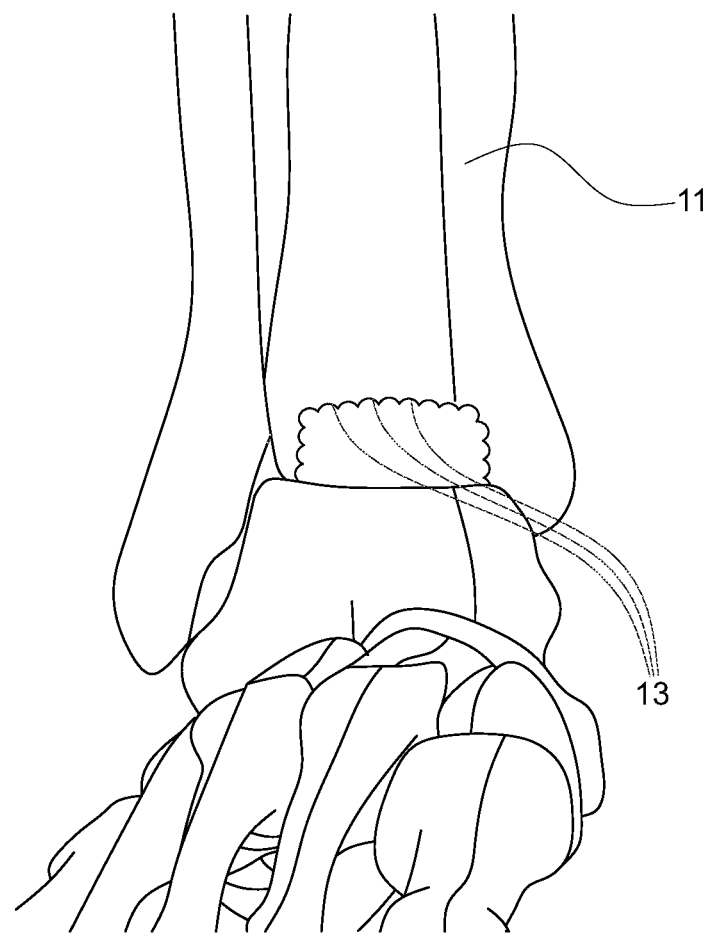
FIG. 24 is a front view of an ankle having an initial tibia resection using the resection guides of FIGS. 3 and 11, according to an embodiment of the present disclosure.

As shown in FIG. 24, the resected tibia 11 may include a plurality of curved surfaces 13 extending in an anterior to a posterior direction at the distal portion of the patient's tibia 11.

FIGS. 25-32 illustrate the sweeping reamer 300 for the tibial arc resection, according to an embodiment of the present disclosure. For example, after an initial resection is made with the resection guides 100 (FIG. 22) and 200 (FIG. 23), the sweeping reamer 300 guides a reamer 390 along an arc-path to clean the resected surface.

Figure 25:
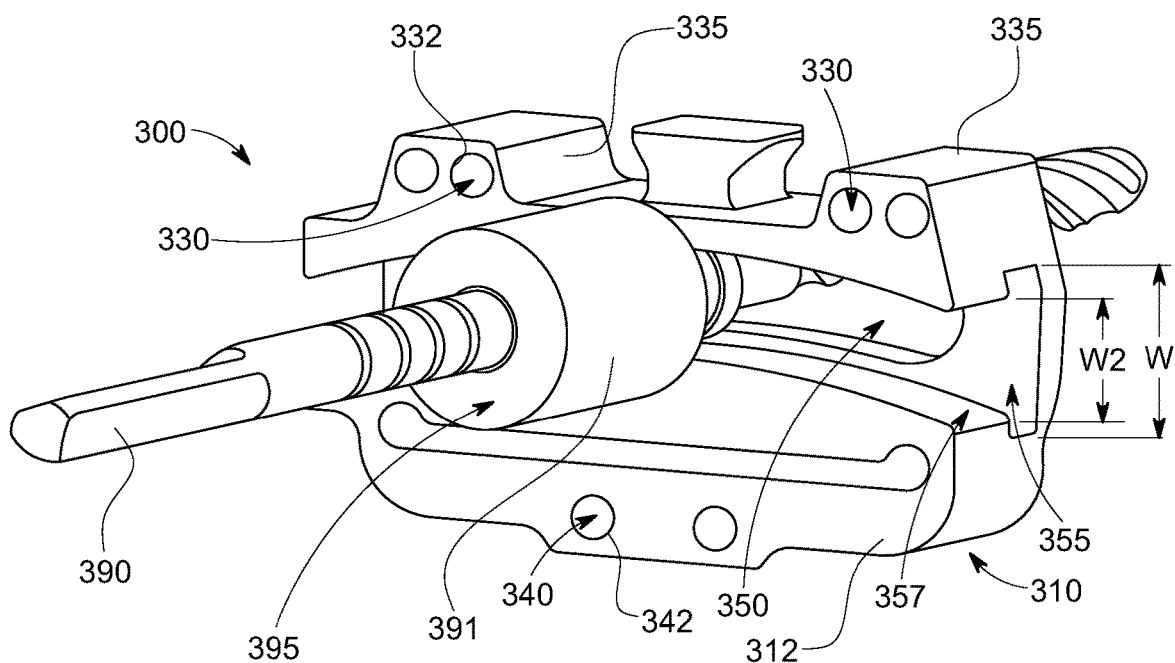
FIG. 25 is a top perspective view of a sweeping reamer, according to an embodiment of the present disclosure.
Figure 26:
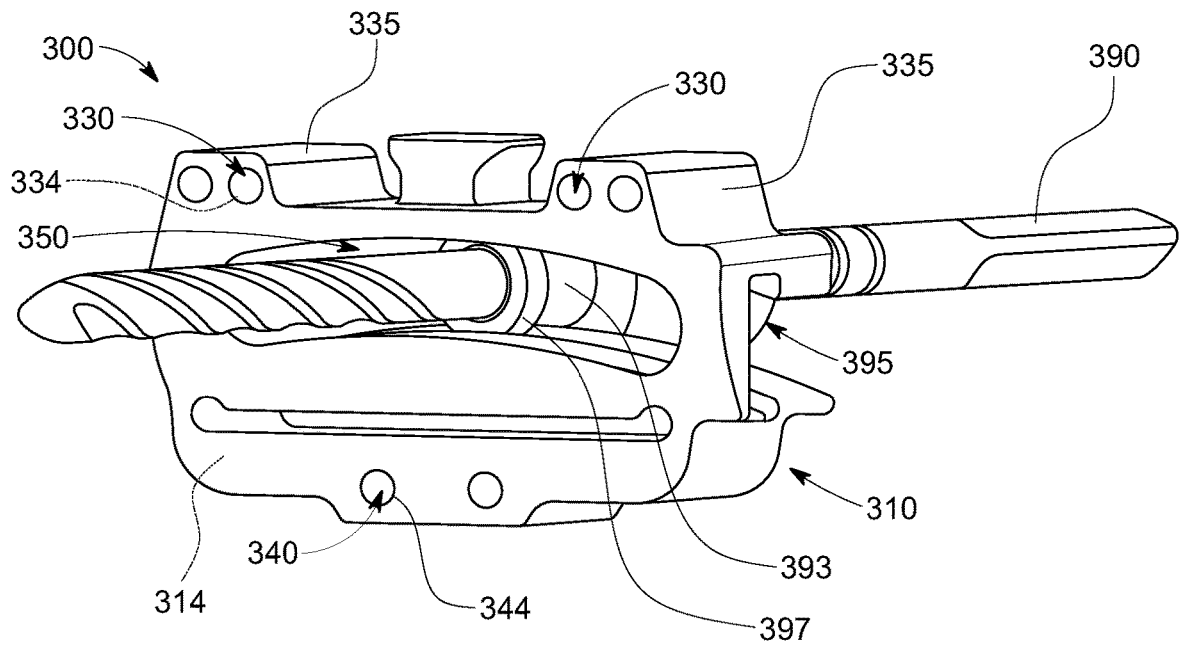
FIG. 26 is a bottom perspective view of the sweeping reamer of FIG. 25, according to an embodiment of the present disclosure.
Figure 27:
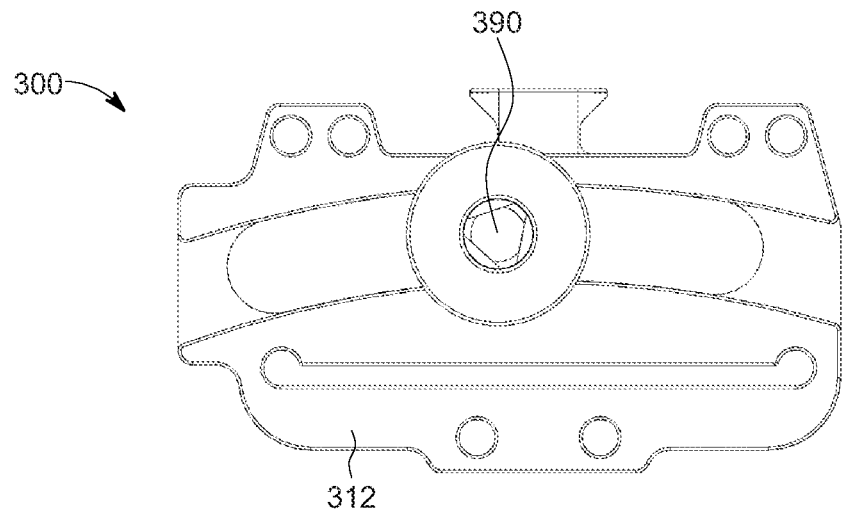
FIG. 27 is a front view of the sweeping reamer of FIG. 25, according to an embodiment of the present disclosure.
Figure 28:
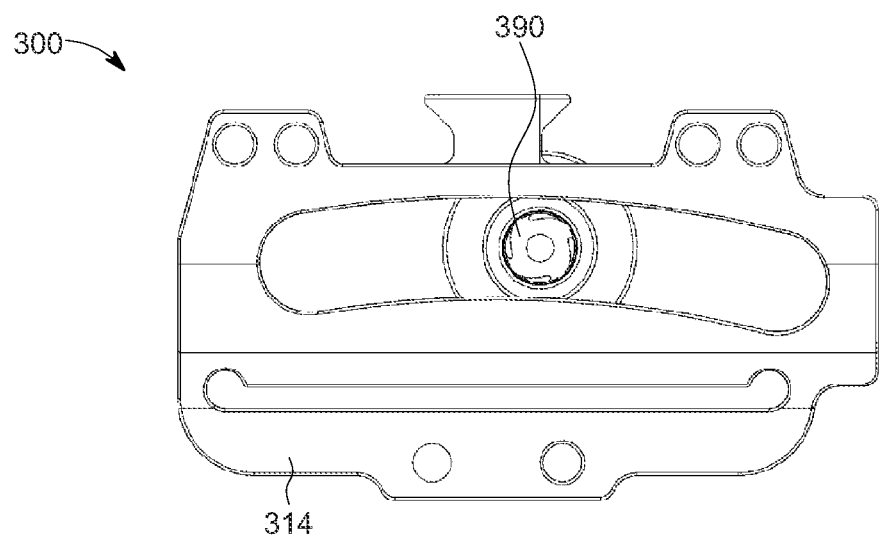
FIG. 28 is a rear view of the sweeping reamer of FIG. 25, according to an embodiment of the present disclosure.
Figure 29:
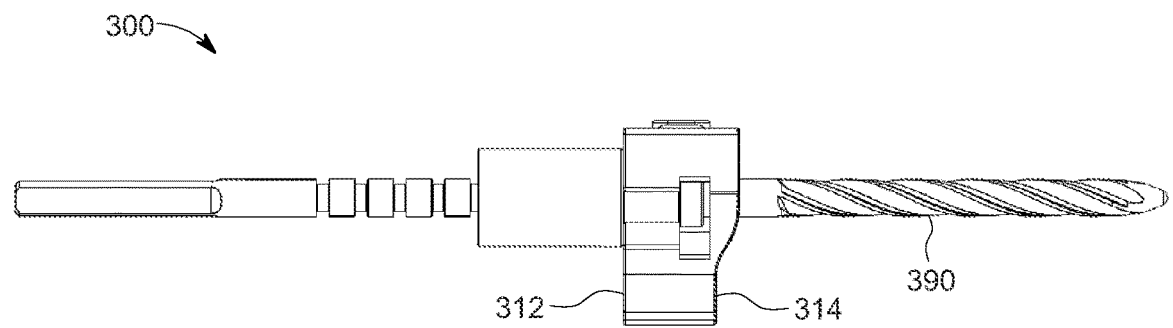
FIG. 29 is a right side view of the sweeping reamer of FIG. 25, according to an embodiment of the present disclosure.
Figure 30:
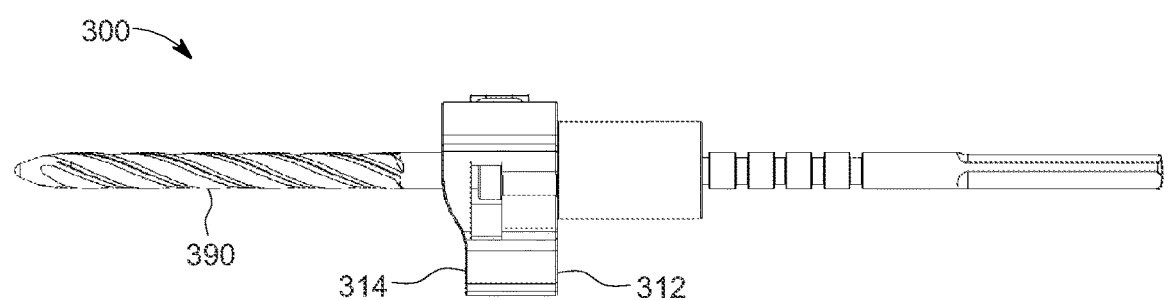
FIG. 30 is a left side view of the sweeping reamer of FIG. 25, according to an embodiment of the present disclosure.
Figure 31:
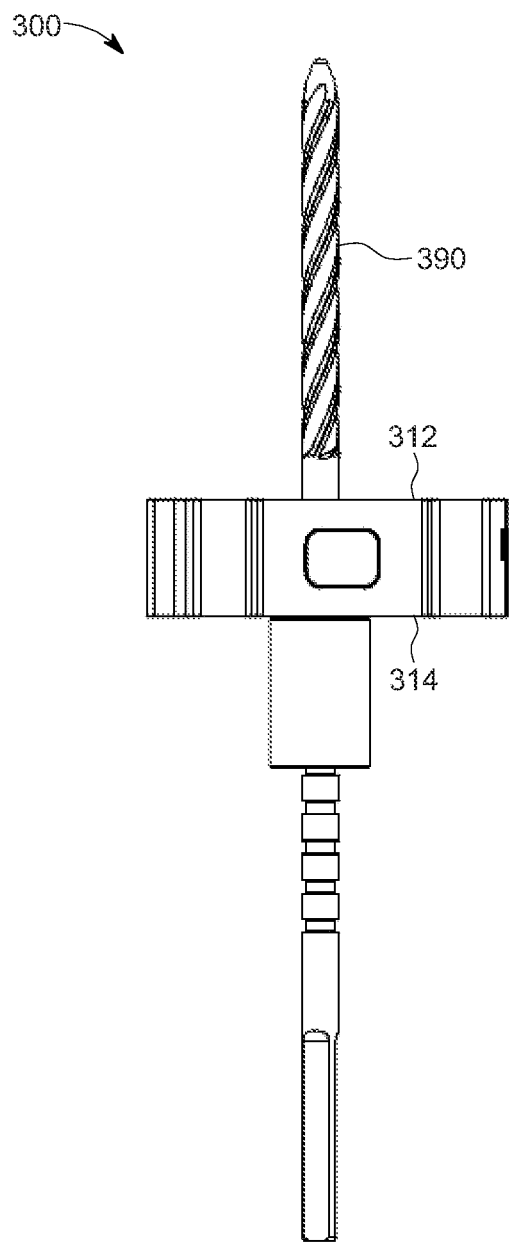
FIG. 31 is a top view of the sweeping reamer of FIG. 25, according to an embodiment of the present disclosure.
Figure 32:
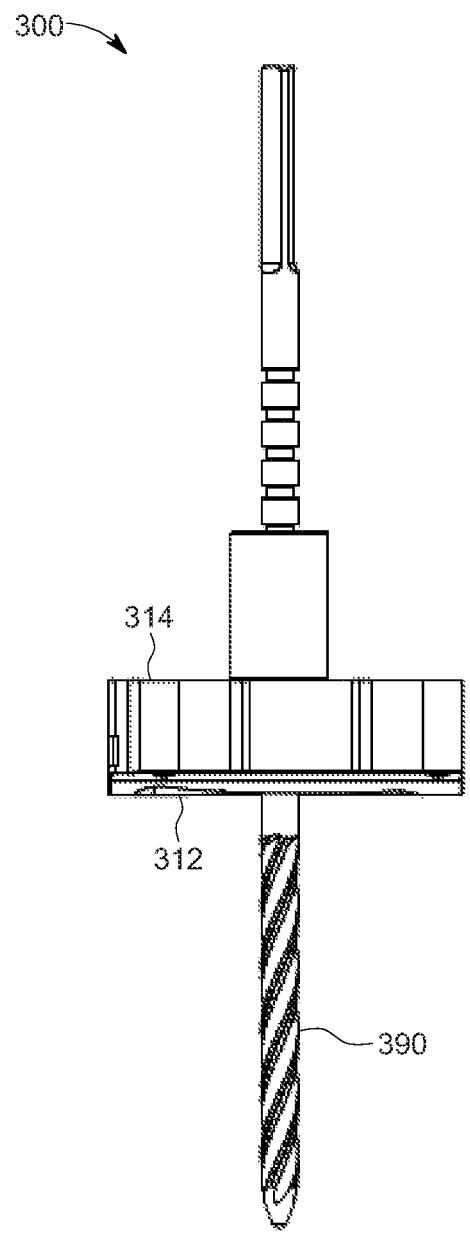
FIG. 32 is a bottom view of the sweeping reamer of FIG. 25, according to an embodiment of the present disclosure.

With reference to FIGS. 25 and 26, the sweeping reamer 300 may include a body 310 having a first side 312 and an opposite second side 314. The body 310 includes a plurality of alignment pin through-holes 330 extending from the first side to the second side of the body with openings 332 opening onto the first side of the body and openings 334 opening onto the second side of the body. The pattern of alignment pin through-holes 330 of the sweeping reamer 300 matches the pattern of alignment pin through-holes 30 (FIG. 1) of the sizing template 30 (FIG. 1), matches the pattern of alignment pin through-holes 130 (FIG. 3) of the first resection guide 100 (FIG. 3), matches the pattern of alignment pin through-holes 230 (FIG. 11) of the second resection guide 200 (FIG. 11), and matches the pattern of the alignment pins 35 (FIG. 1). The plurality of alignment pin through-holes 330 may be parallel to each other. For example, the two alignment pin through-holes 330 may be disposed in superiorly extending tabs 335 extending from body 310. Additional tibial alignment pin holes may be provided for use in different sized sizing templates and resection guides.

A plurality of talar alignment pin through-holes 340 may extend from the first side to the second side of the body with openings 342 opening onto the first side of the body and openings 344 opening onto the second side of the body. The pattern of talar alignment pin through-holes 340 of the sweeping reamer 300 matches the pattern of talar alignment pin through-holes 40 (FIG. 1) of the sizing template 30 (FIG. 1), matches the pattern of talar alignment pin through-holes 140 (FIG. 3) of the first resection guide 100 (FIG. 3), matches the pattern of talar alignment pin through-holes 240 (FIG. 11) of the second resection guide 200 (FIG. 11), and matches the pattern of the alignment pins 37 (FIG. 1).

The body 310 of sweeping reamer 300 also includes an elongated curved passageway 350 extending through body 310 and opening onto second side 314. The body 310 of sweeping reamer 300 may also include a T-shaped slot 355 having a first width W1 aligned and connected with elongated curved passageway 350 and sized wider than an elongated curved opening 357 having a second width W2, which elongated curved opening 357 opens onto first side 312 (FIG. 25).

The sweeping reamer 300 may also include a reamer 390 and a reamer guide 395. The reamer 390 extends through and is restrained in the sweeping reamer 300 by the reamer guide 395. The reamer guide 395 includes an interlocking cylindrical member that is receivable and restrained in the T-shaped slot 355. The reamer guide 395 may include a first cylindrical member 391 (FIG. 25), a second cylindrical member 393 (FIG. 26), and a third cylindrical member 397 (FIG. 26). The reamer 390 follows the arc-slot 350.

Figure 33:
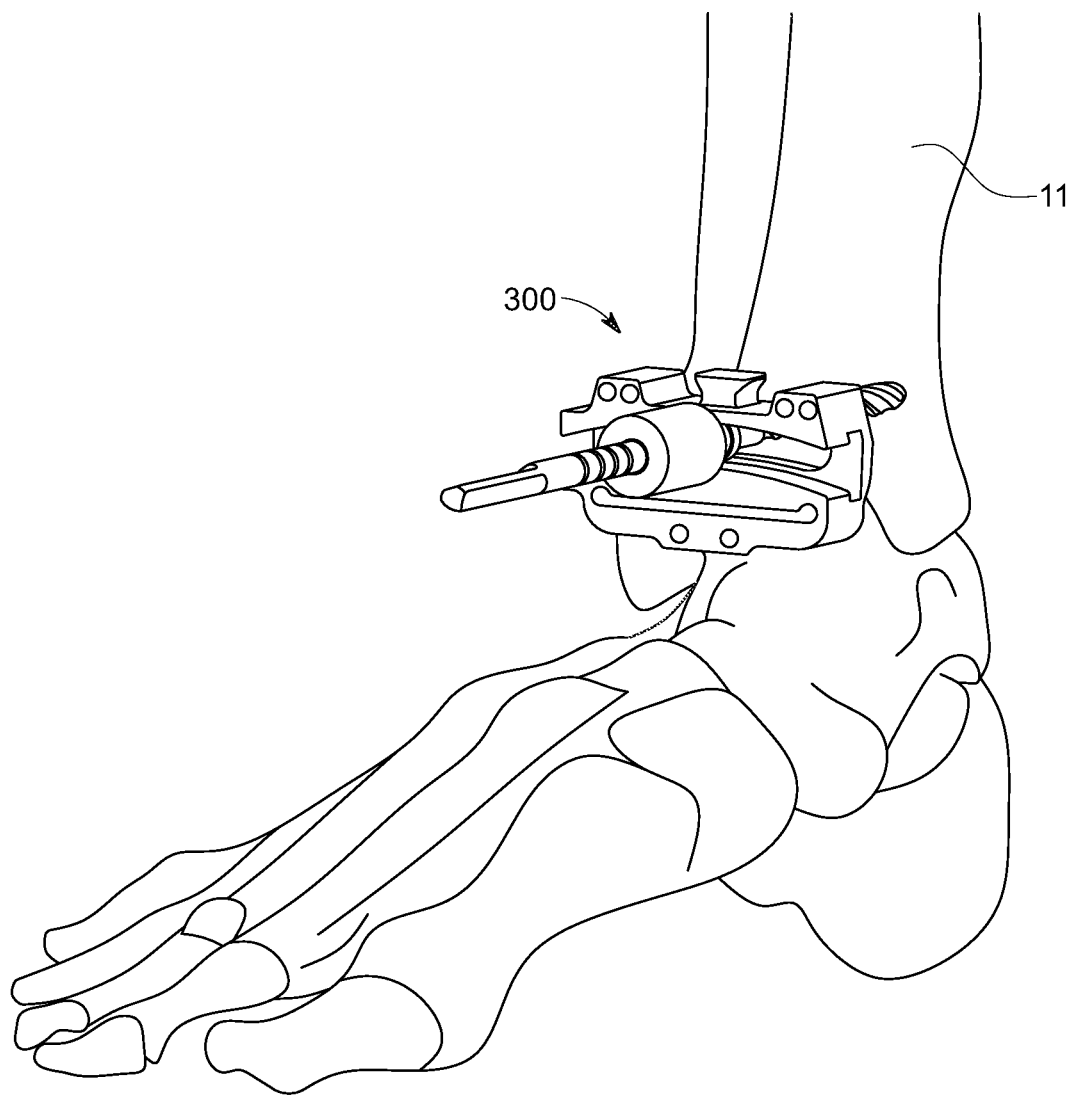
FIG. 33 is a perspective view of the sweeper reamer of FIG. 25 for further forming the resected portion of the tibia shown in FIG. 24, according to an embodiment of the present disclosure.
Figure 34:
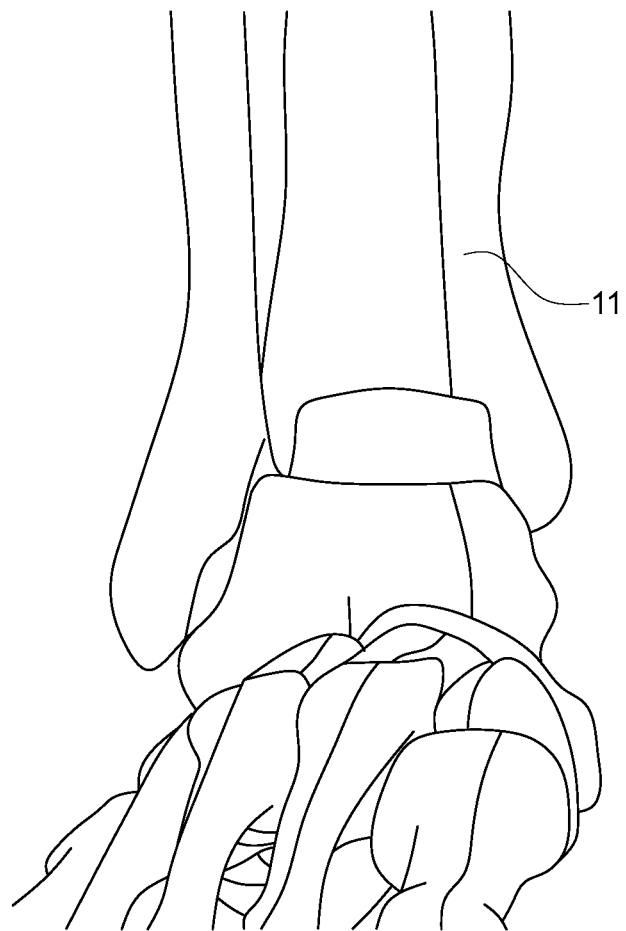
FIG. 34 is a front view of the ankle having the tibia resection using the sweeping reamer of FIG. 25, according to an embodiment of the present disclosure.
Figure 35:
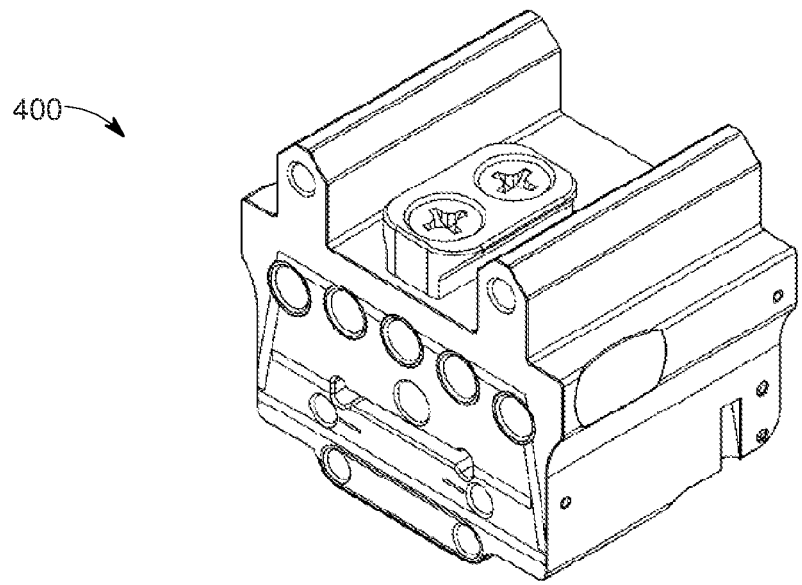
FIG. 35 is a top perspective view of a resection guide, according to an embodiment of the present disclosure.
Figure 36:
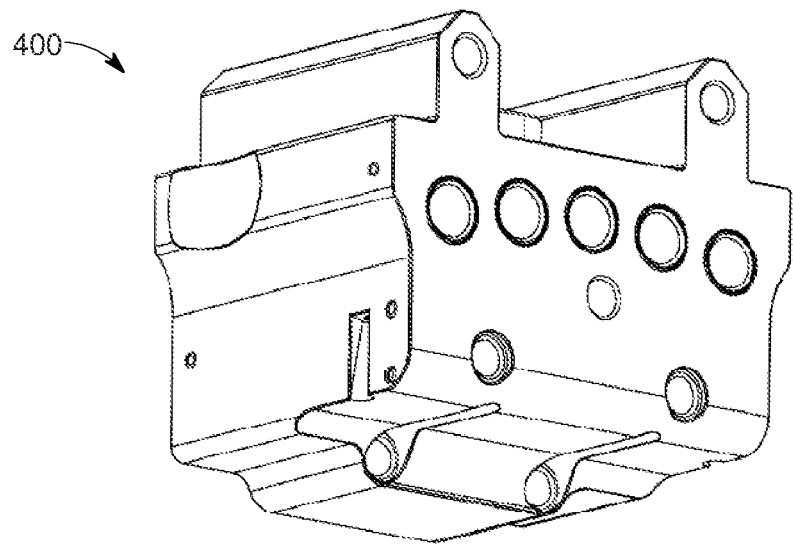
FIG. 36 is a bottom perspective view of the resection guide of FIG. 35, according to an embodiment of the present disclosure.
Figure 37:
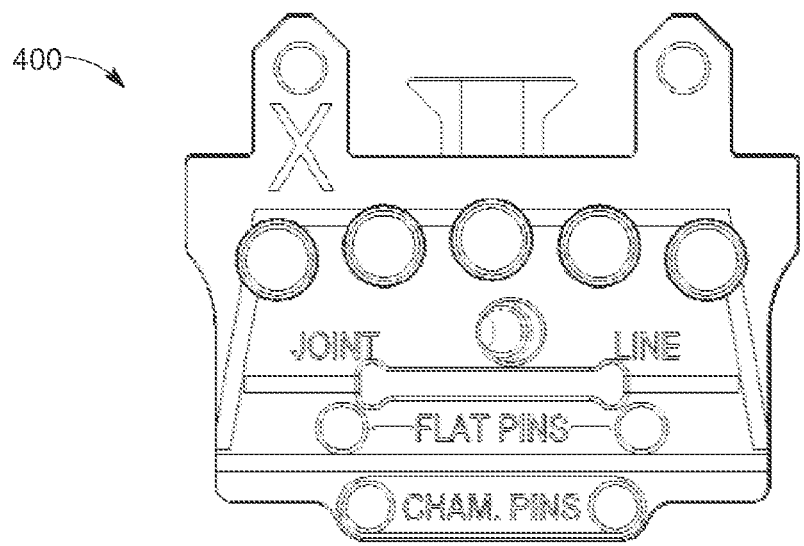
FIG. 37 is a front view of the resection guide of FIG. 35, according to an embodiment of the present disclosure.
Figure 38:
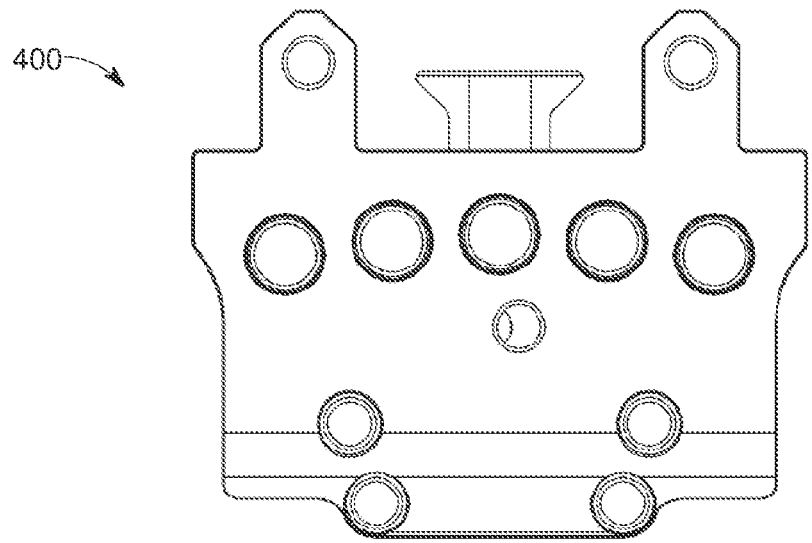
FIG. 38 is a rear view of the resection guide of FIG. 35, according to an embodiment of the present disclosure.
Figure 39:
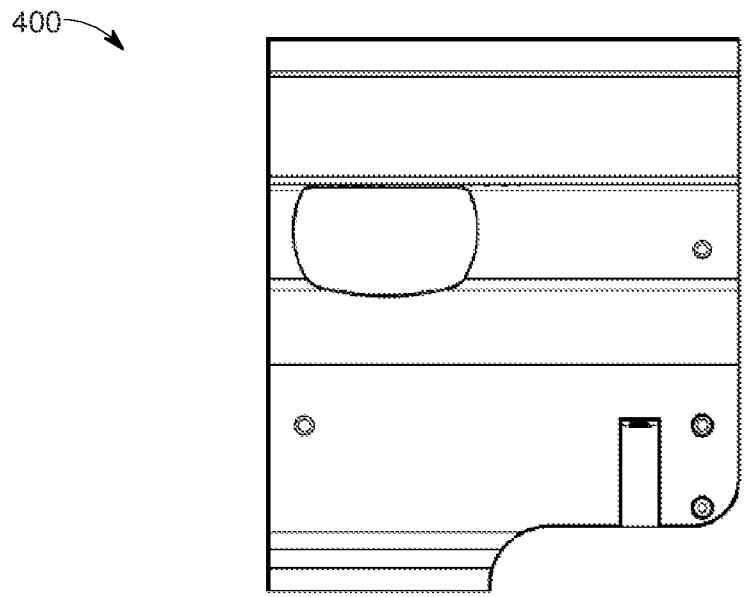
FIG. 39 is a right side view of the resection guide of FIG. 35, according to an embodiment of the present disclosure.
Figure 40:
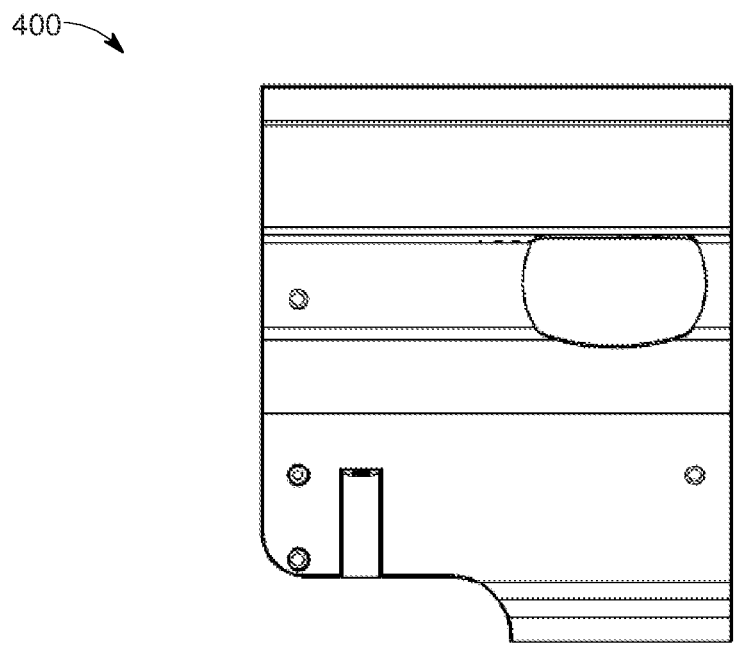
FIG. 40 is a left side view of the resection guide of FIG. 35, according to an embodiment of the present disclosure.
Figure 41:
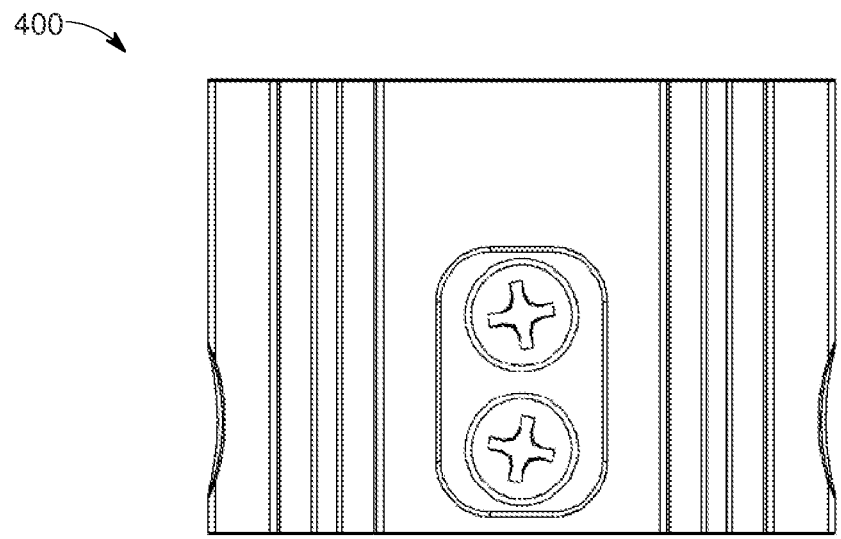
FIG. 41 is a top view of the resection guide of FIG. 35, according to an embodiment of the present disclosure.
Figure 42:
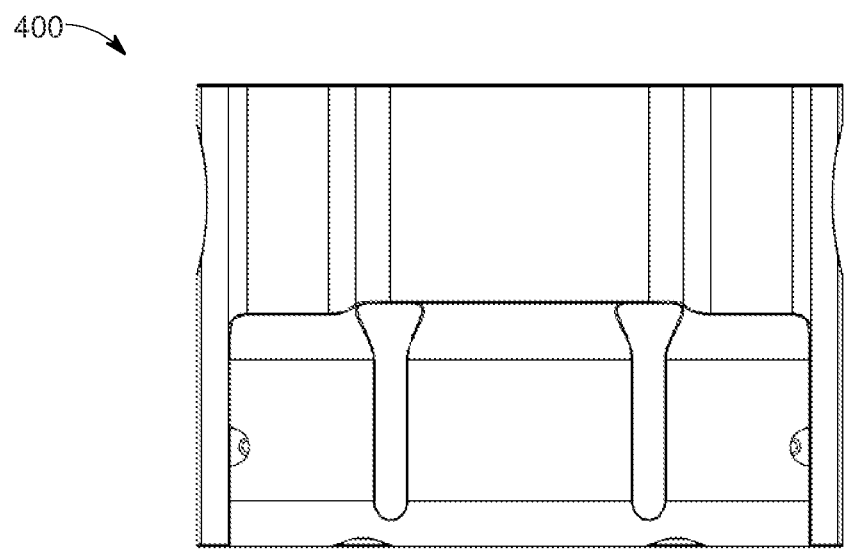
FIG. 42 is a bottom view of the resection guide of FIG. 35 according to an embodiment of the present disclosure.

As shown in FIG. 33, sweeping reamer 300 operates to clean the initially resected portion of the tibia 11 and remove the concave portions 13 (FIG. 24) resulting in the resected tibia shown in FIG. 34. In other embodiments, the initially resected tibia may be cleaned using an arced osteotome or chisel, an arced rasp having a curved surface, or other suitable tools (not shown). An arced osteotome or chisel may help separate the resected bone from the tibia (osteotome), and clear away any bone that was not cleanly removed by the drill on the implant interfacing bone surface. The tip may be either single (i.e., chisel) or double (i.e., osteotome) beveled for different resection requirements. The arced rasp is operable to clean the ridges created during the arced resection using a curved rasp surface. The arced rasp may include angled rasping surfaces for cleanup of the medial and lateral sides after the drilling.

FIGS. 35-42 illustrate a resection guide 400, according to an embodiment of the present disclosure. The resection guide 400 may be essentially the same as resection guide 200 (FIGS. 11-18) with the exception of a single series of drill holes extending along an arc. The resection guide 400 may be used with sweeping reamer 300. A cutting tool may be suitably employed for resecting the sides for the tibial cutout.

FIGS. 43-52 illustrate a decoupled talar resection guide 500, according to an embodiment of the present disclosure. As an alternative option to coupled the tibial and talar resection guides, for example, the coupled tibial and talar resection guides 200 and 400, a surgeon is able to use the decoupled talar resection guide 500 to place tension on the soft tissue connecting the talus to the tibia. In ankle joints with varus-valgus deformities, this can allow the surgeon to straighten the ankle to provide a horizontal cut in the talus.

Figure 43:
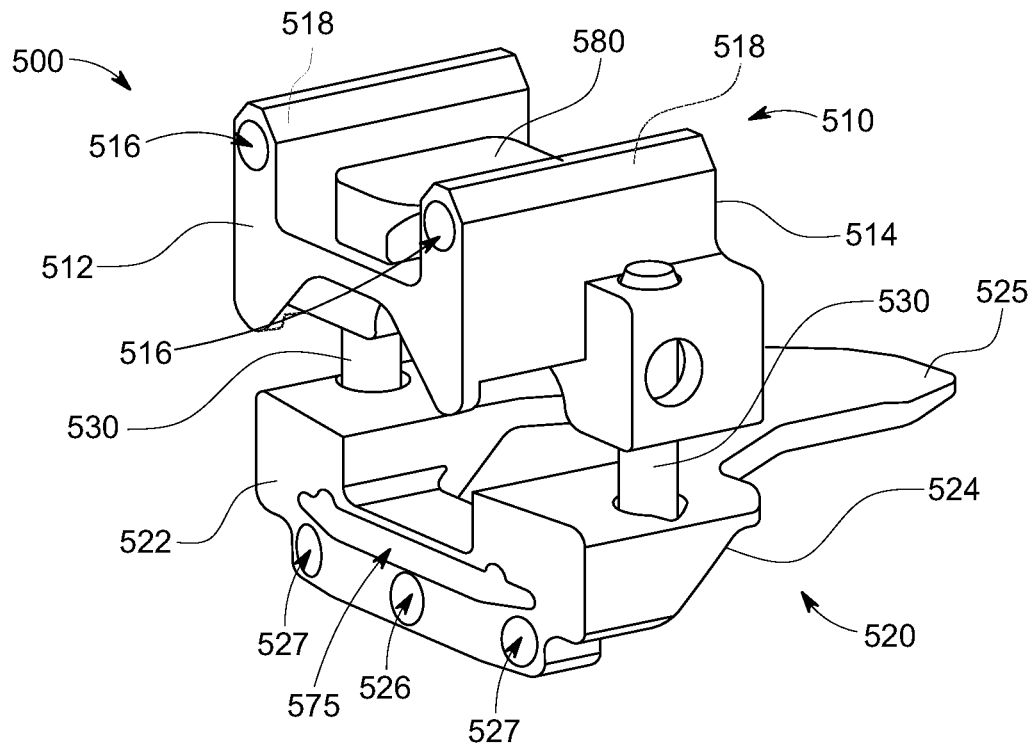
FIG. 43 is a top perspective view of a decoupled resection guide, according to an embodiment of the present disclosure.
Figure 44:
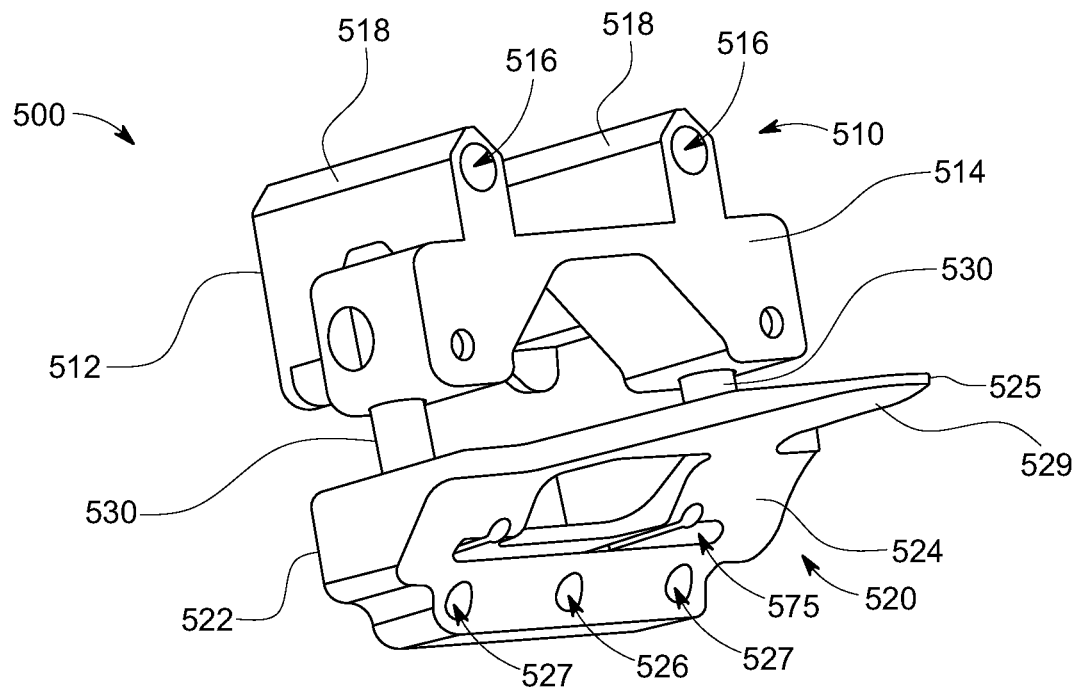
FIG. 44 is a bottom perspective view of the decoupled resection guide of FIG. 43, according to an embodiment of the present disclosure.
Figure 45:
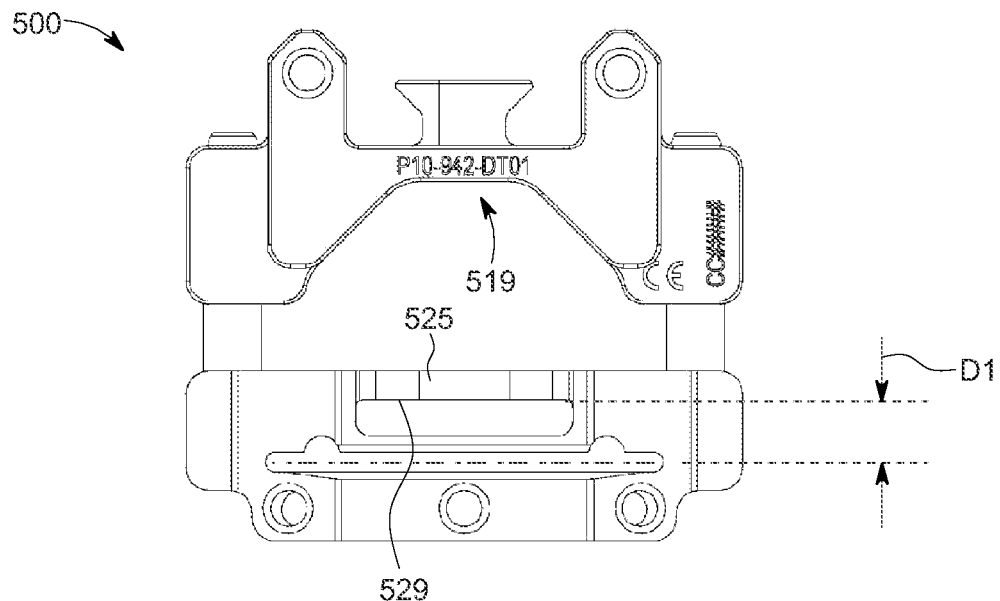
FIG. 45 is a front view of the decoupled resection guide of FIG. 43, according to an embodiment of the present disclosure.
Figure 46:
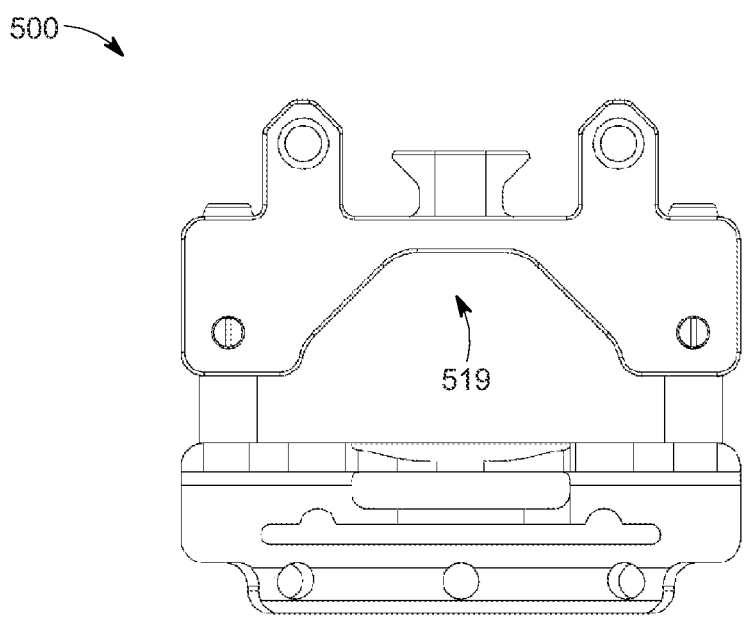
FIG. 46 is a rear view of the decoupled resection guide of FIG. 43, according to an embodiment of the present disclosure.
Figure 47:
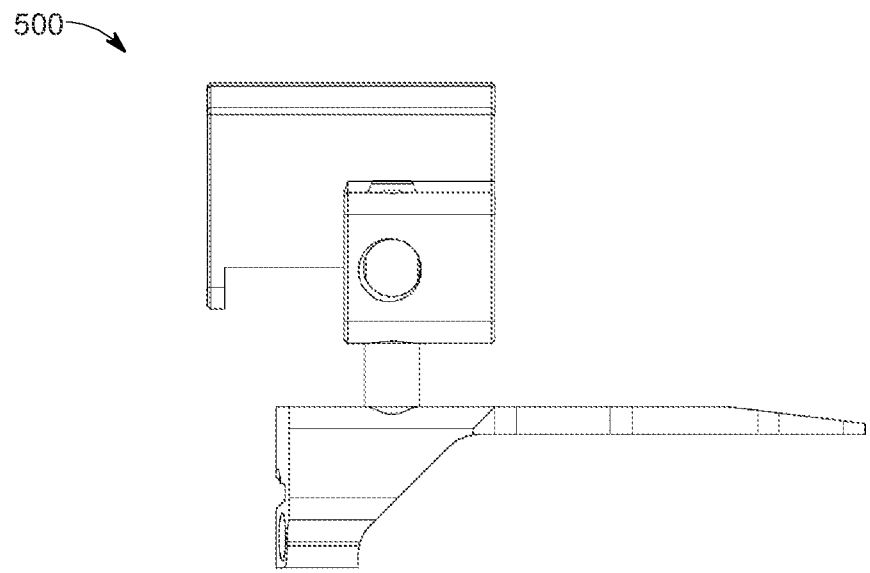
FIG. 47 is a right side view of the decoupled resection guide of FIG. 43, according to an embodiment of the present disclosure.
Figure 48:
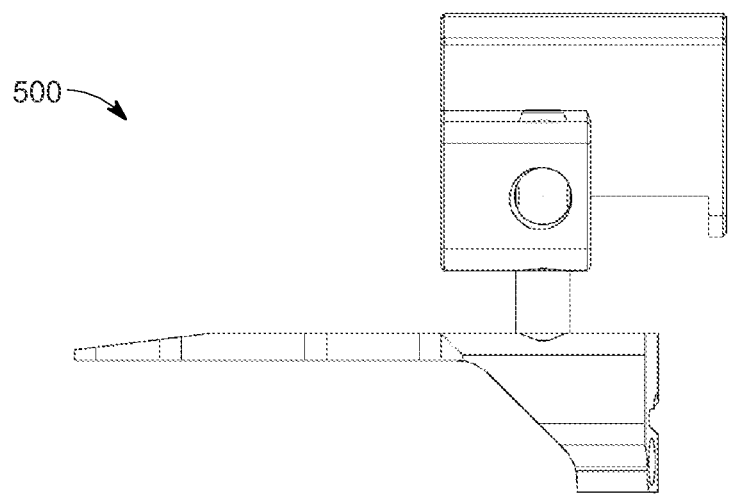
FIG. 48 is a left side view of the decoupled resection guide of FIG. 43, according to an embodiment of the present disclosure.
Figure 49:
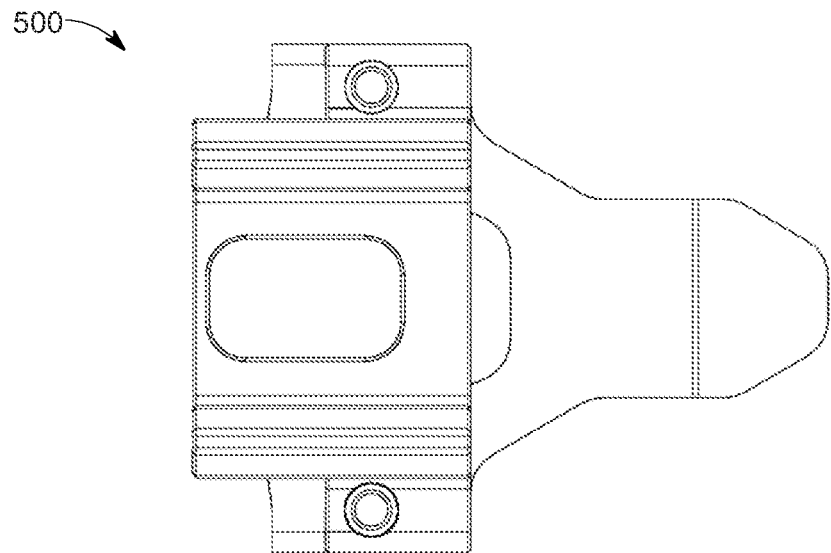
FIG. 49 is a top view of the decoupled resection guide of FIG. 43, according to an embodiment of the present disclosure.

With reference to FIGS. 43 and 44, the decoupled talar resection guide 500 may include a superior body portion 510 having a first side 512 and an opposite second side 514, an inferior body portion 520 having a first side 522 and an opposite second side 524, and a pair of connecting pins 530 for operably connecting the superior body portion 510 to inferior body portion 520.

The superior body portion 510 includes a plurality of alignment pin through-holes 516 extending from the first side to the second side of the body with openings opening onto the first side of the body and openings opening onto the second side of the body. The plurality of alignment pin through-holes 516 may be parallel to each other. The two alignment pin through-holes 516 may be disposed in superiorly-extending tabs 518 extending from superior body portion 510. The superior body portion 510 may have an arched cutout 519 (best shown in FIGS. 45 and 46) extending from first side 512 to the opposite second side 514.

As will be appreciated, alignment pin through-holes 516 of the decoupled talar resection guide 500 may match the locations of the alignment pin through-holes in the resection guides 100, 200, and 400 so as to be usable with the same alignment pins and system used to initially resect the tibia. In some embodiments, the alignment pin through-holes 516 (FIG. 43) may be 2.4 mm diameter drill holes.

The inferior body portion 520 may include a plurality of talus fixation pin through-holes 526 and 527 extending from the first side to the second side of the body with openings opening onto the first side of the body and openings opening onto the second side of the body. The plurality of alignment pin through-holes 516 and center talus fixation pin through-hole 526 may be parallel to each other. The medial and lateral talus fixation pin through-holes 527 may be disposed at different anterior to posterior angles. For example, the outer talus fixation pin through-holes 527 may be angled to guide fixation pins toward each other and into the patient's talus. The talus fixation through-holes may be 2.4 mm drill holes.

Figure 50:
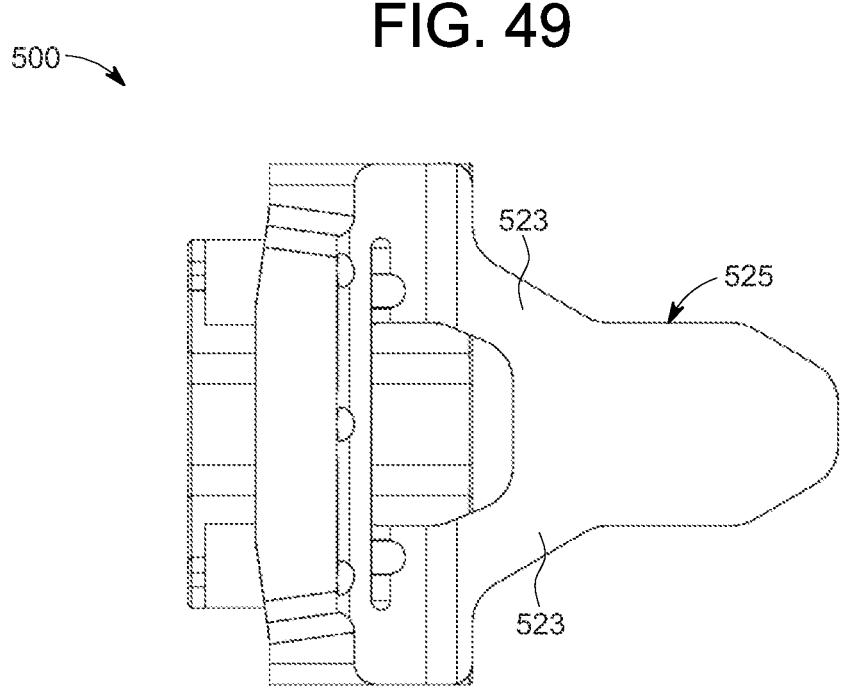
FIG. 50 is a bottom view of the decoupled resection guide of FIG. 43 according to an embodiment of the present disclosure.

The inferior body portion 520 may include a posteriorly-extending talar paddle 525. The inferior body portion may include an elongated guide slot 575 for resecting the talus. The center of the elongated guide slot 575 is spaced a distance D1 (FIG. 45) from an inferior surface 529 (FIG. 45) of the talar paddle 525. The talar paddle 525 is operable to allow a surgeon to place a downward or inferiorly directed force onto the talus during distraction. As best shown in FIG. 50, the paddle 525 may be Y-shaped having spaced apart legs 523.

Figure 51:
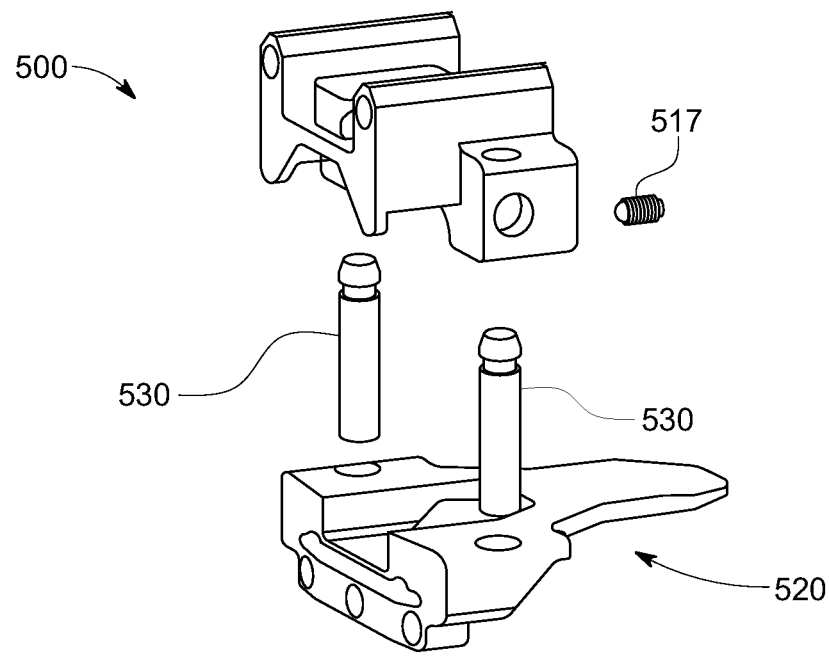
FIG. 51 is an exploded top perspective view of the decoupled resection guide of FIG. 43, according to an embodiment of the present disclosure.
Figure 52:
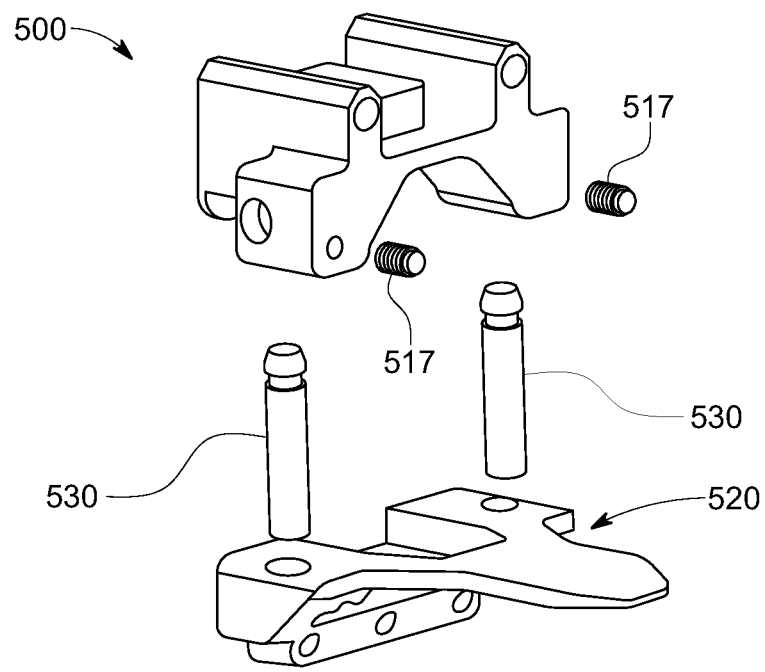
FIG. 52 is an exploded top perspective view of the decoupled resection guide of FIG. 43, according to an embodiment of the present disclosure.

With reference to FIGS. 51 and 52, connecting members 530 may have an inferior end fixedly securable in a recessed hole in the inferior body portion 520. The superior body portion 510 includes threaded holes operable for receiving threaded locking screws 517 for locking superior body portion 510 to the connecting member 530 and maintaining the distal portion of a patient's tibia relative to the patient's talus in tension. In other embodiments, the locking screws may be received in threaded holes disposed on the sides of the superior body portion of the decoupled talar resection guide 500.

With reference again to FIG. 43, a coupler 580 may be attached to the superior body portion 510 for connecting the superior body portion to the alignment system 10 (FIG. 1). For example, the coupler 580 may be a flaring tenon that slides into a mortise in the alignment system 10 (FIG. 1), e.g., forming a dovetail joint.

Figure 53:
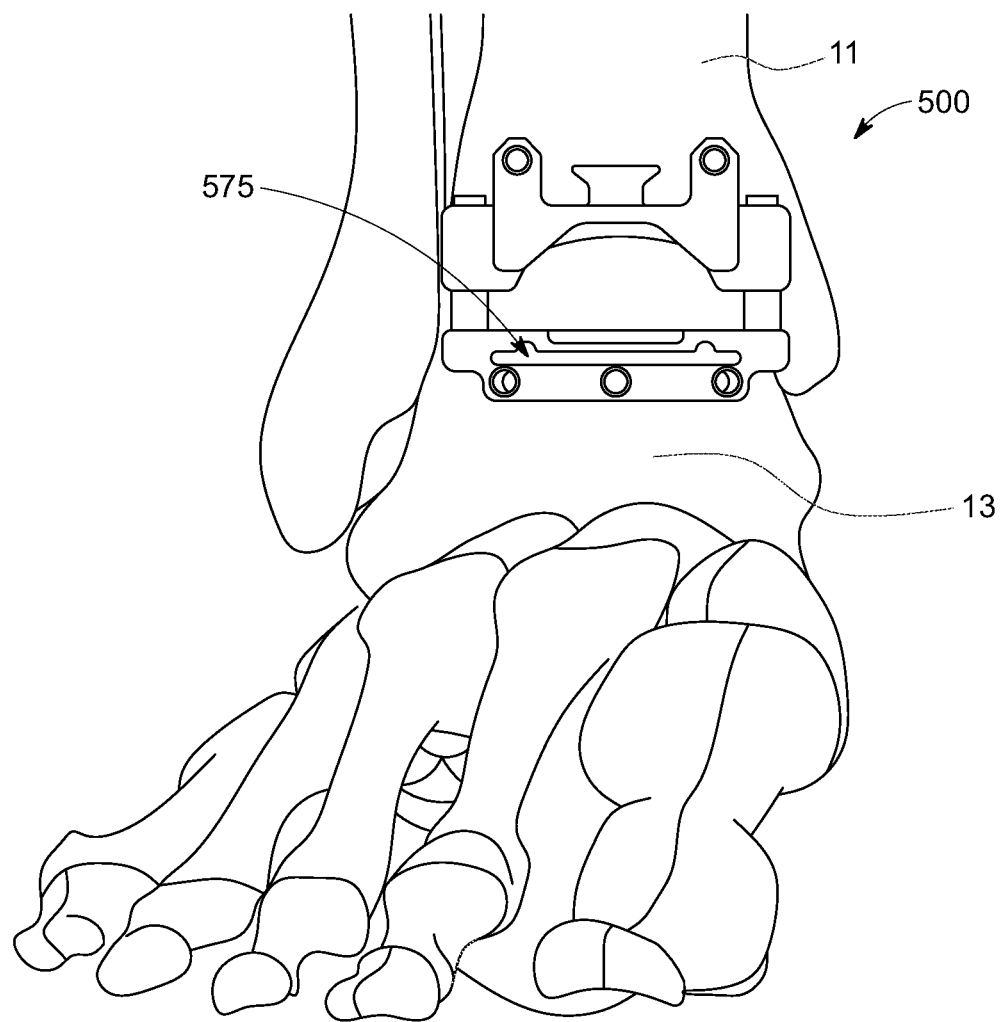
FIG. 53 is a front view of the decoupled resection guide of FIG. 43 for forming a resection of the talus, according to an embodiment of the present disclosure.
Figure 54:
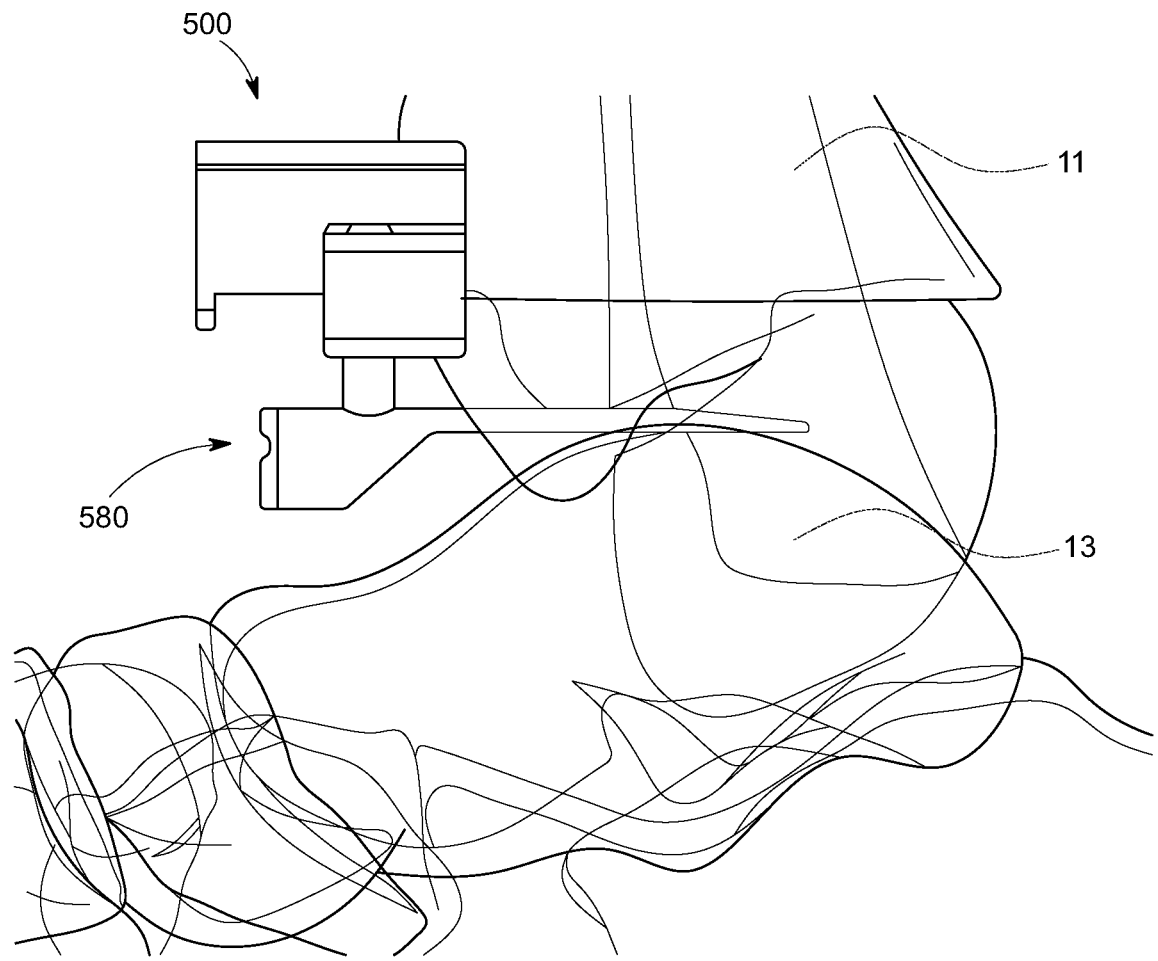
FIG. 54 is a right side view of the decoupled resection guide of FIG. 43 for forming the resection of the talus, according to an embodiment of the present disclosure.

With reference to FIGS. 53 and 54, the decoupled talar resection guide 500 may be employed and aligned and positioned on the plurality of pins or guide wires 35 (FIG. 1) secured to the tibia after resection of the tibia 11, e.g., as shown in FIG. 34. Once the decoupled talar resection guide 500 is adjusted by a surgeon to apply a force between the tibia 11 and the talus to operably space the tibia from the talus, a surgeon may next resect the talus using a cutting tool guided in slot 575.

FIGS. 55 and 56 illustrate a decoupled talar resection guide 600, according to an embodiment of the present disclosure. Decoupled talar resection guide 600 is essentially the same as decoupled talar resection guide 500 (FIGS. 43-50) with the exception that inferior body portion 620 includes a viewing window 621 to allow a surgeon to ensure that the paddle is properly engaging the talus. As shown in FIG. 55, the superior body portion 610 is initially disposed in contact with inferior body portion 620 for engagement of the lamina spreader to provide distraction/tension of the instrument/joint. As shown in FIG. 56, distraction results in superior body portion 610 being spaced from inferior body portion 620 and operably locked in place using, for example, locking screws, as described above.

FIGS. 57-66 illustrate a decoupled talar resection guide 700, according to an embodiment of the present disclosure. As an alternative option to a coupled talar resection guide, for example, the coupled tibial and talar resection guides 200 and 400, a surgeon is able to use the decoupled talar resection guide 700 to place different amounts of tension on the medial and lateral soft tissue between the talus and the tibia of the patient. In ankle joints with varus-valgus deformities, this can allow the surgeon to straighten the ankle to provide a horizontal cut in the talus.

Figure 57:
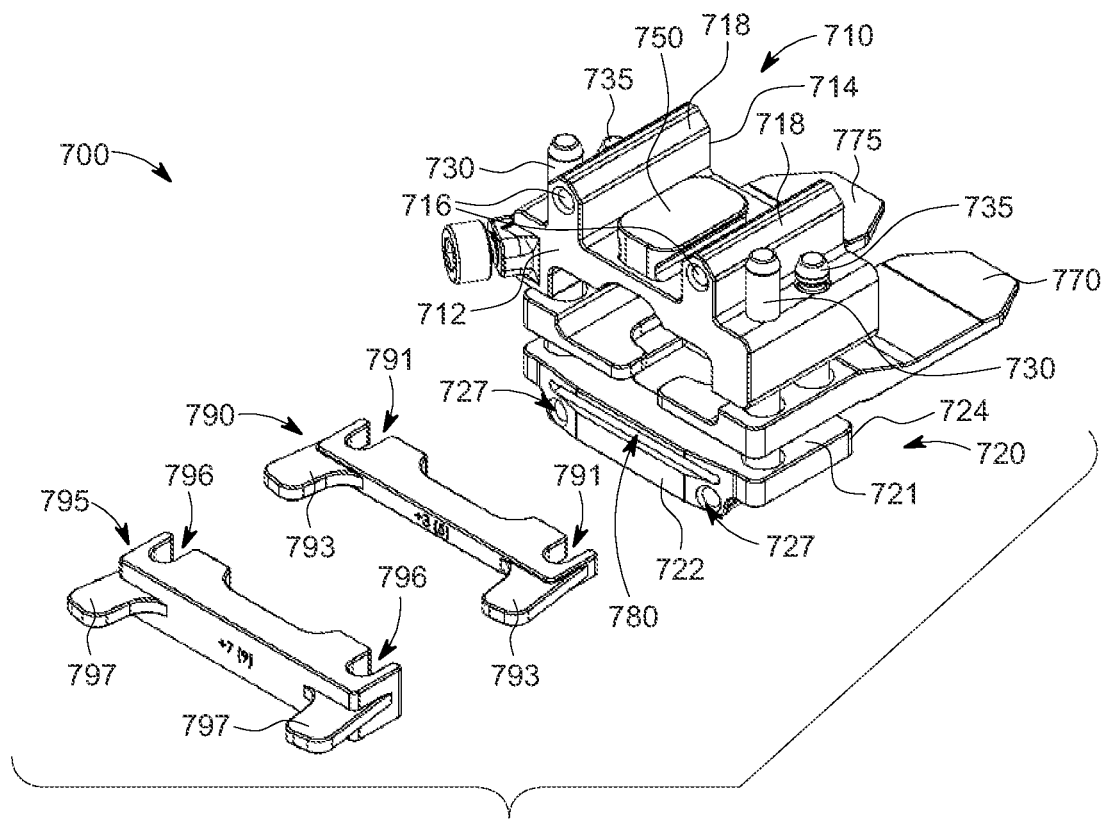
FIG. 57 is a top perspective view of a decoupled resection guide, according to an embodiment of the present disclosure.
Figure 58:
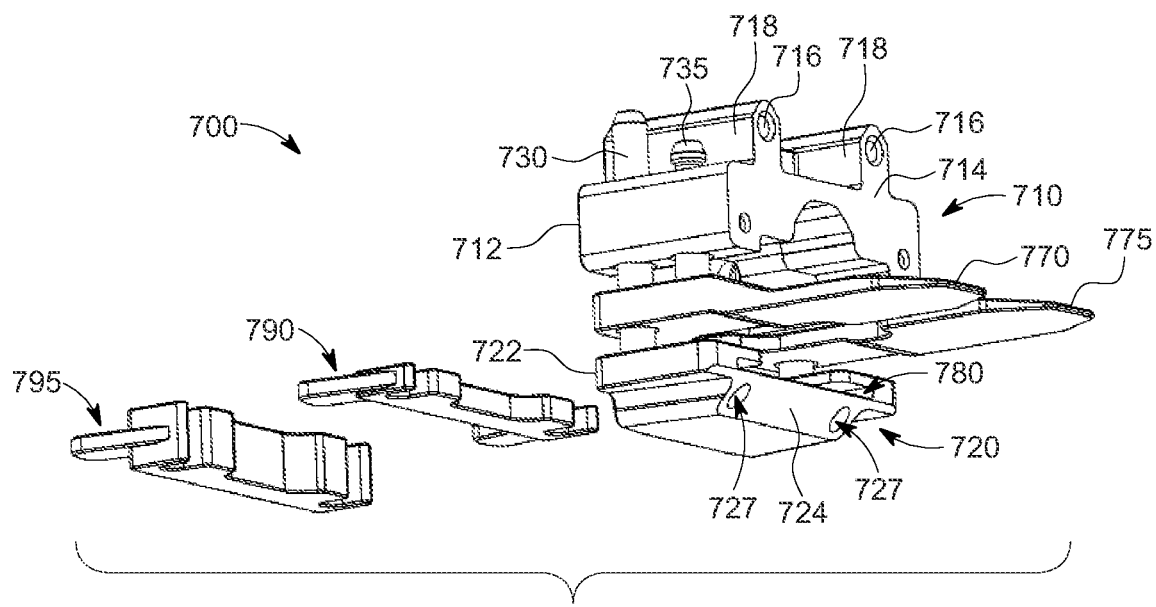
FIG. 58 is a bottom perspective view of the decoupled resection guide of FIG. 57, according to an embodiment of the present disclosure.
Figure 59:
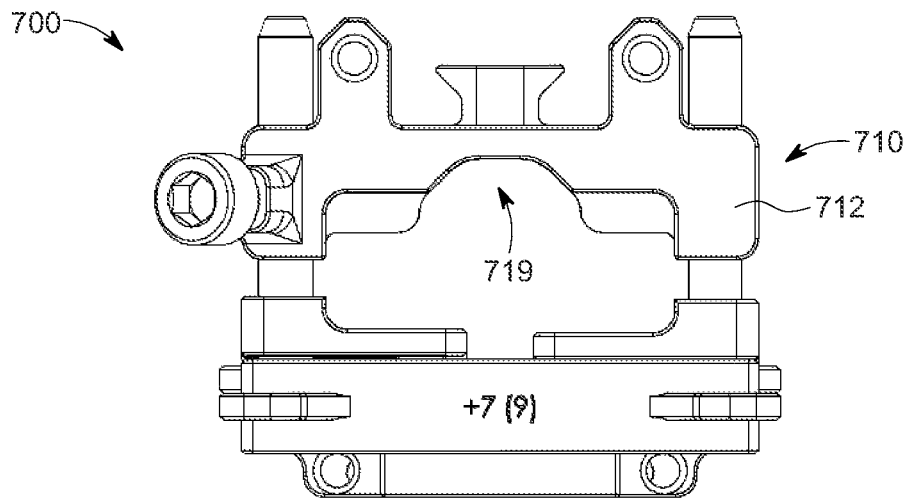
FIG. 59 is a front view of the decoupled resection guide of FIG. 57, according to an embodiment of the present disclosure.
Figure 60:
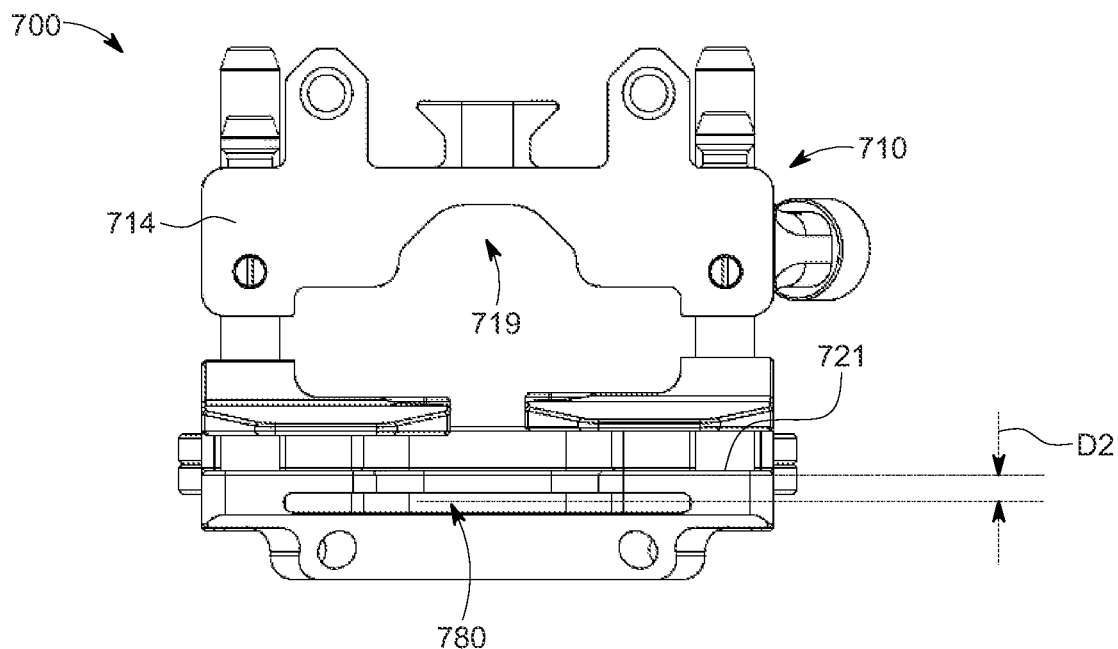
FIG. 60 is a rear view of the decoupled resection guide of FIG. 57, according to an embodiment of the present disclosure.
Figure 61:
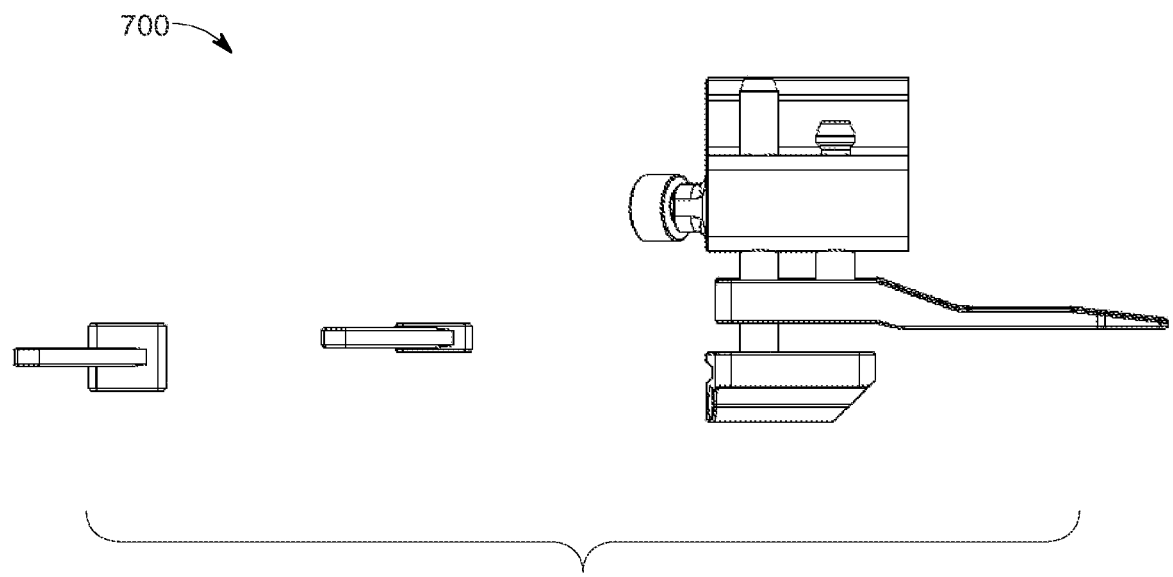
FIG. 61 is an exploded right side view of the decoupled resection guide of FIG. 57, according to an embodiment of the present disclosure.
Figure 62:
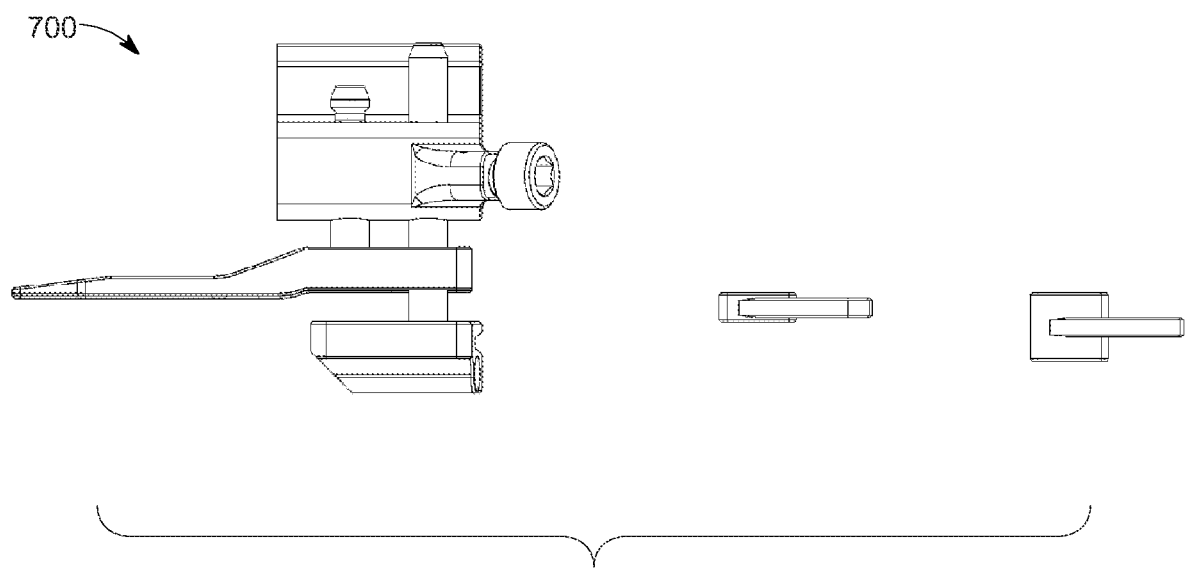
FIG. 62 is an exploded left side view of the decoupled resection guide of FIG. 57, according to an embodiment of the present disclosure.
Figure 63:
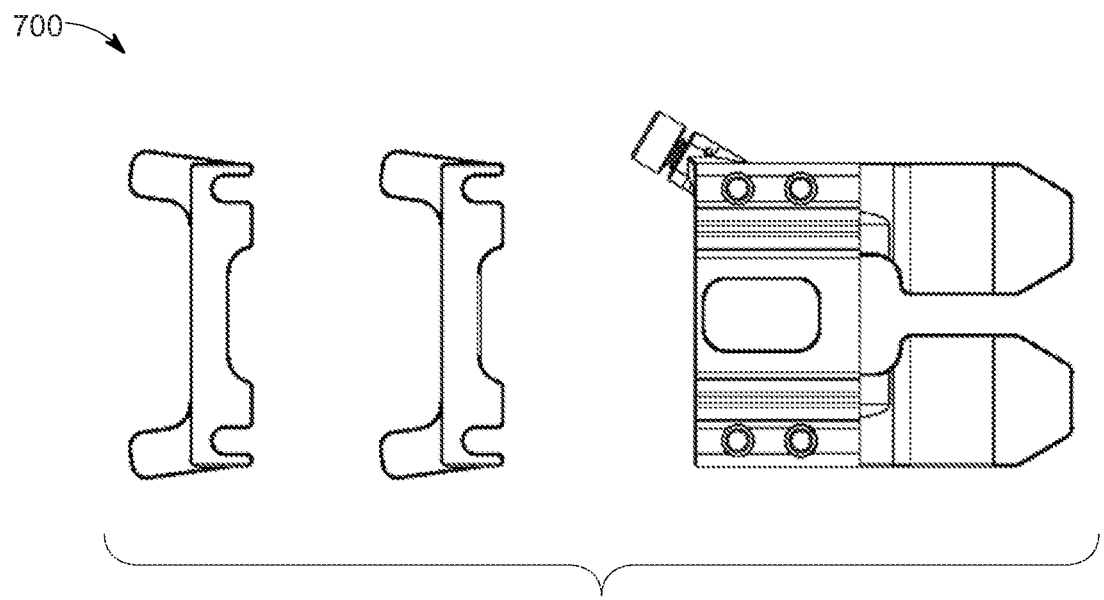
FIG. 63 is an exploded top view of the decoupled resection guide of FIG. 57, according to an embodiment of the present disclosure.
Figure 64:
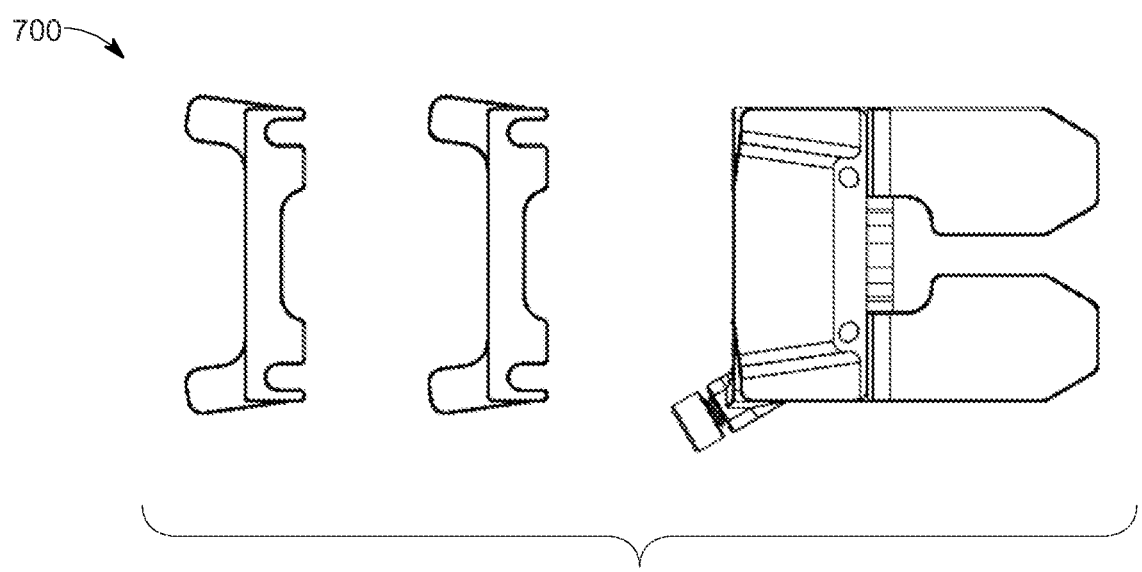
FIG. 64 is an exploded bottom view of the decoupled resection guide of FIG. 57 according to an embodiment of the present disclosure.

With reference to FIGS. 57 and 58, the decoupled talar resection guide 700 may include a superior body portion 710 having a first side 712 and an opposite second side 714, an inferior body portion 720 having a first side 722 and an opposite second side 724, connecting pins 730 and 735 for operably connecting the superior body portion 710 to inferior body portion 730, a plurality of paddles 770 and 775, and a plurality of differently sized spacers 790 and 795. The connecting pins 730 and 735 are operable to movably connect the superior body portion 710 to the inferior body portion 720 and restrain the paddles 770 and 775 therebetween.

The superior body portion 710 may include a plurality of alignment pin through-holes 716 extending from the first side to the second side of the body to define a pattern of alignment pin through-holes 716 with openings opening onto the first side of the body and openings opening onto the second side of the body. The plurality of alignment pin through-holes 716 may be parallel to each other. The two alignment pin through-holes 716 may be disposed in superiorly-extending tabs 718 extending from superior body portion 710. The superior body portion 710 may have an arched cutout 719 (best shown in FIGS. 59 and 60) extending from first side 712 to the opposite second side 714.

As will be appreciated, alignment pin through-holes 716 of the decoupled talar resection guide 700 may match the locations of the alignment pin through-holes in the resection guides 100, 200, and 400 so as to be usable with the same alignment pins and system used to initially resect the tibia. In some embodiments, the alignment pin through-holes 716 (FIG. 57) may be 2.4 mm diameter pin holes.

With reference again to FIGS. 57 and 58, the inferior body portion 720 may include a plurality of talus fixation pin through-holes 727 extending from the first side to the second side of the body with openings opening onto the first side of the body and openings opening onto the second side of the body. The medial and lateral talus fixation pin through-holes 727 may be disposes at different anterior to posterior angles. For example, the talus fixation pin through-holes 727 may be angled to guide fixation pins toward each other and into the patient's talus. The inferior body portion 720 may include an elongated guide slot 780 for resecting the talus. The center of the elongated guide slot 780 is spaced a distance D2 (FIG. 60) from a surface 721 (FIGS. 57 and 60) of the inferior body portion 720.

Figure 65:
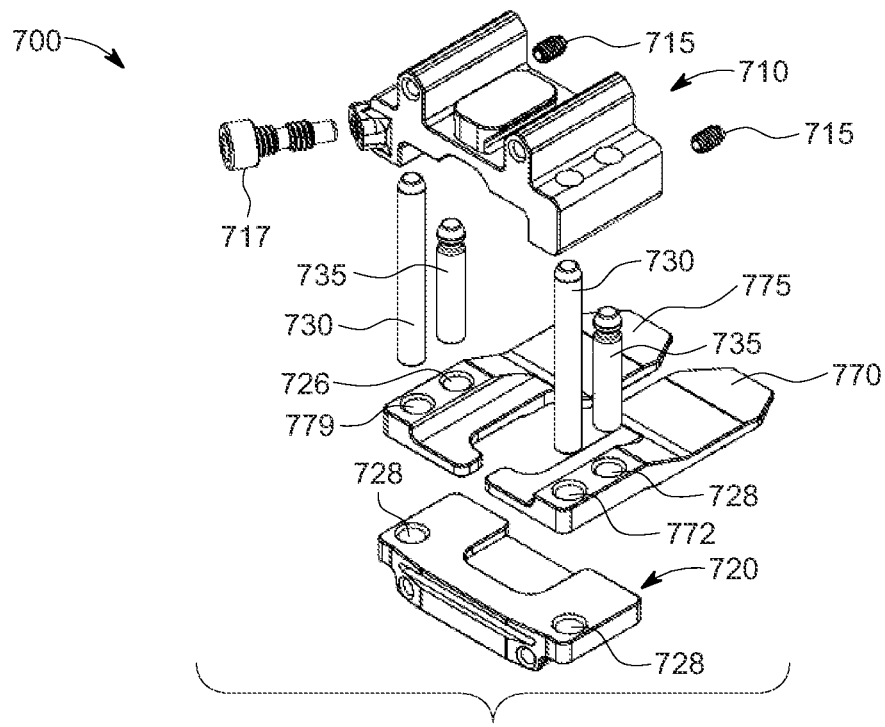
FIG. 65 is an exploded top perspective view of the decoupled resection guide of FIG. 57, according to an embodiment of the present disclosure.
Figure 66:
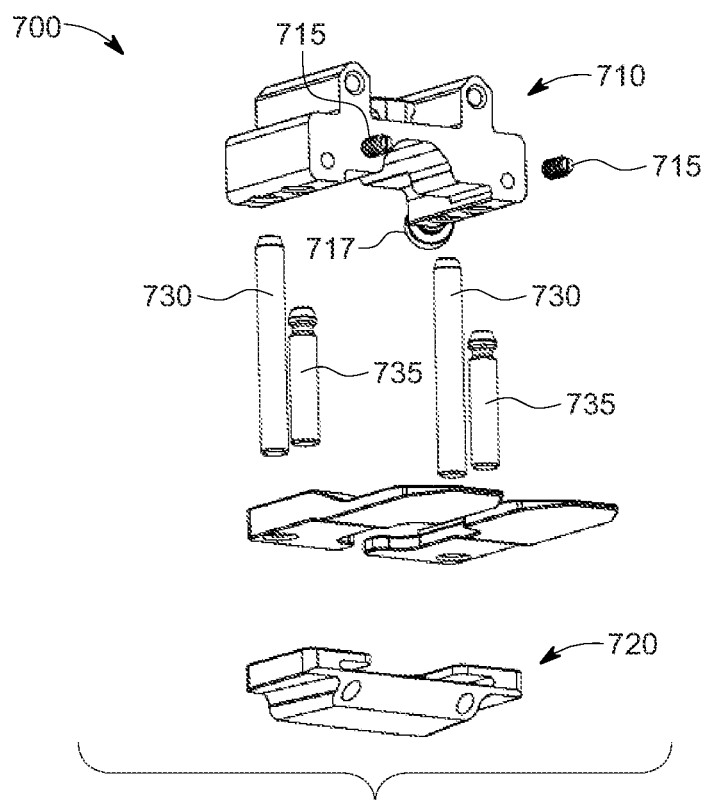
FIG. 66 is an exploded bottom perspective view of the decoupled resection guide of FIG. 57, according to an embodiment of the present disclosure.

The decoupled talar resection guide 700 may include the posteriorly-extending separately and independently movable talar paddles 770 and 775. For example, the decoupled talar resection guide 700 may include a plurality of posteriorly-extending talar paddles such as the first posteriorly-extending talar paddle 770 and the second posteriorly-extending talar paddle 775. The talar paddles 770 and 775 are operable to allow a surgeon to place a downward or an inferiorly directed force onto the talus during distraction. With reference to FIGS. 65 and 66, the connecting members 730 may have inferior ends fixedly securable in respective recessed holes 728 in the inferior body portion 720. The connecting members 735 may have inferior ends fixedly securable in recessed holes 726 and 728 in a different one of the talar paddles 770 and 775. The movable talar paddles 770 and 775 have corresponding through-holes 772 and 779 so that talar paddles 770 and 775 may be slidably movable on connecting members 730. The superior body portion 710 may include a thumb screw 717 operable for locking superior body portion 710 to one of the connecting members 730 and maintaining the distal portion of a patient's tibia relative to the patient's talus in tension. A plurality of set screws 715 may also secure superior body portion 710 to connecting members 735.

With reference again to FIGS. 57 and 58, spacers 790 and 795 allow for making the amount of bone resected from the talus variable. Spacers 790 and 795 may include cutouts 791 and 796 sized for extending around connecting member 730, and tabs 793 and 797 for use by a surgeon in grasping the spacers. For example, the spacers may be disposed against surface 721 of inferior body portion 720 and inferior surfaces of movable talar paddles 770 and 775. Talar paddles 770 and 775 provide independent paddles for tensioning soft tissue medially and laterally, as well as correcting talus deformities. Operably attaching the decoupled talar resection guide 700 to the patient allows for correcting deformity of the talus relative to the pre-op planning alignment protocol with the alignment guide.

With reference again to FIG. 57, a coupler 750 may be attached to the superior body portion 710 for connecting the superior body portion to the alignment system 10 (FIG. 1). For example, the coupler 750 may be a flaring tenon that slides into a mortise in the alignment system 10 (FIG. 1), e.g., forming a dovetail joint.

Figure 67:
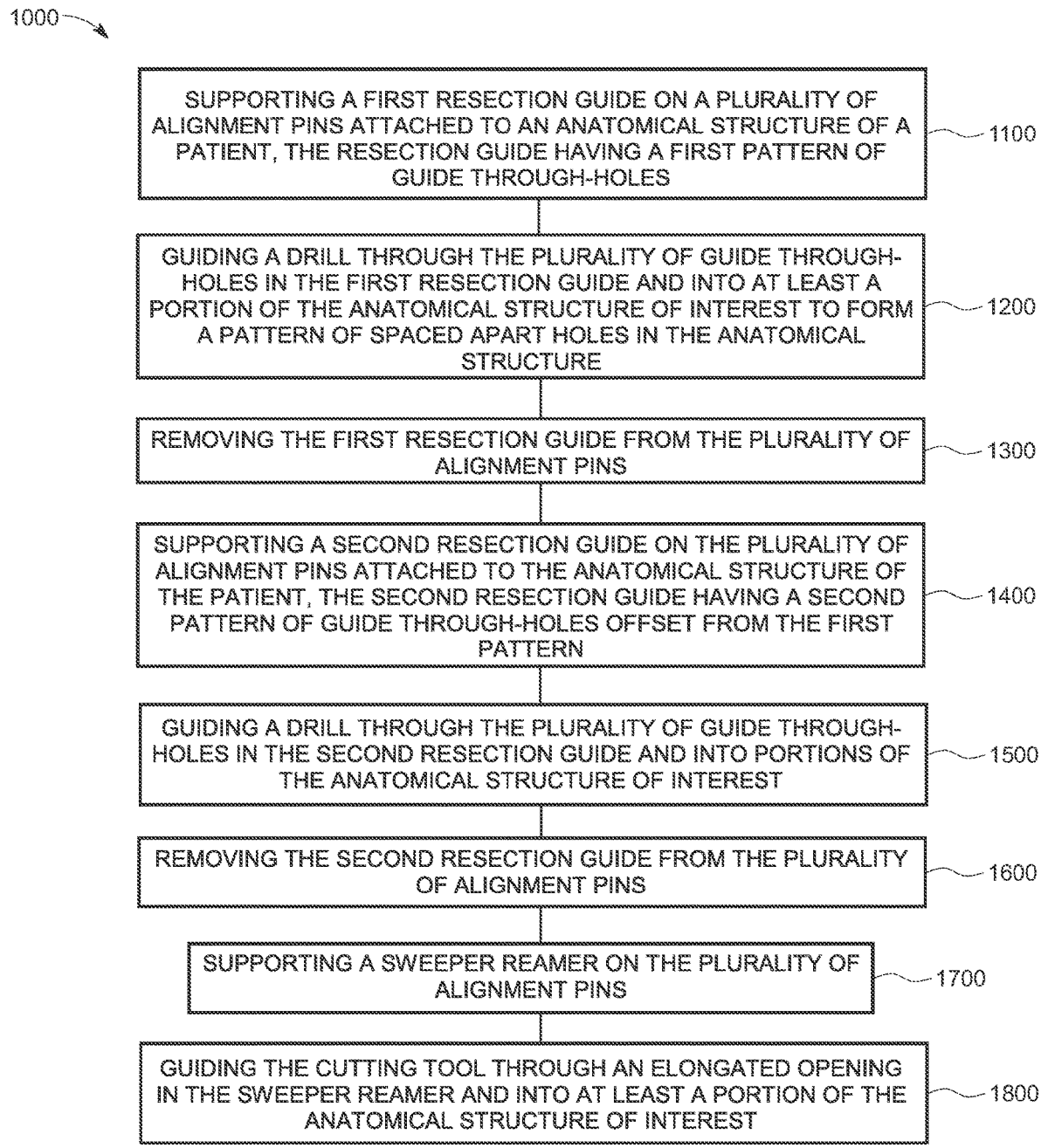
FIG. 67 is a flowchart of a surgical method, according to an embodiment of the present disclosure.
Figure 68:
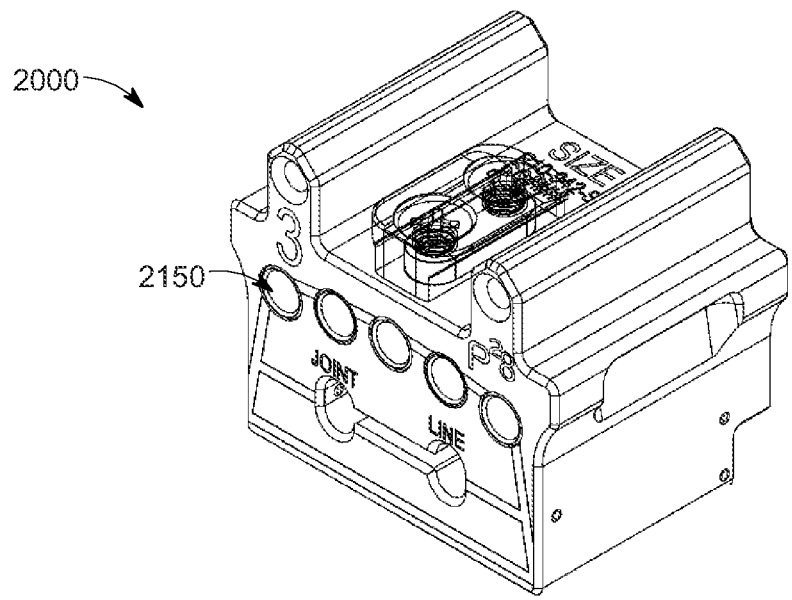
FIG. 68 is a top perspective view of a resection guide, according to an embodiment of the present disclosure.
Figure 69:
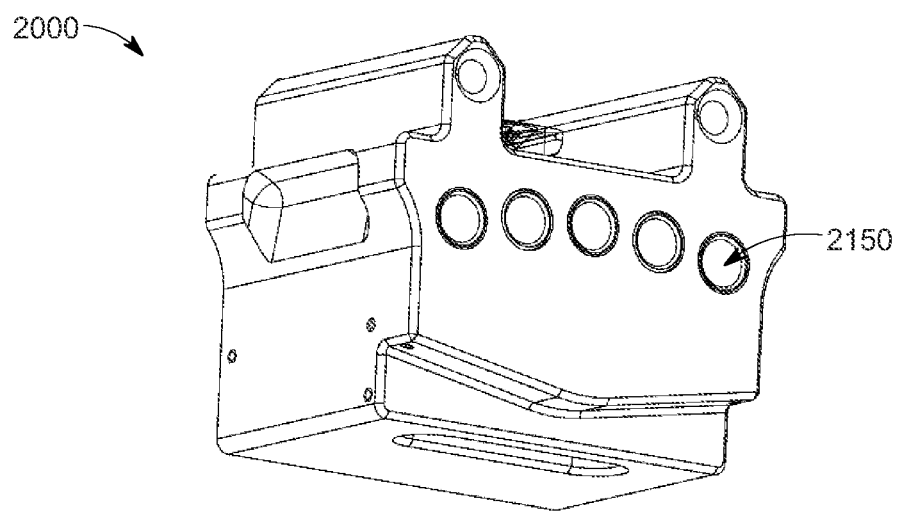
FIG. 69 is a bottom perspective view of the resection guide of FIG. 68, according to an embodiment of the present disclosure.
Figure 70:
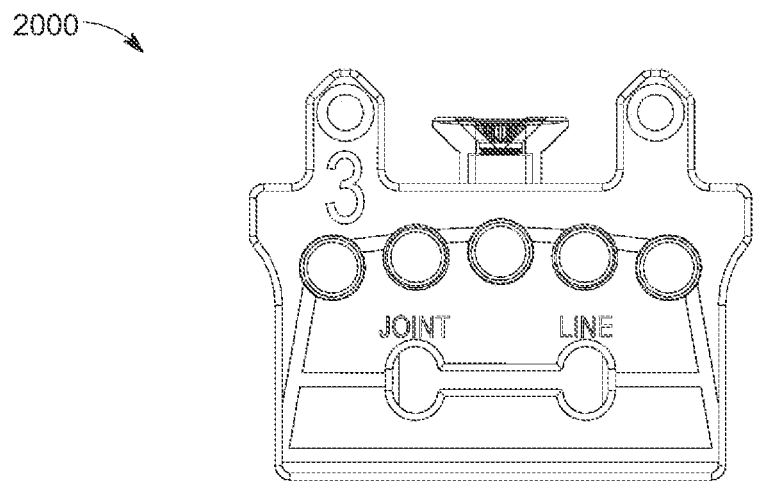
FIG. 70 is a front view of the resection guide of FIG. 68, according to an embodiment of the present disclosure.
Figure 71:
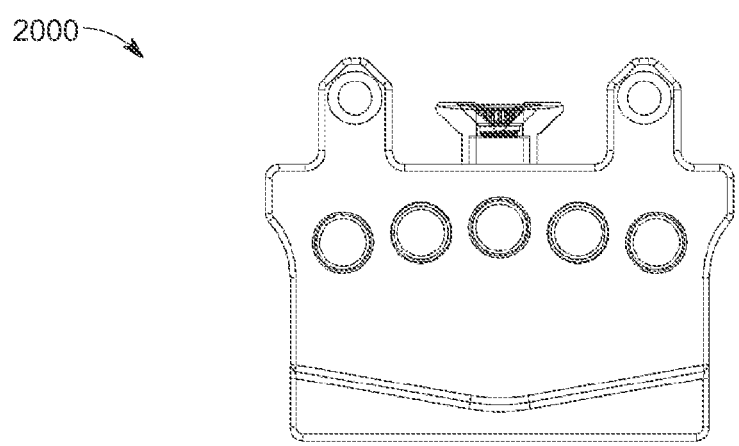
FIG. 71 is a rear view of the resection guide of FIG. 68, according to an embodiment of the present disclosure.
Figure 72:
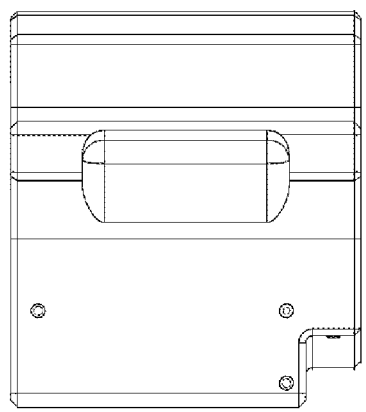
FIG. 72 is a right side view of the resection guide of FIG. 68, according to an embodiment of the present disclosure.
Figure 73:
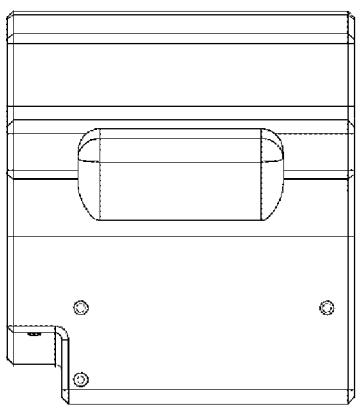
FIG. 73 is a left side view of the resection guide of FIG. 68, according to an embodiment of the present disclosure.
Figure 74:
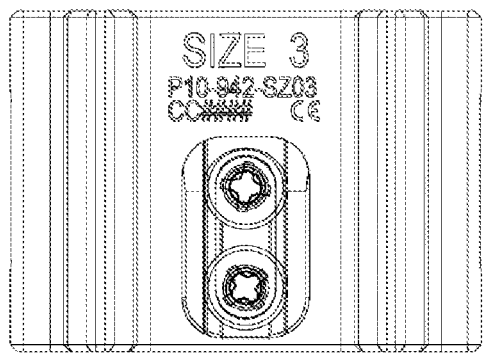
FIG. 74 is a top view of the resection guide of FIG. 68, according to an embodiment of the present disclosure.
Figure 75:
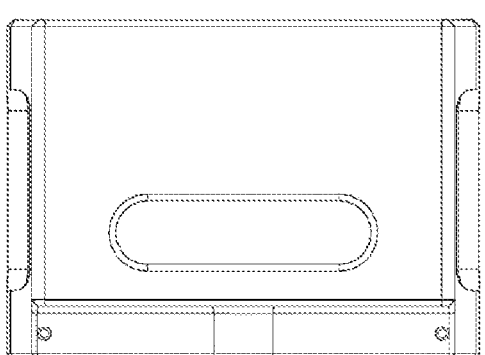
FIG. 75 is a bottom view of the resection guide of FIG. 68, according to an embodiment of the present disclosure.

FIG. 67 illustrates a surgical method 1000, according to the present disclosure. For example, surgical method 1000 includes at 1100 supporting a first resection guide on a plurality of alignment pins attached to an anatomical structure of a patient, the resection guide having a first pattern of guide through-holes, at 1200 guiding a drill through the plurality of guide through-holes in the first resection guide and into at least a portion of the anatomical structure of interest to form a pattern of spaced apart holes in the anatomical structure.

The surgical method 1000 may further include at 1300 removing the first resection guide from the plurality of alignment pins, at 1400 supporting a second resection guide on the plurality of alignment pins attached to the anatomical structure of the patient, the second resection guide having a second pattern of guide through-holes offset from the first pattern, and at 1500 guiding a drill through the plurality of guide through-holes in the second resection guide and into portions of the anatomical structure of interest.

The surgical method 1000 may further include at 1600 removing the second resection guide from the plurality of alignment pins, at 1700 supporting a sweeper reamer on the plurality of alignment pins, and at 1800 guiding the cutting tool through an elongated opening in the sweeper reamer and into at least a portion of the anatomical structure of interest.

FIGS. 68-75 and 76-83 illustrate resection guides 2000 and 3000, respectively, which are operable sequentially for use in resecting a distal portion of the tibia and a superior portion of the talus, according to an embodiment of the present disclosure. Exemplary resection guides 2000 and 3000 are operable for use with a plurality of alignment pins fixedly attached to a patient for resecting at least a portion of an anatomical structure of interest. For example, the resection guides 2000 and 3000 may include offset and overlapping patterns of guide through-holes for use with a drill and side slots for use with a cutting tool in forming a tibia arc resection of a patient's tibia for use in a total ankle repair. In these illustrated embodiments, resection guide 3000 may also be a coupled tibial and talar resection guide for use in also resecting a patient's talus for use in a total ankle repair. The resection guides 2000 and 3000 may be configured in a plurality of different matching size arcs to allow a surgeon to selectively choose the correct sized pair of resection guides based on the anatomical configuration of a patient specific tibia and talus such as, for example, selected corresponding to the selected sizing template 30 (FIG. 1) for initially aligning the alignment pins.

With reference to FIGS. 68-75, the resection guide 2000 may be essentially the same as resection guide 100 (FIGS. 3-10) with the exception of a single series of drill holes 2150 (no side or lowermost inferior medial and lateral drill holes) extending along an arc and no inferior or talar alignment pin through-holes.

Figure 76:
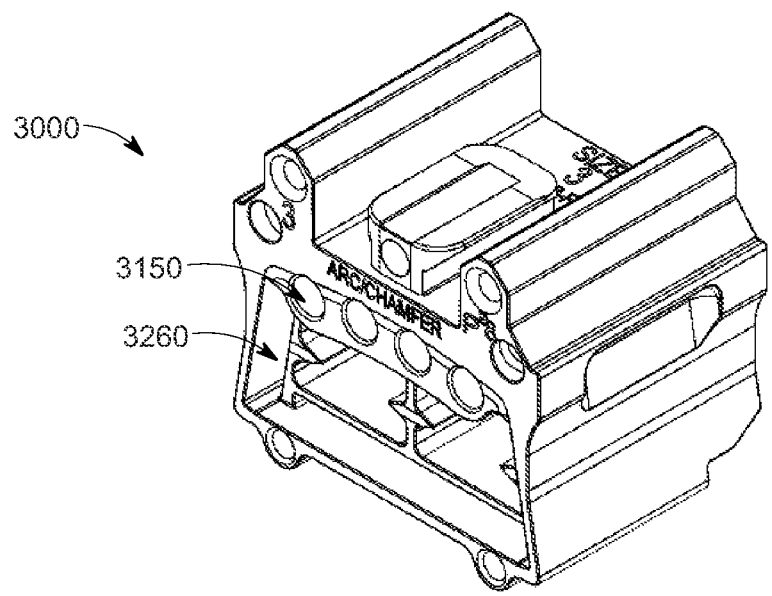
FIG. 76 is a top perspective view of a resection guide, according to an embodiment of the present disclosure.
Figure 77:
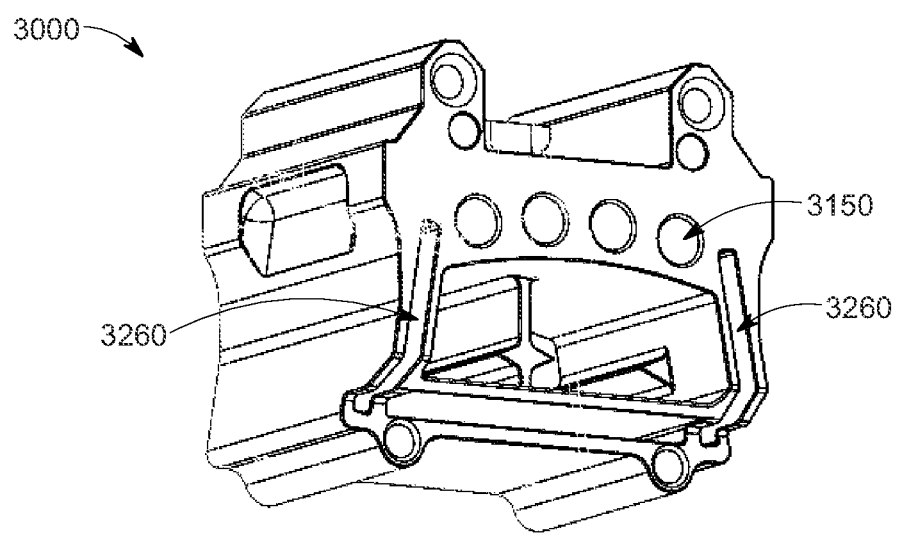
FIG. 77 is a bottom perspective view of the resection guide of FIG. 76, according to an embodiment of the present disclosure.
Figure 78:
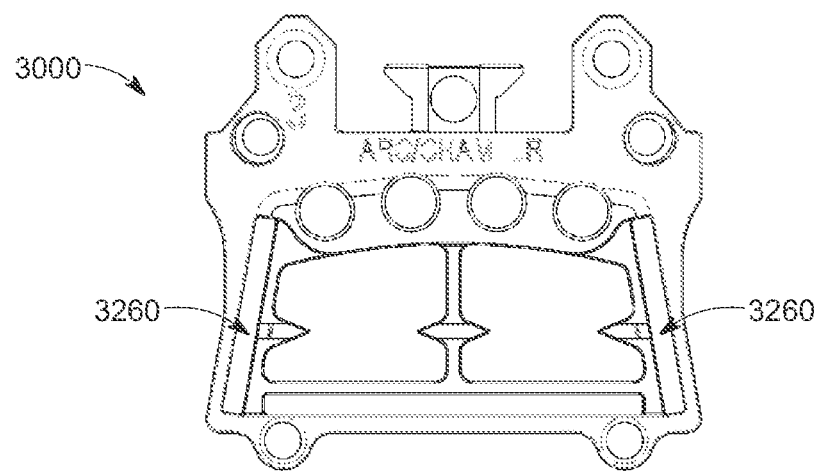
FIG. 78 is a front view of the resection guide of FIG. 76, according to an embodiment of the present disclosure.
Figure 79:
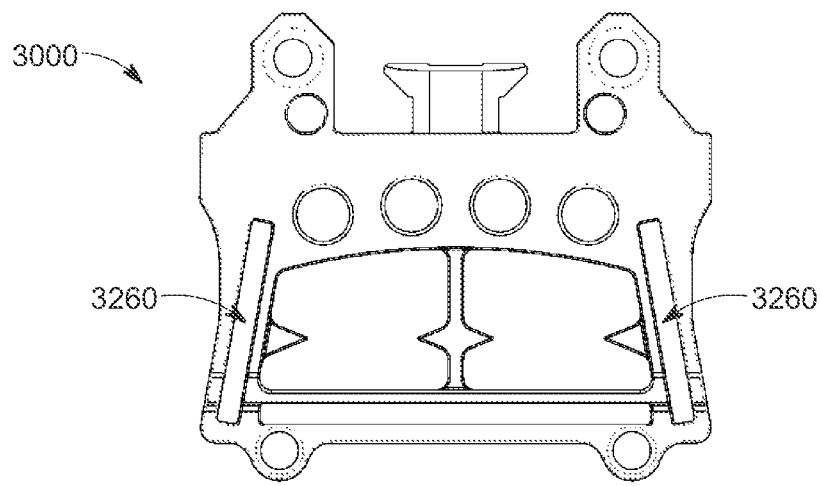
FIG. 79 is a rear view of the resection guide of FIG. 76, according to an embodiment of the present disclosure.
Figure 80:
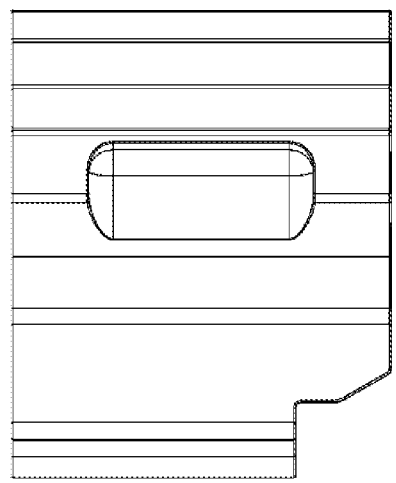
FIG. 80 is a right side view of the resection guide of FIG. 76, according to an embodiment of the present disclosure.
Figure 81:
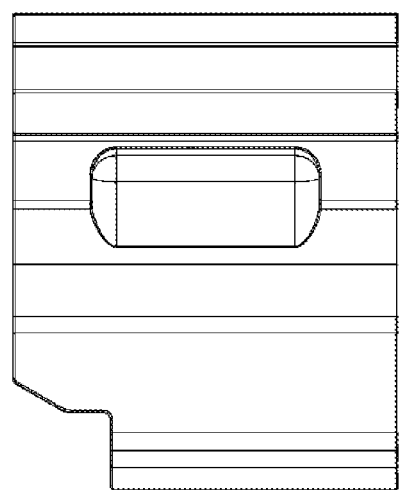
FIG. 81 is a left side view of the resection guide of FIG. 76, according to an embodiment of the present disclosure.
Figure 82:
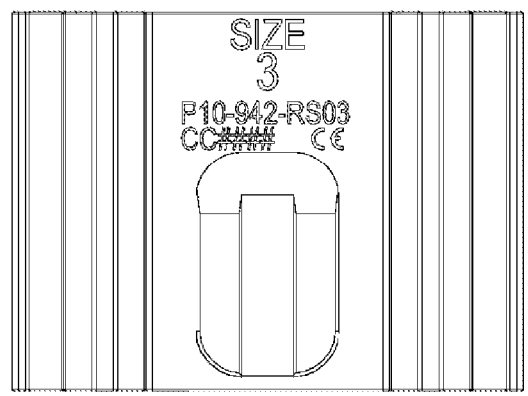
FIG. 82 is a top view of the resection guide of FIG. 76, according to an embodiment of the present disclosure.
Figure 83:
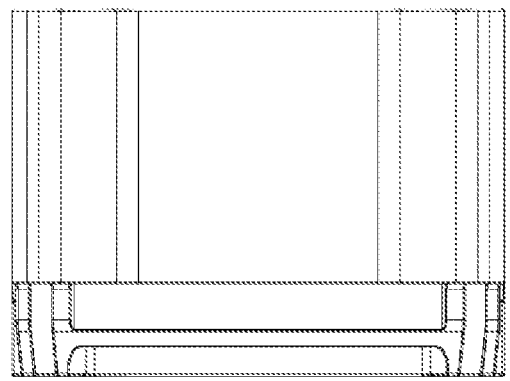
FIG. 83 is a bottom view of the resection guide of FIG. 76, according to an embodiment of the present disclosure.

With reference to FIGS. 76-83, the resection guide 3000 may be essentially the same as resection guide 200 (FIGS. 11-18) with the exception of a single series of drill holes 3150 as shown in FIGS. 76 and 77 extending along an arc (no side or lowermost inferior medial and lateral drill holes). As best shown in FIGS. 76-79, medial and lateral angled side slots 3260 extend from a first side to a second side of the resection guide 3000. A cutting tool may be suitably employed for resecting the sides for the tibial cutout.

Figure 84:
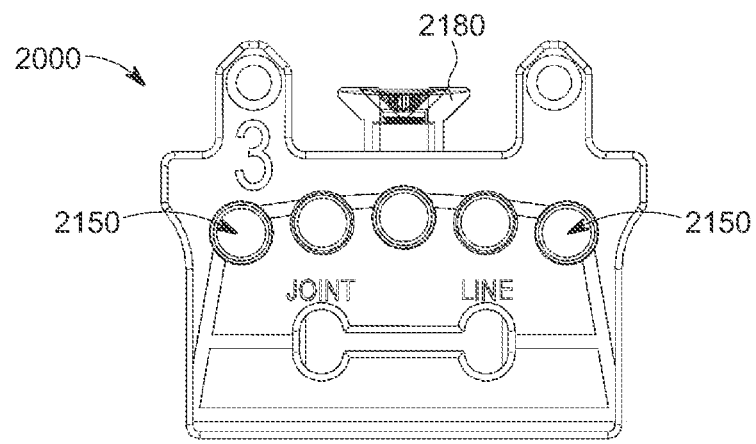
FIG. 84-86 are front views of the resection guide of FIG. 68, the resection guide of FIG. 76, and superimposed front views of the resection guide of FIG. 68 and the resection guide of FIG. 76, according to an embodiment of the present disclosure.

With reference to FIG. 84, the resection guide 2000 may be employed and aligned and positioned on a plurality of pins or guide wires 35 (FIG. 1) attached to a proximal portion of a tibia of a patient. If the alignment system 10 is also attached to the tibia of the patient, the resection guide 2000 may also be operable attached to the alignment system via a coupler 2180. Using a drill, a surgeon may initially form a series of holes via the guide through holes 2150 in the tibia to initiate a resection of the distal portion of the tibia. Thereafter, the resection guide 2000 is removed.

Figure 85:
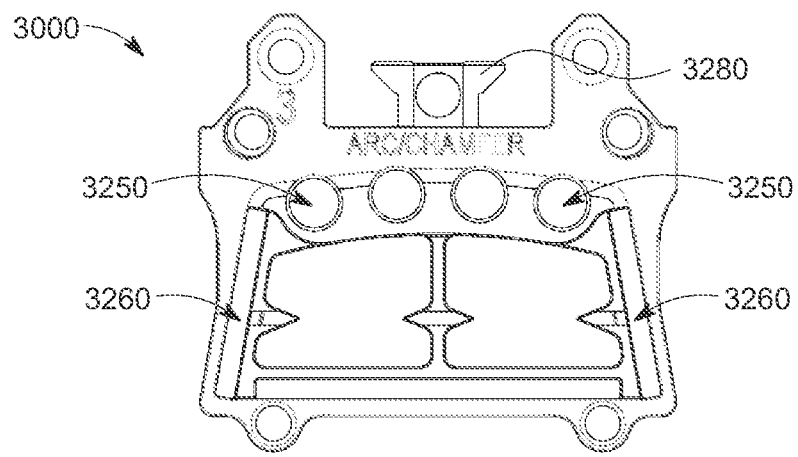

With reference to FIG. 85, the resection guide 3000 may then be employed and aligned and positioned on the plurality of pins or guide wires 35 (FIG. 1) attached to a proximal portion of the tibia of the patient and aligned and positioned on a plurality of pins or guide wires 37 (FIG. 1) attached to a talus of the patient. If the alignment system 10 is also attached to the tibia of the patient, the resection guide 3000 may also be operable attached to the alignment system via the coupler 3280. Using a drill, a surgeon may next form a series of holes via the guide holes through holes 3250 to continue the resection of the distal portion of the tibia. Using a cutting tool in the side slots 3260, the surgeon can then form the medial and lateral sides of the resection of the distal portion of the tibia. The superior portion of the side slots 3260 aligning with the medial most and lateral most drill holes 2150 (FIG. 84).

Figure 86:
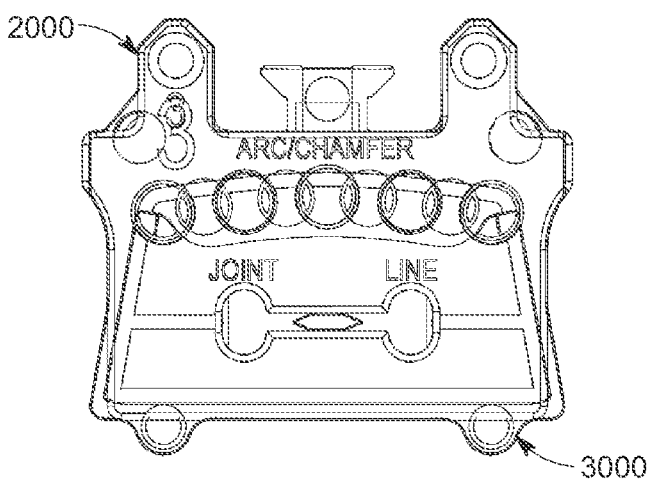

As shown in FIG. 86, the use of the resection guide 2000 followed by use of the resection guide 3000 results in a series of overlapping drilled holes and formed slots in the tibia of the patient having an inverted arcuate cutout or tibia arc resection along the distal portion of the tibia of the patient. The sweeping reamer 300 (FIG. 25) may then be employed to clean the resected surface due to the overlapping drilled holes. In other embodiments, the initially resected tibia may be cleaned using an arc osteotome or chisel, an arc rasp having a curved surface, or other suitable tools (not shown).

Figure 87:
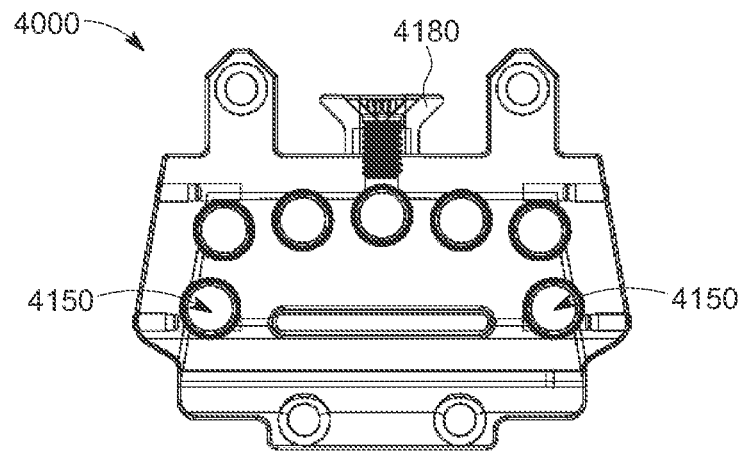
FIG. 87-89 are front views of the resection guide of FIG. 68, the resection guide of FIG. 76, and superimposed front views of the resection guide of FIG. 3 and the resection guide of FIG. 76, according to an embodiment of the present disclosure.

With reference to FIG. 87, a resection guide 4000 may be employed and aligned and positioned on a plurality of pins or guide wires 35 (FIG. 1) attached to a proximal portion of a tibia of a patient, and aligned and positioned on a plurality of pins or guide wires 37 (FIG. 1) attached to a talus of the patient. If the alignment system 10 is also attached to the tibia of the patient, the resection guide 4000 may also be operable attached to the alignment system via a coupler 4180. Using a drill, a surgeon may initially form a series of holes via the guide through holes 4150 in the tibia to initiate a resection of the distal portion of the tibia. Thereafter, the resection guide 4000 is removed.

Figure 88:
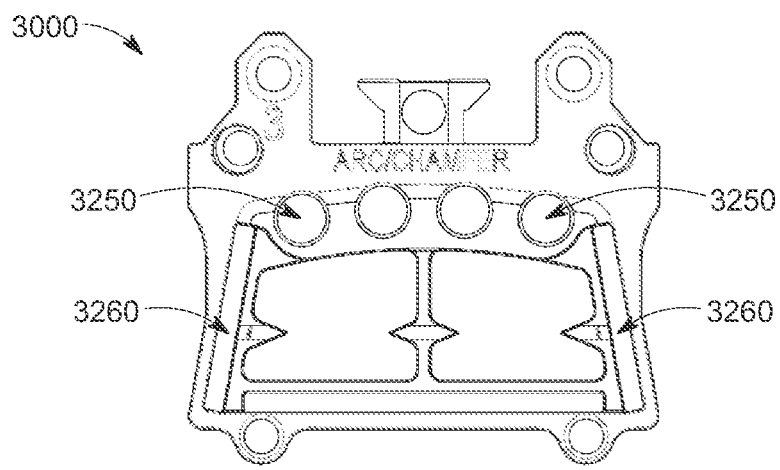

With reference to FIG. 88, the resection guide 3000 may then be employed and aligned and positioned on the plurality of pins or guide wires 35 (FIG. 1) attached to a proximal portion of the tibia of the patient and aligned and positioned on a plurality of pins or guide wires 37 (FIG. 1) attached to a talus of the patient. If the alignment system 10 is also attached to the tibia of the patient, the resection guide 3000 may also be operable attached to the alignment system via the coupler 3280. Using a drill, a surgeon may next form a series of holes via the guide holes through holes 3250 to continue the resection of the distal portion of the tibia. Using a cutting tool in the side slots 3260, the surgeon can then form the medial and lateral sides of the resection of the distal portion of the tibia. The superior portion of the side slots 3260 aligning with the medial most and lateral most drill holes 4150 (FIG. 87).

Figure 89:
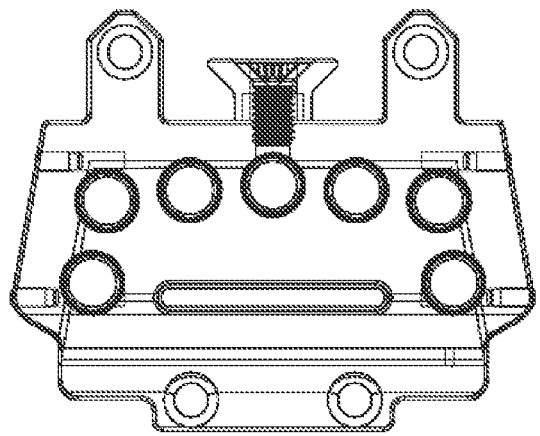
Figure 90:
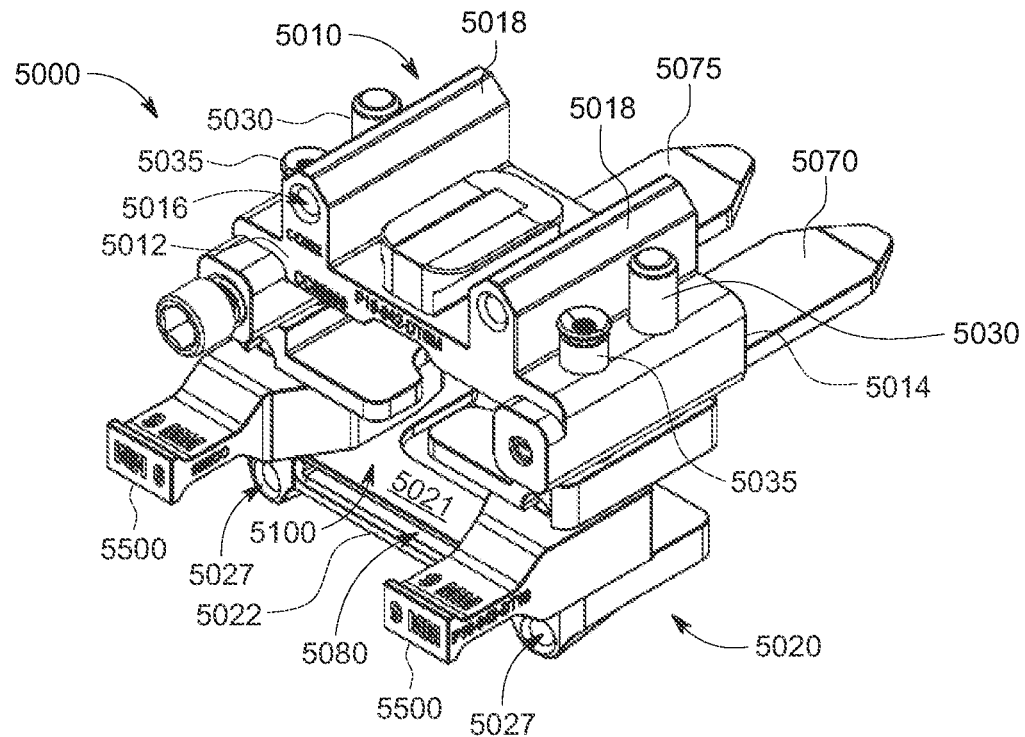
FIG. 90 is a top perspective view of a decoupled resection guide, according to an embodiment of the present disclosure.
Figure 91:
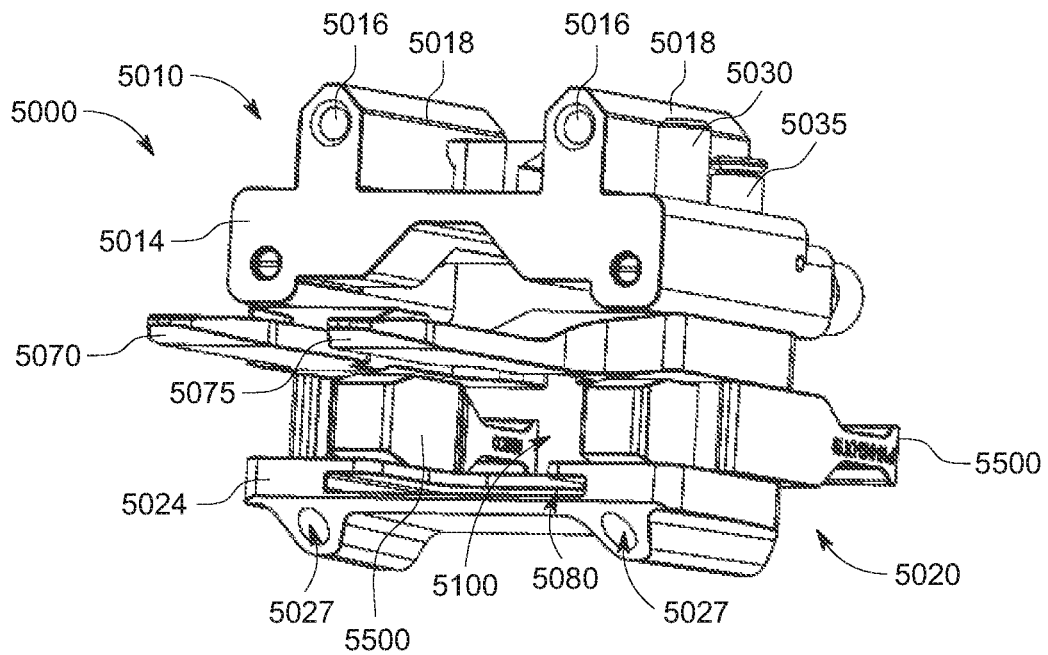
FIG. 91 is a bottom perspective view of the decoupled resection guide of FIG. 90, according to an embodiment of the present disclosure.
Figure 92:
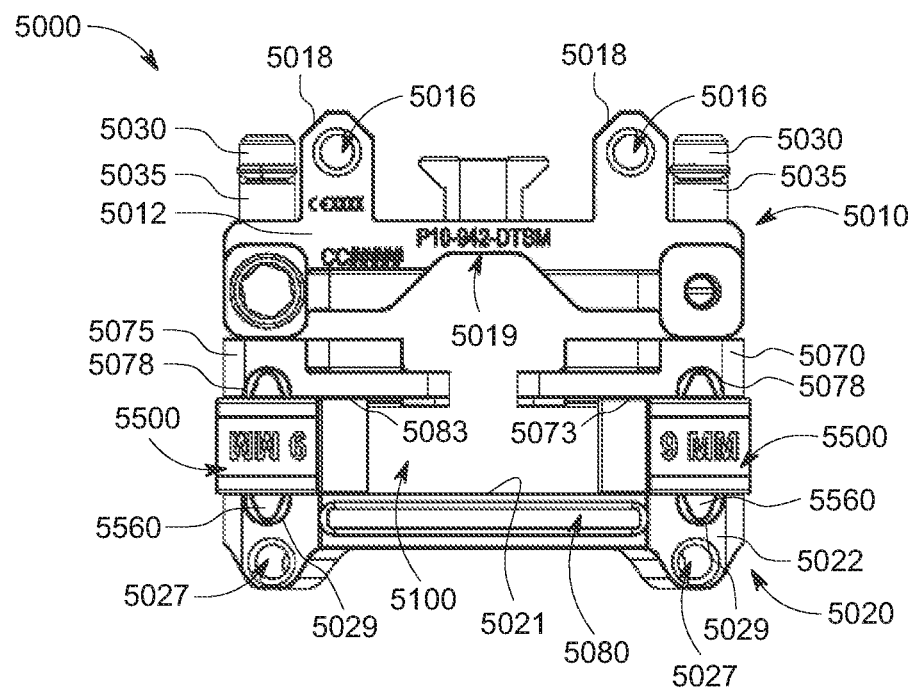
FIG. 92 is a front elevational view of the decoupled resection guide of FIG. 90, according to an embodiment of the present disclosure.
Figure 93:
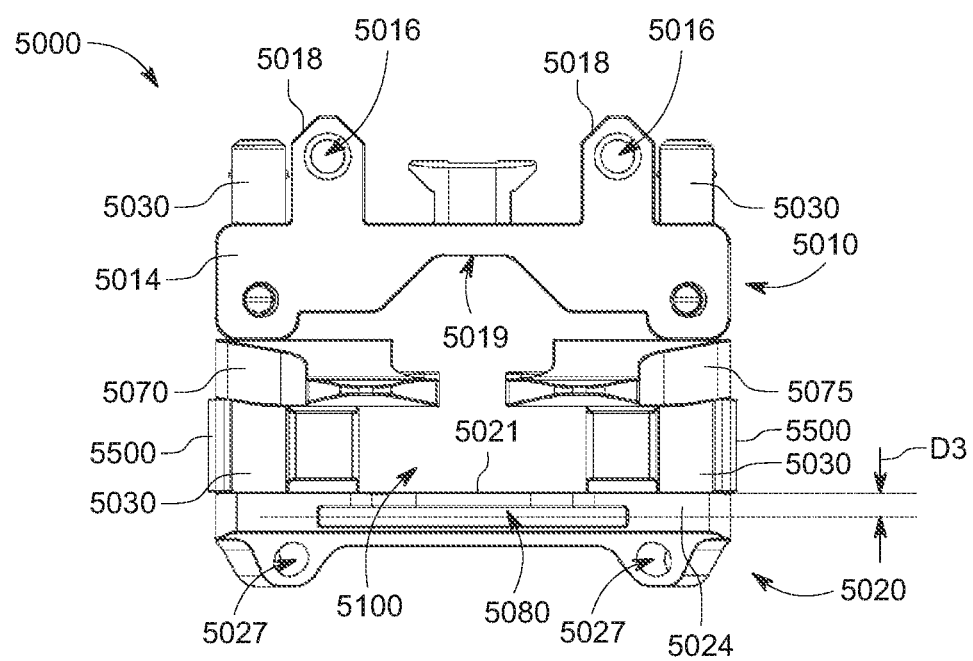
FIG. 93 is a rear elevational view of the decoupled resection guide of FIG. 90, according to an embodiment of the present disclosure.
Figure 94:
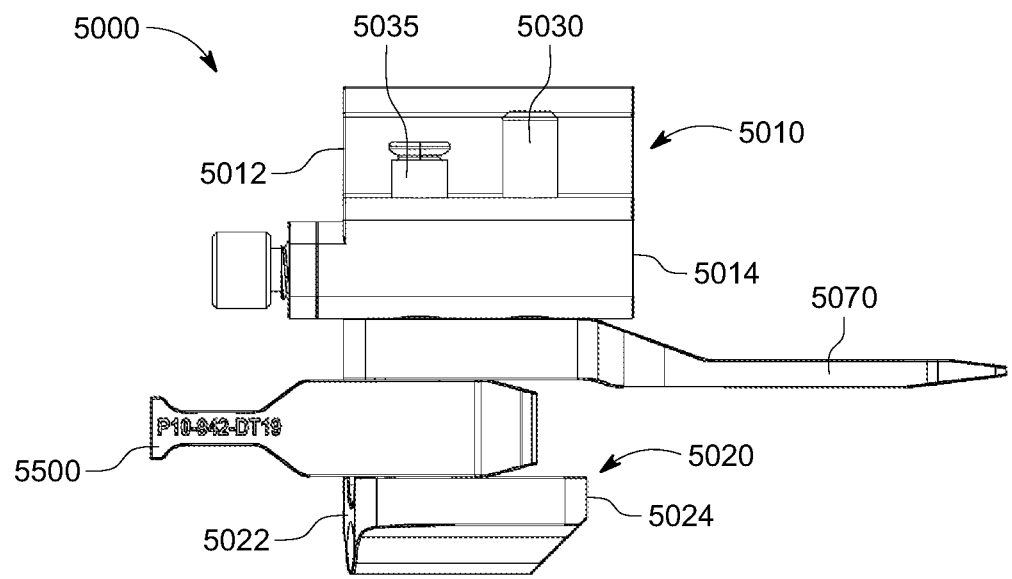
FIG. 94 is a right side elevational view of the decoupled resection guide of FIG. 90, according to an embodiment of the present disclosure.
Figure 95:
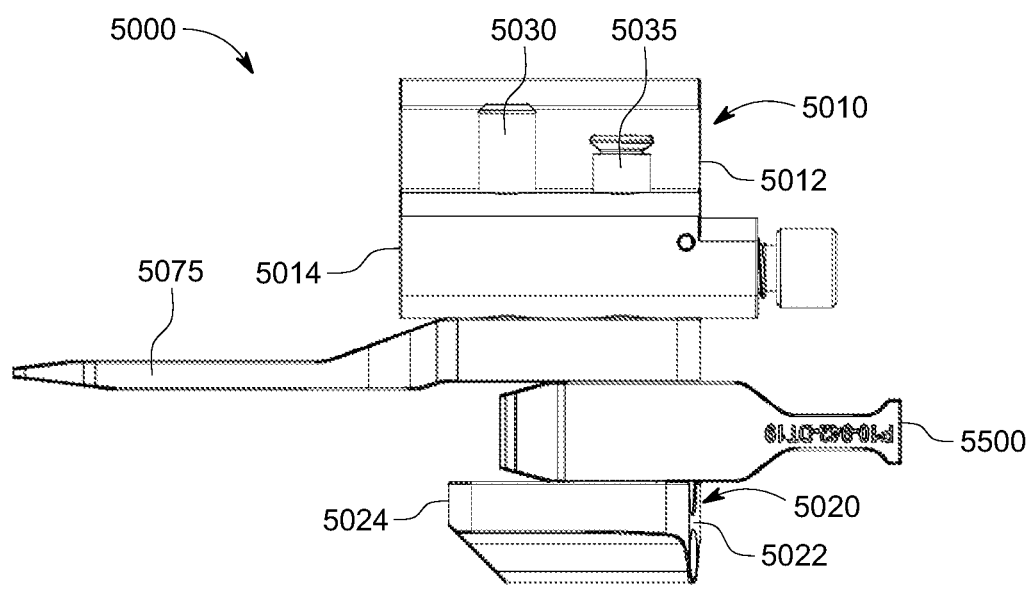
FIG. 95 is a left side elevational view of the decoupled resection guide of FIG. 90, according to an embodiment of the present disclosure.
Figure 96:
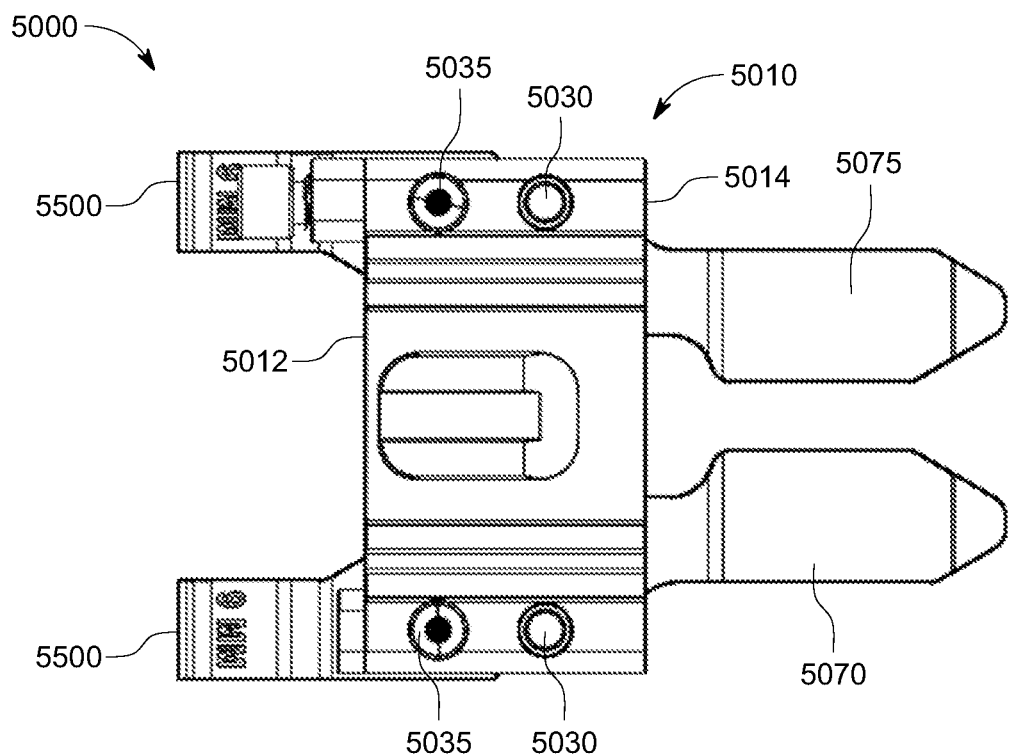
FIG. 96 is a top view of the decoupled resection guide of FIG. 90, according to an embodiment of the present disclosure.
Figure 97:
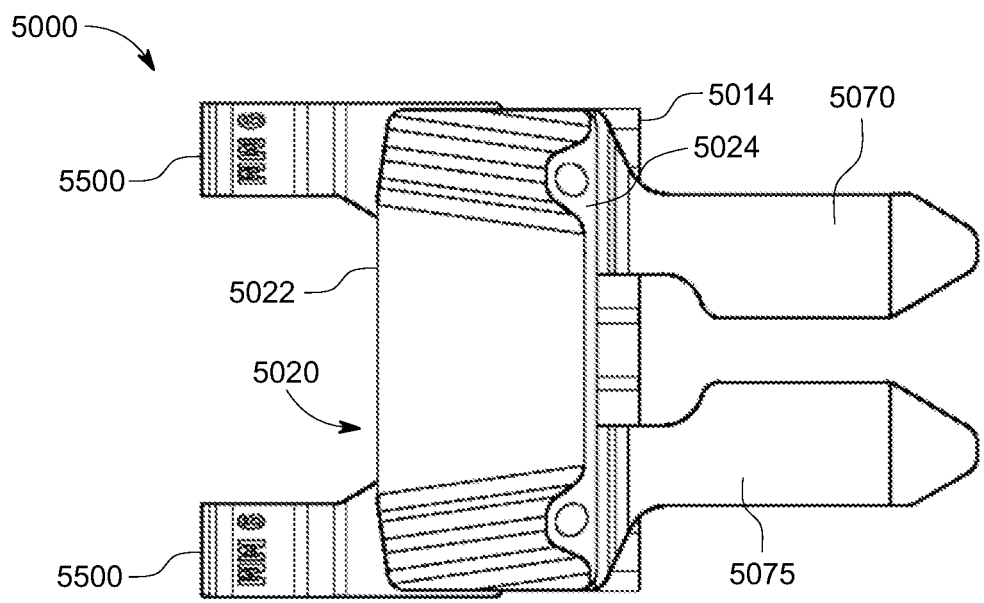
FIG. 97 is a bottom view of the decoupled resection guide of FIG. 90, according to an embodiment of the present disclosure.

As shown in FIG. 89, the use of the resection guide 4000 followed by use of the resection guide 3000 results in a series of overlapping drilled holes and formed slots in the tibia of the patient having an inverted arcuate cutout or tibia arc resection along the distal portion of the tibia of the patient. The sweeping reamer 300 (FIG. 25) may then be employed to clean the resected surface due to the overlapping drilled holes. In other embodiments, the initially resected tibia may be cleaned using an arc osteotome or chisel, an arc rasp having a curved surface, or other suitable tools (not shown).

FIGS. 90-99 illustrate a decoupled talar resection guide 5000, according to an embodiment of the present disclosure. As an alternative option to a coupled talar resection guide, for example, the coupled tibial and talar resection guides 200 and 400, a surgeon is able to use the decoupled talar resection guide 5000 to place different amounts of tension on the medial and lateral soft tissue between the talus and the tibia of the patient. In ankle joints with varus-valgus deformities, this can allow the surgeon to straighten the ankle to provide a horizontal cut in the talus.

With reference to FIGS. 90-97, the decoupled talar resection guide 5000 may include a superior body portion 5010 having a first side 5012 and an opposite second side 5014, an inferior body portion 5020 having a first side 5022 and an opposite second side 5024, connecting pins 5030 and 5035 for operably connecting the superior body portion 5010 to the inferior body portion 5020, a plurality of paddles 5070 and 5075, and a first spacer 5500 and a second spacer 5500. The connecting pins 5030 and 5035 are operable to movably connect the superior body portion 5010 to the inferior body portion 5020 and restrain the paddles 5070 and 5075 therebetween.

As described below and as best shown in FIGS. 90-93, the first spacer 5500 and the second spacer 5500 are spaced apart and provide an opening or viewing window 5100 therebetween to allow a surgeon to observe and ensure that the paddles properly engage the talus.

The superior body portion 5010 may include a plurality of alignment pin through-holes 5016 extending from the first side to the second side of the body 5010 to define a pattern of alignment pin through-holes 5016 with openings opening onto the first side of the body and openings opening onto the second side of the body. The plurality of alignment pin through-holes 5016 may be parallel to each other. The two alignment pin through-holes 5016 may be disposed in superiorly-extending tabs 5018 extending from superior body portion 5010. The superior body portion 5010 may have an arched cutout 5019 (best shown in FIGS. 92 and 93) extending from the first side 5012 to the opposite second side 5014.

As will be appreciated, alignment pin through-holes 5016 of the decoupled talar resection guide 5000 may match the locations of the alignment pin through-holes in the resection guides 100, 200, and 400 so as to be usable with the same alignment pins and system used to initially resect the tibia. In some embodiments, the alignment pin through-holes 5016 (FIG. 90) may be 2.4 mm diameter pin holes.

With reference still to FIGS. 90-93, the inferior body portion 5020 may include a plurality of talus fixation pin through-holes 5027 extending from the first side to the second side of the body with openings opening onto the first side of the body and openings opening onto the second side of the body. The medial and lateral talus fixation pin through-holes 5027 may be disposed at different anterior to posterior angles. For example, the talus fixation pin through-holes 5027 may be angled to guide fixation pins toward each other and into the patient's talus. The inferior body portion 5020 may include an elongated guide slot 5080 for resecting the talus. The center of the elongated guide slot 5080 is spaced a distance D3 (FIG. 93) from a surface 5021 (FIGS. 90 and 93) of the inferior body portion 5020.

The decoupled talar resection guide 5000 may include the posteriorly-extending separately and independently movable talar paddles 5070 and 5075. For example, the decoupled talar resection guide 5000 may include a plurality of posteriorly-extending talar paddles such as the first posteriorly-extending talar paddle 5070 and the second posteriorly-extending talar paddle 5075. The talar paddles 5070 and 5075 are operable to allow a surgeon to place a downward or an inferiorly directed force onto the talus during distraction.

Figure 98:
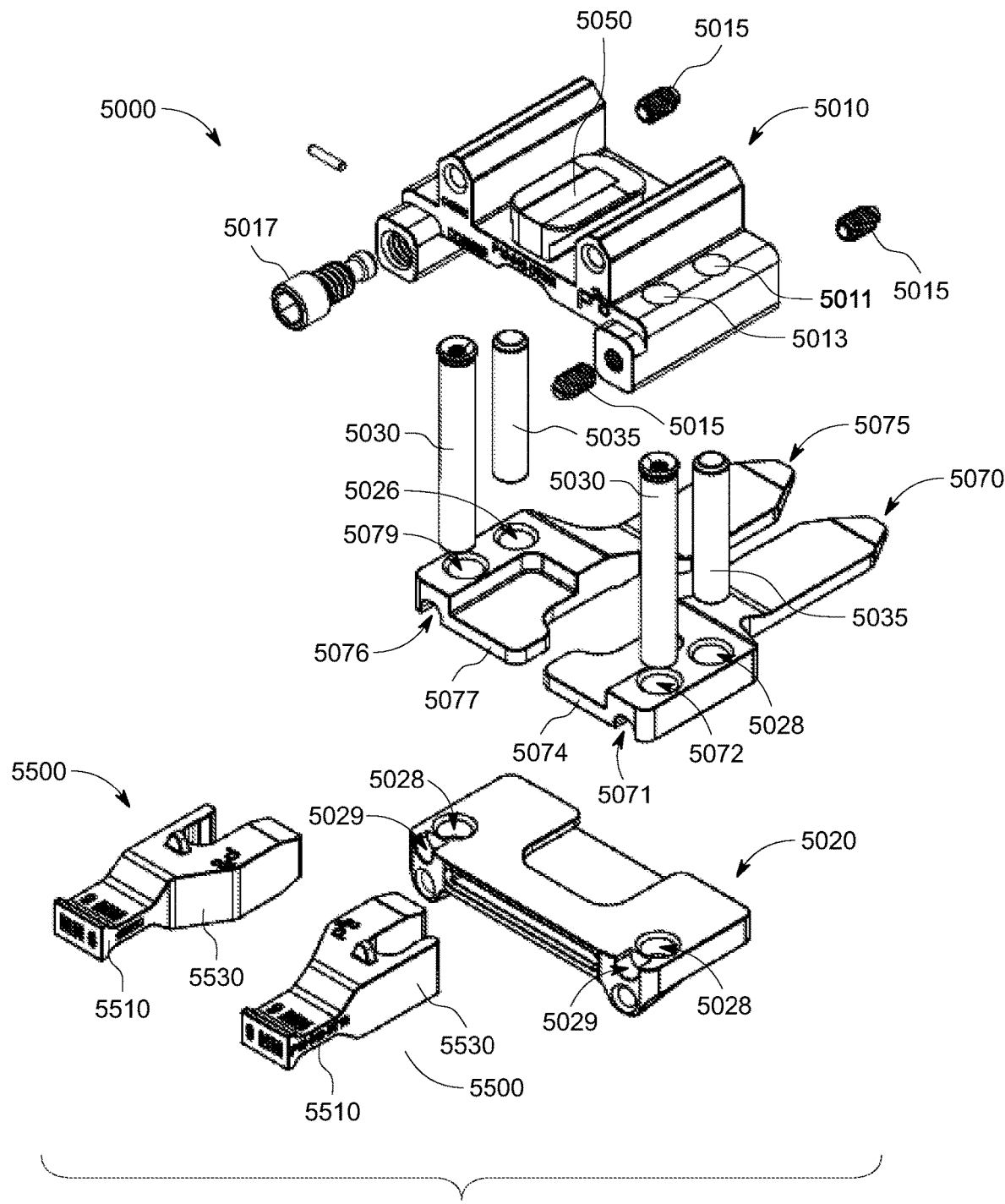
FIG. 98 is an exploded top perspective view of the decoupled resection guide of FIG. 90, according to an embodiment of the present disclosure.
Figure 99:
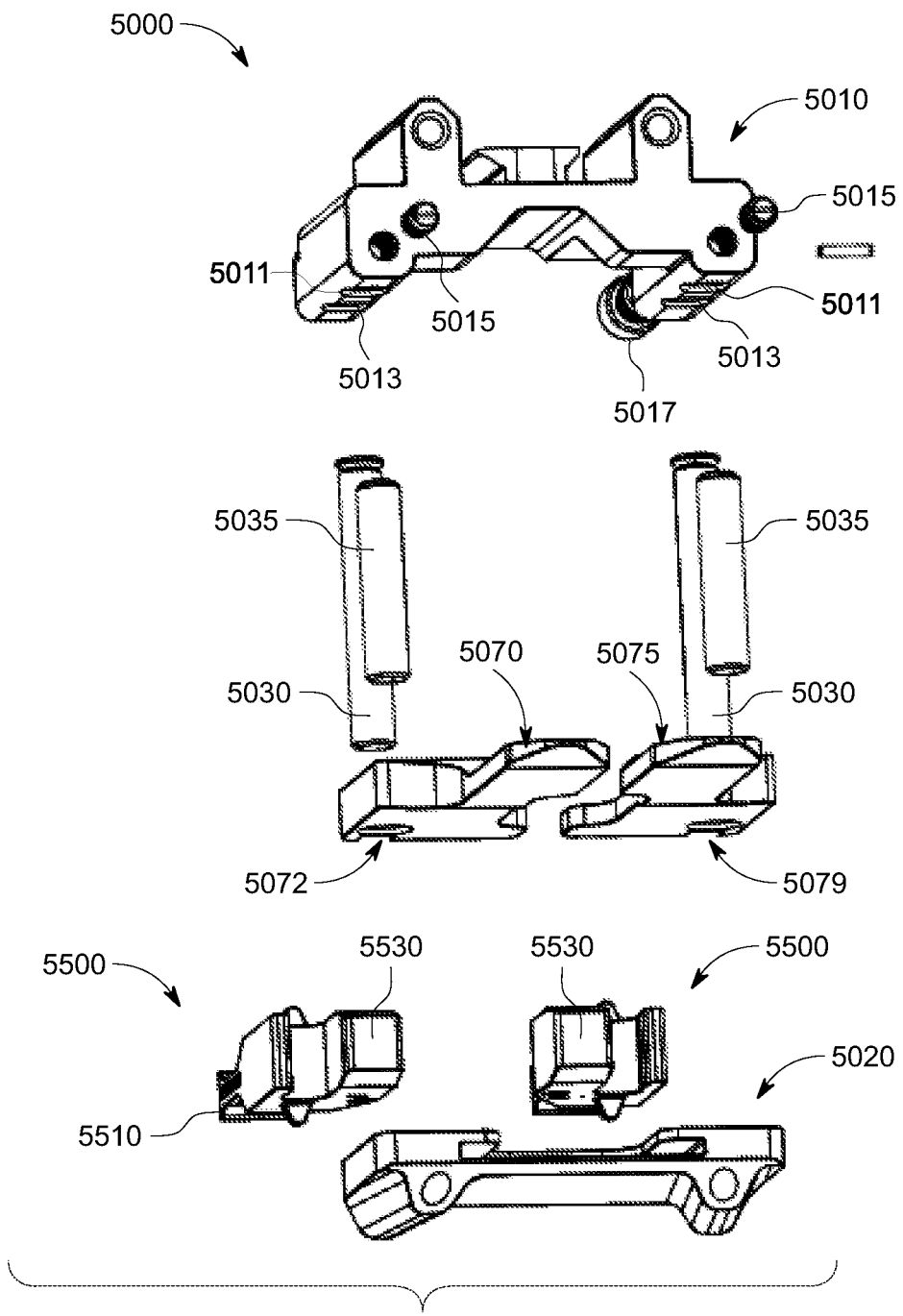
FIG. 99 is an exploded bottom perspective view of the decoupled resection guide of FIG. 90, according to an embodiment of the present disclosure.

With reference to FIGS. 98 and 99, the connecting members 5030 may have inferior ends fixedly securable in respective recessed holes 5028 (FIG. 98) in the inferior body portion 5020. The connecting members 5035 may have inferior ends fixedly securable in recessed holes 5026 (FIG. 98) and 5028 (FIG. 98) in a different one of the talar paddles 5070 and 5075. The movable talar paddles 5070 and 5075 have corresponding through-holes 5072 and 5079 so that talar paddles 5070 and 5075 may be slidably movable on the connecting members 5030. The superior body portion may include through holes 5011 and 5013 sized for slidably receiving connecting members 5030 and 5035. The superior body portion 5010 may include a thumb screw 5017 operable for locking superior body portion 5010 to one of the connecting members 5030 and maintaining the distal portion of a patient's tibia relative to the patient's talus in tension. A plurality of set screws 5015 may also secure superior body portion 5010 to connecting members 5030 and 5035.

Figure 100:
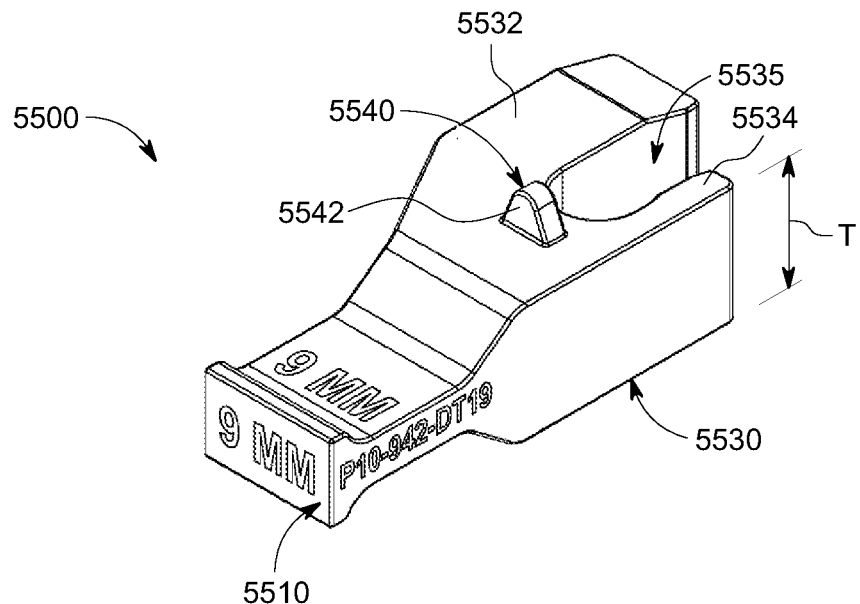
FIG. 100 is an enlarged top perspective view of the spacer of FIG. 90.
Figure 101:
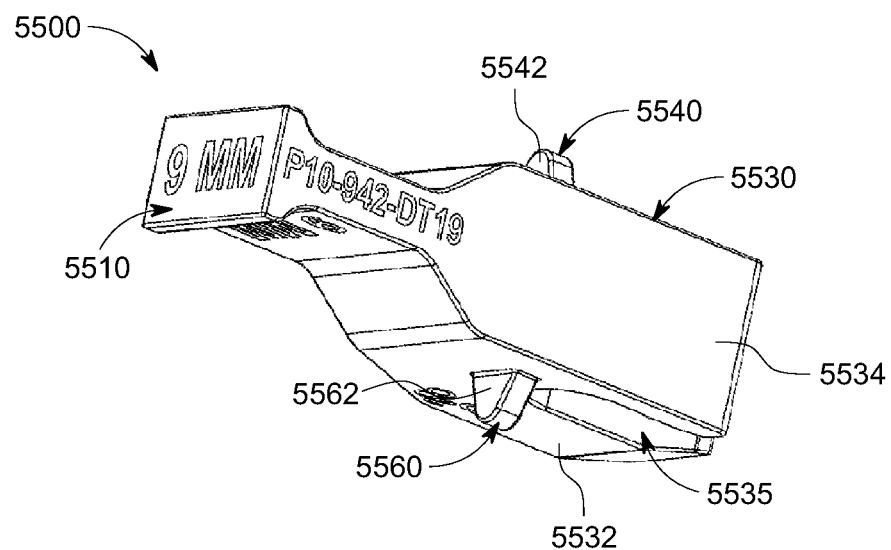
FIG. 101 is an enlarged bottom perspective view of the spacer of FIG. 100.
Figure 104:
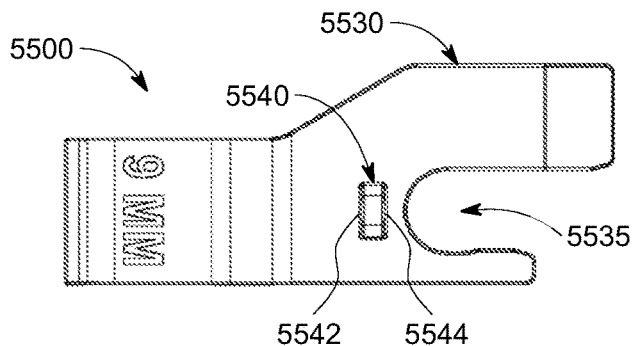
FIG. 104 is a top view of the spacer of FIG. 100.
Figure 102:
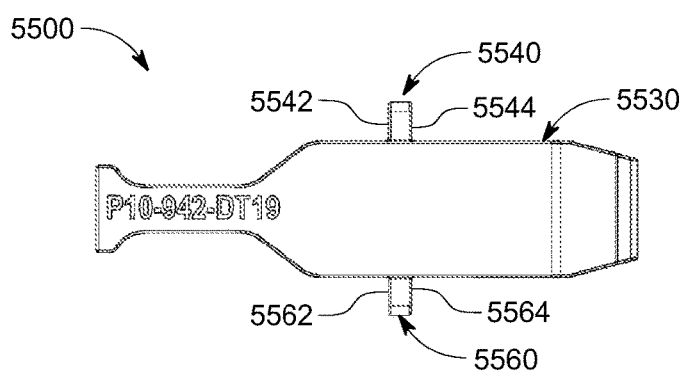
FIG. 102 is a right side elevational view of the spacer of FIG. 100.
Figure 103:
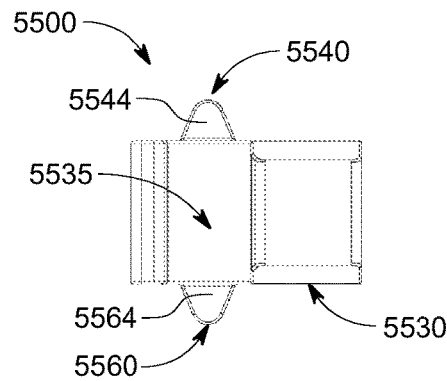
FIG. 103 is a rear elevational view of the spacer of FIG. 100.
Figure 105:
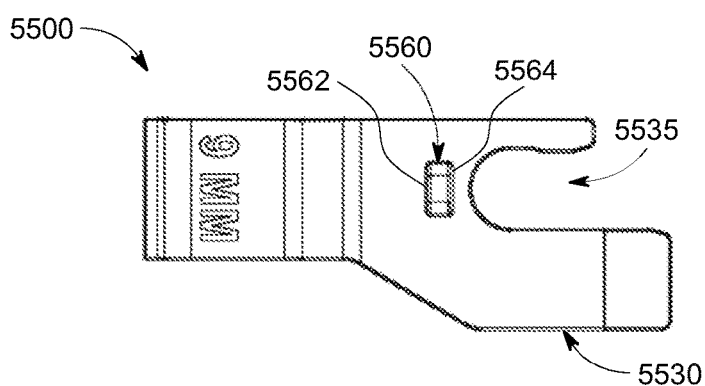
FIG. 105 is a bottom view of the spacer of FIG. 100.

With reference still to FIGS. 98 and 99, the spacers 5500 allow for making the amount of bone resected from the talus variable. Spacers 5500 may include a handle portion 5510 and a U-shaped portion 5530. The handle portion 5510 is operable by a surgeon in grasping the spacers 5500. The U-shaped portion 5530 is configured for extending around one of the connecting members 5030. As shown in FIGS. 100 and 101, the handle portion 5510 of the spacer 5500 may include indicia indicating the thickness T (FIG. 100) of the U-shaped portion 5530 of the spacer 5500. The U-shaped portion 5030 may include a first leg 5532 and a second leg 5534 which define a cavity 5535 therebetween sized to allow the U-shaped portion 5530 to be positioned around connecting member 5030 (FIG. 98). The first leg 5532 may be sized wider or thicker than the second leg 5534.

With reference to FIGS. 102-105, the U-shaped portion 5030 of the spacers 5500 may include a superior alignment tab 5540 and an inferior alignment tab 5560. The superior alignment tab 5540 may be generally triangular shaped having an anterior surface 5542 and a posterior surface 5544. The inferior alignment tab 5540 may be generally triangular shaped having an anterior surface 5562 and a posterior surface 5564. The alignment tabs 5540 and 5560 may be aligned with the cavity 5535 of the U-shaped portion 5530 of the spacer 5500. The superior alignment tab 5540 cooperates with the inferior body portion, and the inferior alignment tab 5560 cooperates with the talar paddles to aid in maintaining the spacers 5500 in position.

As shown in FIG. 98, the inferior body portion 5020 includes cutouts 5029 on the opposite second side 5024, which cutouts 5029 are aligned with connecting members 5030. The talar paddle 5070 includes a cutout 5071 on an anterior surface 5074 of talar paddle 5070, which cutout 5071 is aligned with the corresponding connecting members 5030. The talar paddle 5075 includes a cutout 5076 on an anterior surface 5077 of talar paddle 5070, which cutout 5076 is aligned with the corresponding connecting members 5030.

As will be appreciated, the first spacer 5500 and the second spacer 5500 are spaced apart and provide an opening or viewing window 5100 therebetween to allow a surgeon to observe and ensure that the paddles properly engage the talus. For example, the spacers 5500 may have a thickness, and a plurality of pairs the spacers may be provided and available in different thicknesses.

Figure 106:
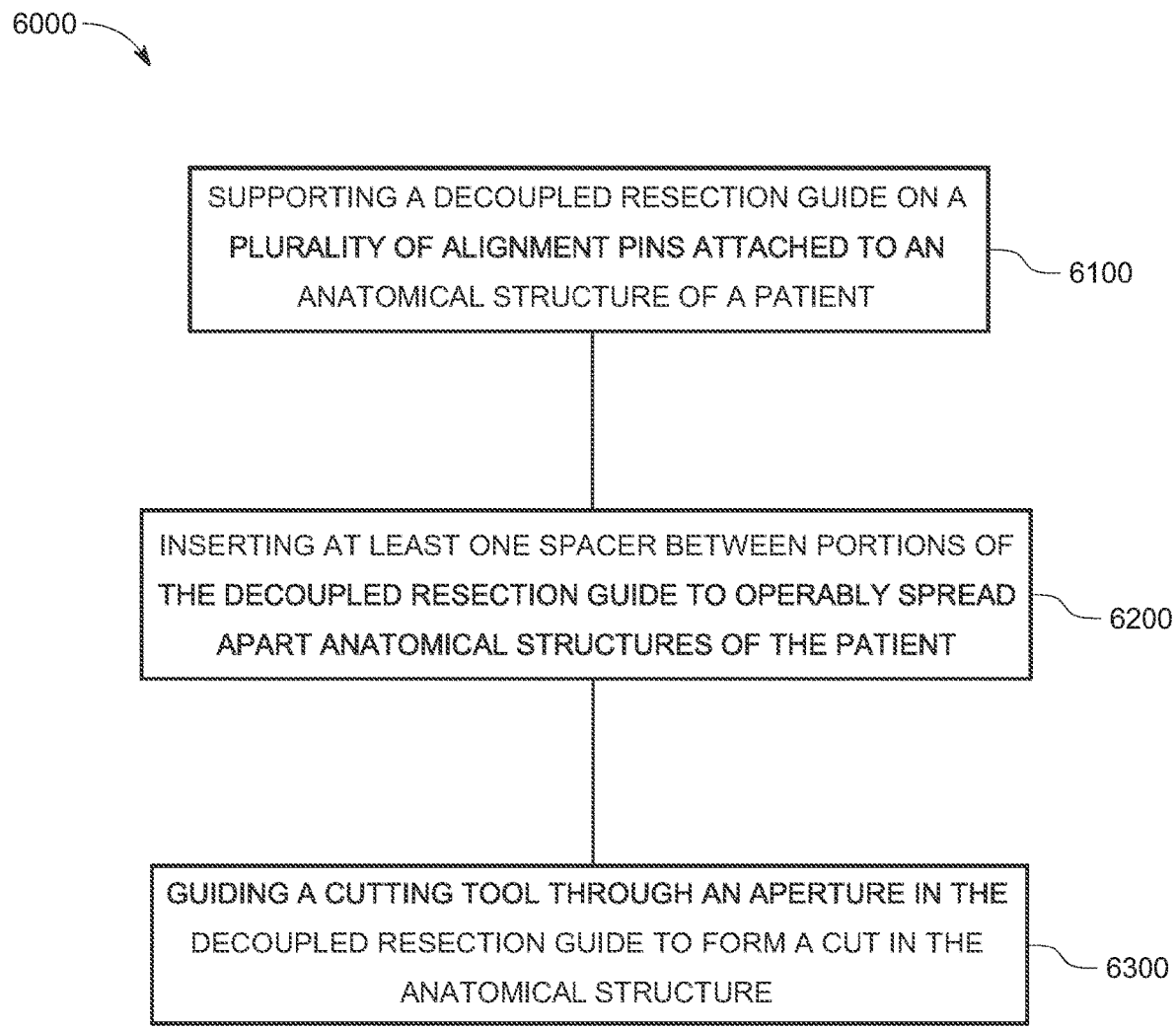
FIG. 106 is a flowchart of a surgical method, according to an embodiment of the present disclosure.

FIG. 106 illustrates a surgical method 6000, according to the present disclosure. For example, surgical method 6000 includes at 6100 supporting a decoupled resection guide on a plurality of alignment pins attached to an anatomical structure of a patient, at 6200 inserting at least one spacer between portions of the decoupled resection guide to operably spread apart anatomical structures of the patient; and at 6300 guiding a cutting tool through an aperture in the decoupled resection guide to form a cut in the anatomical structure.

The above disclosure describes a portion of a total ankle replacement (TAR) procedure and the devices used in that procedure.

The above disclosure describes a portion of a total ankle replacement (TAR) procedure and the devices used in that procedure. Additional understanding of the TAR procedure may be found in U.S. Provisional Application No. 62/779,436 filed Dec. 13, 2018, and entitled Joint Replacement Systems and Methods of Use and Assembly, International Application No. PCT/US2019/029009 filed Apr. 24, 2019, and entitled Implants and Methods of Use and Assembly, U.S. Provisional Application No. 62/779,092 filed Dec. 13, 2018, and entitled Instruments, Guides and Related Methods for Total Ankle Replacement, International Application No. PCT/US2019/066404 filed Dec. 13, 2019, and entitled Instruments, Guides and Related Methods for Total Ankle Replacement, U.S. Provisional Application No. 62/890,611 filed Aug. 22, 2019, and entitled Patient Specific Instruments and Methods of Use, International Application No. PCT/US2019/066336 filed Dec. 13, 2019, and entitled Patient Specific Instruments and Methods of Use, U.S. Provisional Application No. 62/899,703 filed Sep. 12, 2019, and entitled Joint Replacement Alignment Guides, Systems and Methods of Use and Assembly, International Application No. PCT/US2019/066408 filed Dec. 13, 2019, and entitled Joint Replacement Alignment Guides, Systems and Methods of Use and Assembly, U.S. Provisional Patent Application No. 62/899,655, filed Sep. 12, 2019, and entitled Alignment Instruments And Methods For Use In Total Ankle Replacement, International Application No. PCT/US2019/066149, filed on Dec. 13, 2019, and entitled Alignment Instruments And Methods For Use In Total Ankle Replacement, U.S. Provisional Application No. 62/899,740 filed Sep. 12, 2019, and entitled Joint Replacement Alignment Guides, Systems and Methods of Use and Assembly, International Application No. PCT/US2019/066393 filed Dec. 13, 2019, and entitled Joint Replacement Alignment Guides, Systems and Methods of Use and Assembly, U.S. Provisional Application No. 62/898,615 filed Sep. 11, 2019, and entitled Resection Guides, Sweeping Reamers, and Methods for Use in Total Ankle Replacement, International Application No. PCT/US2019/064948 filed Dec. 6, 2019, and entitled Resection Guides, Sweeping Reamers, and Methods for Use in Total Ankle Replacement, U.S. Provisional Application No. 62/898,854 filed Sep. 11, 2019, and entitled Distractors Having Attachable Paddles, Impaction Devices, and Methods for Use in Total Ankle Replacement, International Application No. PCT/US2019/066398 filed Dec. 13, 2019, and entitled Distractors Having Attachable Paddles, Impaction Devices, and Methods for Use in Total Ankle Replacement, U.S. Provisional Application No. 62/899,646 filed Sep. 12, 2019, and entitled Trial Insert Assembly, International Application No. PCT/US2019/065025 filed Dec. 6, 2019, and entitled Trial Insert Assembly, U.S. Provisional Application No. 62/899,460 filed Sep. 12, 2019, and entitled Total Ankle Replacement Surgical Method, International Application No. PCT/US2019/066409 filed Dec. 13, 2019, and entitled Total Ankle Replacement Surgical Method, which are each hereby incorporated herein in their entireties.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features. Any examples of parameters are not exclusive of other parameters of the disclosed embodiments.

As used herein, the terms "comprising," "has," "including," "containing," and other grammatical variants thereof encompass the terms "consisting of" and "consisting essentially of." The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Where one or more ranges are referred to throughout this specification, each range is intended to be a shorthand format for presenting information, where the range is understood to encompass each discrete point within the range as if the same were fully set forth herein.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments.

Components, aspects, features, configurations, arrangements, uses and the like described, illustrated or otherwise disclosed herein with respect to any particular embodiment may be similarly applied to any other embodiment disclosed herein. Accordingly, the inventions are not to be seen as limited by the foregoing description, but is only limited by the scope of the appended claims.

This written description uses examples to disclose the inventions, including the best mode, and also to enable any person skilled in the art to practice the inventions, including making and using any devices or systems and performing any incorporated methods. The patentable scope of the inventions are defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A resection system, comprising:
    a drill guide, comprising:
        at least one through hole extending from a first side of the drill guide through to a second side of the drill guide; and
    a resection guide, comprising:
        at least one cut slot extending from a first side of the resection guide through to a second side of the resection guide;
        at least one support pin configured to releasably couple at least one of the drill guide and the resection guide with a bone of a patient;
        at least one first aperture disposed on an upper portion thereof and extending from the first side through to the second side, wherein the at least one first aperture is configured to receive a first support pin of the at least one support pin at least partially therethrough;
        wherein the resection guide comprises at least one second aperture disposed on an upper portion thereof and extending from the first side through to the second side, wherein the at least one second aperture is configured to receive a second support pin of the at least one support pin at least partially therethrough;
        wherein the at least one through hole comprises a plurality of holes configured in an arcuate pattern and configured to receive at least a portion of a drill at least partially therethrough;
        wherein the drill guide and the resection guide each comprise a coupling element extending from an upper portion thereof, wherein the coupling element is configured to releasably couple with an alignment guide of the resection system so as to indirectly couple the drill guide and the resection guide with a bone of a patient.

2. The resection system of claim 1, wherein:
    the at least one support pin comprises a pair of support pins;
    the at least one first aperture comprises a pair of first apertures; and
    the at least one second aperture comprises a pair of second apertures.

3. The resection system of claim 1, wherein the at least one cut slot comprises a plurality of cut slots, wherein each of the plurality of cut slots is positioned adjacent an edge of the resection guide.

4. The resection system of claim 1, wherein at least one of the drill guide and the resection guide comprises at least one window positioned in a central portion thereof and extending from the first side through to the second side.

5. The resection system of claim 1, wherein the at least one cut slot comprises a single u-shaped cut slot, wherein each portion of the u-shaped cut slot is positioned adjacent to an edge of the resection guide.

* * * * *